United States Patent
Baldwin et al.

(10) Patent No.: US 8,765,743 B2
(45) Date of Patent: *Jul. 1, 2014

(54) COMPOUNDS

(75) Inventors: Ian Robert Baldwin, Stevenage (GB); Kenneth David Down, Stevenage (GB); Paul Faulder, Stevenage (GB); Simon Gaines, Stevenage (GB); Julie Nicole Hamblin, Stevenage (GB); Joelle Le, Stevenage (GB); Christopher James Lunniss, Stevenage (GB); Nigel James Parr, Stevenage (GB); Timothy John Ritchie, Stevenage (GB); Juliet Kay Simpson, Stevenage (GB); Christian Alan Paul Smethurst, Harlow (GB)

(73) Assignee: Glaxosmithkline Intellectual Property Development Limited, Brentford, Middlesex (GB)

( * ) Notice: Subject to any disclaimer, the term of this patent is extended or adjusted under 35 U.S.C. 154(b) by 343 days.

This patent is subject to a terminal disclaimer.

(21) Appl. No.: 12/994,253

(22) PCT Filed: Jun. 3, 2009

(86) PCT No.: PCT/EP2009/056841
§ 371 (c)(1),
(2), (4) Date: Jan. 12, 2011

(87) PCT Pub. No.: WO2009/147190
PCT Pub. Date: Dec. 10, 2009

(65) Prior Publication Data
US 2011/0118246 A1 May 19, 2011

Related U.S. Application Data

(60) Provisional application No. 61/158,426, filed on Mar. 9, 2009, provisional application No. 61/058,956, filed on Jun. 5, 2008.

(51) Int. Cl.
| *A61K 31/4439* | (2006.01) |
| *A61K 31/5377* | (2006.01) |
| *A61K 31/4545* | (2006.01) |
| *A61K 31/496* | (2006.01) |
| *C07D 401/14* | (2006.01) |
| *C07D 413/14* | (2006.01) |
| *C07D 405/14* | (2006.01) |
| *C07D 471/04* | (2006.01) |

(52) U.S. Cl.
USPC ............ 514/228.5; 514/234.2; 514/338; 514/234.5; 514/318; 514/300; 544/58.2; 544/131; 544/364; 544/127; 546/113; 546/119; 546/194

(58) Field of Classification Search
USPC ........... 514/228.5, 338, 234.5, 318, 253.09, 514/249, 300, 253.04, 228.2, 234.2, 303; 546/275.7, 194, 113, 119; 544/131, 544/364, 121, 349, 127, 362, 58.2
See application file for complete search history.

(56) References Cited

U.S. PATENT DOCUMENTS

| 8,076,326 | B2 | 12/2011 | Haupt et al. |
| 8,114,868 | B2 | 2/2012 | Himmelsbach |
| 8,138,178 | B2 | 3/2012 | Claremon et al. |
| 8,163,743 | B2 | 4/2012 | Baldwin et al. |
| 8,242,111 | B2 | 8/2012 | Claremon et al. |
| 2004/0009968 | A1 | 1/2004 | Binch et al. |
| 2005/0090529 | A1 | 4/2005 | McAlpine et al. |
| 2005/0288286 | A1 | 12/2005 | Flynn et al. |
| 2006/0135540 | A1 | 6/2006 | Lin et al. |
| 2006/0264433 | A1 | 11/2006 | Backes et al. |
| 2007/0037820 | A1 | 2/2007 | Edwards et al. |
| 2008/0032960 | A1 | 2/2008 | Knight et al. |
| 2008/0200523 | A1 | 8/2008 | Murthi et al. |
| 2009/0203690 | A1 | 8/2009 | Akritopoulou-Zanze et al. |
| 2010/0216792 | A1 | 8/2010 | Gorgens et al. |
| 2010/0256363 | A1 | 10/2010 | Xu |
| 2010/0280014 | A1 | 11/2010 | Haupt et al. |
| 2010/0280029 | A1 | 11/2010 | Hamblin et al. |

(Continued)

FOREIGN PATENT DOCUMENTS

| EP | 1679308 A1 | 7/2006 |
| WO | 02/067683 A1 | 9/2002 |

(Continued)

OTHER PUBLICATIONS

Finan et al., Biochemical society transactions (2004), vol. 32, part 2, pp. 378-382.*
Ameriks, et al., "Small Molecule Inhibitors of Phosphoinositide 3-kinase (PI3K) delta and gamma" Current Topics in Medicinal Chemistry; 2009; vol. 9(8); pp. 738-753.
Folkes, et al. The Identification of 2-(1H-indazol-4-yl)-6-(4-methanesulfonyl-piperazin-1-ylmethyl) -4-morpholin-4-yl-thieno [3,2-d] pyrimidine (GDC-0941) as a Potent, Selective, Orally Bioavailable inhibitor of class I PI3 kinase for the treatment of cancer Journal of Medicinal Chemistry; 2008; vol. 51(18); pp. 5522-5532.
Horig, et al., "From bench to clinic and back: Perspective on the 1st IQPC Translational Research Conference"; Journal of Translational Medicine; 2004; vol. 2(44); pp. 1-8.

(Continued)

*Primary Examiner* — Niloofar Rahmani
(74) *Attorney, Agent, or Firm* — Robert J. Smith

(57) ABSTRACT

The invention is directed to compounds of formula (I) and salts thereof. The compounds of the invention are inhibitors of PI3-kinase activity.

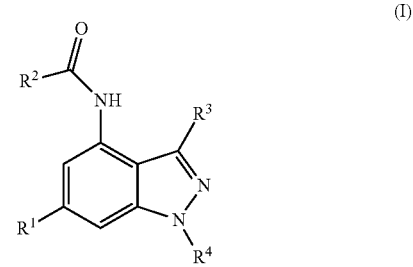

(I)

10 Claims, No Drawings

(56) References Cited

U.S. PATENT DOCUMENTS

| | | |
|---|---|---|
| 2010/0280045 A1 | 11/2010 | Hamblin et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0067448 A1* | 3/2011 | Matsumoto et al. ............... 65/36 |
| 2011/0118246 A1 | 5/2011 | Baldwin et al. |
| 2011/0124635 A1 | 5/2011 | Claremon et al. |
| 2011/0178063 A1* | 7/2011 | Baldwin et al. ........... 514/211.15 |
| 2011/0183973 A1* | 7/2011 | Baldwin et al. ............ 514/234.5 |
| 2011/0263583 A1 | 10/2011 | Claremon et al. |
| 2011/0263584 A1 | 10/2011 | Claremon et al. |
| 2012/0040969 A1 | 2/2012 | Haupt et al. |
| 2012/0108579 A1 | 5/2012 | Renz et al. |
| 2012/0129854 A1 | 5/2012 | Mihara et al. |
| 2012/0178746 A1 | 7/2012 | Claremon et al. |
| 2012/0184549 A1 | 7/2012 | Himmelsbach |
| 2012/0238559 A1* | 9/2012 | Baldwin et al. ............ 514/228.2 |
| 2012/0238571 A1* | 9/2012 | Baldwin et al. ............ 514/234.5 |
| 2012/0245171 A1* | 9/2012 | Baldwin et al. ............ 514/234.2 |

FOREIGN PATENT DOCUMENTS

| | | |
|---|---|---|
| WO | 02/083111 A2 | 10/2002 |
| WO | 03/000257 A1 | 1/2003 |
| WO | 03/051847 A1 | 6/2003 |
| WO | 03/064397 A1 | 8/2003 |
| WO | 2004/002480 A1 | 1/2004 |
| WO | 2004/014370 A2 | 2/2004 |
| WO | 2004/014881 A2 | 2/2004 |
| WO | 2004/014902 A2 | 2/2004 |
| WO | 2005/016245 A1 | 2/2005 |
| WO | 2005/075482 A1 | 8/2005 |
| WO | 2005/077345 A1 | 8/2005 |
| WO | 2005/077368 A2 | 8/2005 |
| WO | 2005/077373 A2 | 8/2005 |
| WO | 2005/082889 A1 | 9/2005 |
| WO | 2006/012226 A2 | 2/2006 |
| WO | 2006/014290 A2 | 2/2006 |
| WO | 2006/055752 A2 | 5/2006 |
| WO | 2006/060535 A2 | 6/2006 |
| WO | 2006/089076 A2 | 8/2006 |
| WO | 2007/017759 A2 | 2/2007 |
| WO | 2007/021573 A1 | 2/2007 |
| WO | 2007/022371 A2 | 2/2007 |
| WO | 2007/105637 A1 | 9/2007 |
| WO | 2007/126841 A2 | 11/2007 |
| WO | 2007/132171 A1 | 11/2007 |
| WO | 2008/016123 A1 | 2/2008 |
| WO | 2008/020229 A2 | 2/2008 |
| WO | WO 2008/024945 | 2/2008 |
| WO | 2008/037477 A1 | 4/2008 |
| WO | 2008/038136 A2 | 4/2008 |
| WO | 2008/057938 A1 | 5/2008 |
| WO | 2008/090382 A1 | 7/2008 |
| WO | 2009/000832 A1 | 12/2008 |
| WO | 2009/017664 A1 | 2/2009 |
| WO | 2009/134400 A1 | 11/2009 |
| WO | 2009/147187 A1 | 12/2009 |
| WO | 2009/147188 A1 | 12/2009 |
| WO | 2009/147189 A1 | 12/2009 |
| WO | 2009/147190 A1 | 12/2009 |
| WO | 2010/011314 A1 | 1/2010 |
| WO | 2010/043315 A1 | 4/2010 |
| WO | 2010/068287 A2 | 6/2010 |
| WO | 2010/125082 A1 | 11/2010 |
| WO | 2010/125134 A1 | 11/2010 |
| WO | 2010/127237 A2 | 11/2010 |
| WO | 2012/032065 A1 | 3/2012 |
| WO | 2012/032067 A1 | 3/2012 |
| WO | 2012/055846 A1 | 5/2012 |

OTHER PUBLICATIONS

Schafer, et al., "Failure is an option: learning from unsuccessful proof-of-concept trials" Drug Discovery Today; 2008; vol. 13 (21/22); pp. 913-916.

Verheijen, et al., "Phosphatidylinositol 3-kinase (PI3) inhibitors as anticancer drugs" Drugs of the Future, Prous Science; 2007; vol. 32(6); pp. 537-547.

* cited by examiner

COMPOUNDS

This application is a 371 of International Application No. PCT/EP2009/056841, filed 3 Jun. 2009, which claims the benefit of U.S. Provisional Application No. 61/158,426 filed 9 Mar. 2009 and US Provisional Application No. 61/058,956 filed 5 Jun. 2008, which is incorporated herein in their entirety.

FIELD OF THE INVENTION

The present invention is directed to certain novel compounds which are inhibitors of the activity or function of the phosphoinositide 3'OH kinase family (hereinafter PI3-kinases), processes for their preparation, pharmaceutical compositions comprising the compounds, and the use of the compounds or the compositions in the treatment of various disorders. More specifically, the compounds of the invention are inhibitors of the activity or function of, for example, PI3Kδ, PI3Kα, PI3Kβ and/or PI3Kγ. Compounds which are inhibitors of the activity or function of PI3-kinases may be useful in the treatment of disorders such as respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3 Kdelta) generate second messengers from the membrane phospholipid pools. Class I PI3Ks convert the membrane phospholipid PI(4,5)P$_2$ into PI(3,4,5)P$_3$, which functions as a second messenger. PI and PI(4)P are also substrates of PI3K and can be phosphorylated and converted into PI3P and PI(3,4)P$_2$, respectively. In addition, these phosphoinositides can be converted into other phosphoinositides by 5'-specific and 3'-specific phophatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life. Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate (PI(4,5)P$_2$) to produce phosphatidylinositol-3-phosphate (PI3P), phosphatidylinositol-3,4-bisphosphate (PI(3,4)P$_2$, and phosphatidylinositol-3,4,5-trisphosphate (PI(3,4,5)P$_3$, respectively. Class II PI3Ks can phosphorylate PI and PI4P. Class III PI3Ks can only phosphorylate PI (Vanhaesebroeck et al. (1997), above; Vanhaesebroeck et al., Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of PI(4,5)P$_2$ to PI(3,4,5)P$_3$

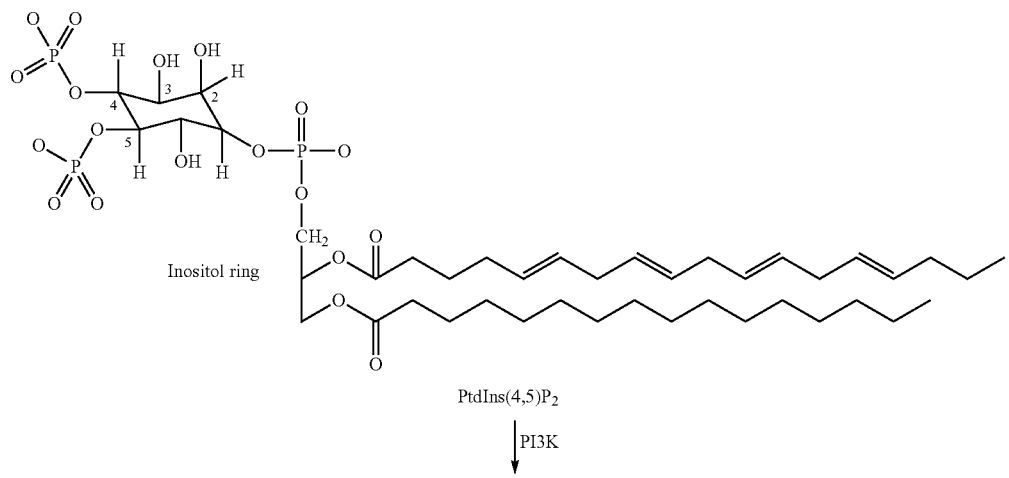

PtdIns(4,5)P$_2$

↓PI3K

-continued

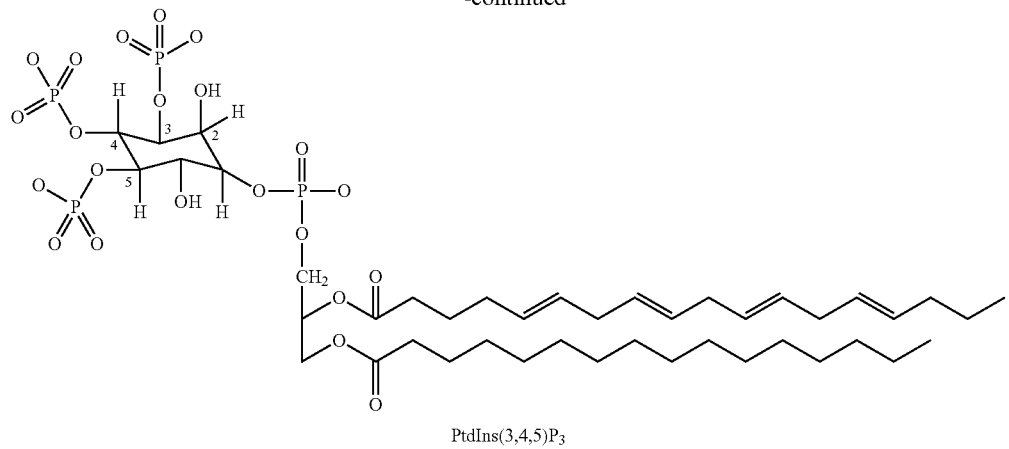

PtdIns(3,4,5)P$_3$

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3)P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, and are capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation is believed to be involved in a wide range of cellular responses including cell growth, differentiation, and apoptosis (Parker, Current Biology, 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pagès et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 μM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

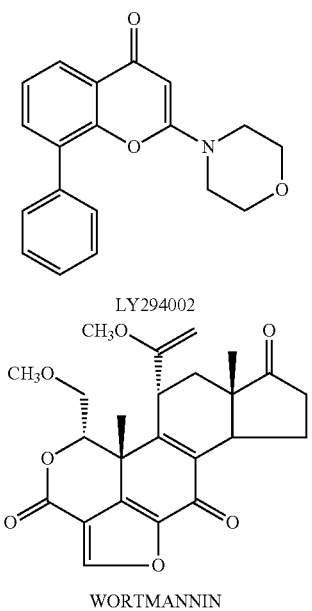

LY294002

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins (3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5) P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonist (LABA) in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutic benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al. J. Immunol. (2003) 170(5) p. 2647-54). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered novel compounds which are inhibitors of PI3-kinase activity. Compounds which are PI3-kinase inhibitors may be useful in the treatment of disorders associated with inappropriate PI3-kinase activity, for example in the treatment and prevention of disorders mediated by PI3-kinase mechanisms. Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

In one embodiment, compounds of the invention may show selectivity for PI3-kinases over other kinases. For example, the compounds of the invention may show selectivity for PI3-kinases over DNA-dependent protein kinase (DNA-PK).

In one embodiment, compounds of the invention may show selectivity for PI3Kδ over other PI3-kinases. For example, the compounds of the invention may show selectivity for PI3Kδ over PI3Kα and/or PI3Kβ.

SUMMARY OF THE INVENTION

The invention is directed to certain novel compounds. Specifically, the invention is directed to compounds of formula (I)

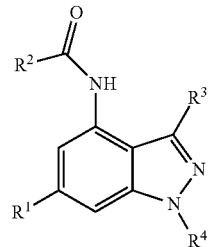

wherein $R^1$, $R^2$, $R^3$ and $R^4$ are as defined below, and salts thereof.

The compounds are inhibitors of PI3-kinase activity. Compounds which are PI3-kinase inhibitors may be useful in the treatment of disorders associated with inappropriate PI3-kinase activity, such as asthma and chronic obstructive pulmonary disease (COPD). Accordingly, the invention is further directed to pharmaceutical compositions comprising a compound of formula (I) or a pharmaceutically acceptable salt thereof. The invention is still further directed to methods of inhibiting PI3-kinase activity and treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation for the compounds of the invention.

DETAILED DESCRIPTION OF THE INVENTION

In one embodiment, the invention is directed to compounds of formula (I)

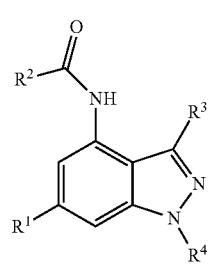

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN;
$R^2$ is pyridinyl optionally substituted by one or two substituents independently selected from $C_{1-6}$alkyl, $C_{2-6}$alkenyl, —$OR^5$, halo, —$(CH_2)_mNR^6R^7$, —$SO_2R^8$ and phenyl wherein the phenyl is optionally substituted by one or two substituents independently selected from $C_{1-6}$alkyl and —$OR^9$;
$R^3$ is hydrogen or fluoro;
$R^4$ is hydrogen, methyl or ethyl;
$R^5$ is hydrogen, $C_{1-6}$alkyl or 6-membered heterocyclyl wherein the 6-membered heterocyclyl contains one heteroatom selected from oxygen and nitrogen and is optionally substituted by $C_{1-6}$alkyl;

$R^6$ and $R^7$ are each independently hydrogen, $C_{1-6}$alkyl, $C_{3-6}$cycloalkyl or 6-membered heterocyclyl wherein the 6-membered heterocyclyl contains one heteroatom selected from oxygen and nitrogen and is optionally substituted by $C_{1-6}$alkyl, or $R^6$ and $R^7$, together with the nitrogen atom to which they are attached, are linked to form a 5- or 6-membered heterocyclyl or a 10-membered bicyclic heterocyclyl wherein the 5- or 6-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl; $C_{3-6}$cycloalkyl; halo; oxo; phenyl optionally substituted by halo; pyridinyl; —$(CH_2)_nOR^{19}$; —$(CH_2)_pNR^{11}R^{12}$; —$COR^{13}$; and —$SO_2R^{14}$;

$R^8$, $R^{13}$ and $R^{14}$ are each independently $C_{1-6}$alkyl;

$R^9$ is hydrogen or $C_{1-6}$alkyl;

$R^{10}$ is hydrogen, $C_{1-6}$alkyl or —$(CH_2)_q$phenyl;

$R^{11}$ and $R^{12}$, together with the nitrogen atom to which they are attached, are linked to form a 5- or 6-membered heterocyclyl optionally containing an oxygen atom; and m, n, p and q are each independently 0, 1 or 2;

and salts thereof (hereinafter "compounds of the invention").

In a further embodiment, the invention is directed to compounds of formula (IA)

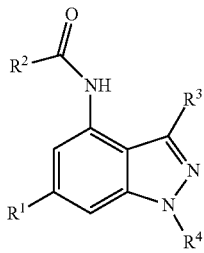

(IA)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN;

$R^2$ is pyridinyl optionally substituted by one or two substituents independently selected from $C_{1-6}$alkyl, $C_{2-6}$alkenyl, —$OR^5$, halo, —$(CH_2)_mNR^6R^7$, —$SO_2R^9$ and phenyl wherein the phenyl is optionally substituted by one or two substituents independently selected from $C_{1-6}$alkyl and —$OR^9$;

$R^3$ is hydrogen or fluoro;

$R^4$ is hydrogen, methyl or ethyl;

$R^5$ is hydrogen, $C_{1-6}$alkyl or 6-membered heterocyclyl wherein the 6-membered heterocyclyl contains one heteroatom selected from oxygen and nitrogen and is optionally substituted by $C_{1-6}$alkyl;

$R^6$ and $R^7$ are each independently hydrogen, $C_{1-6}$alkyl, $C_{3-6}$cycloalkyl or 6-membered heterocyclyl wherein the 6-membered heterocyclyl contains one heteroatom selected from oxygen and nitrogen and is optionally substituted by $C_{1-6}$alkyl, or $R^6$ and $R^7$, together with the nitrogen atom to which they are attached, are linked to form a 5- or 6-membered heterocyclyl optionally containing an oxygen atom or a further nitrogen atom wherein the 5- or 6-membered heterocyclyl is optionally substituted by $C_{1-6}$alkyl;

$R^8$ is $C_{1-6}$alkyl;

$R^9$ is hydrogen or $C_{1-6}$alkyl; and m is 0, 1 or 2;

and salts thereof.

In one embodiment, $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl. In a further embodiment, $R^1$ is indolyl optionally substituted by $C_{1-6}$alkyl, for example $C_{1-4}$alkyl such as methyl.

In one embodiment, $R^2$ is pyridinyl optionally substituted by one or two substituents independently selected from $C_{1-6}$alkyl and —$(CH_2)_mNR^6R^7$. In another embodiment, $R^2$ is pyridinyl optionally substituted by $C_{1-6}$alkyl, for example $C_{1-4}$alkyl such as methyl or isopropyl. In a further embodiment, $R^2$ is pyridinyl optionally substituted by —$(CH_2)_mNR^6R^7$.

In one embodiment, $R^3$ is hydrogen.

In one embodiment, $R^4$ is hydrogen. In another embodiment, $R^4$ is methyl.

In one embodiment, $R^5$ is hydrogen or $C_{1-6}$alkyl, for example $C_{1-4}$alkyl such as methyl or ethyl.

In one embodiment, $R^6$ and $R^7$ are each independently hydrogen, $C_{1-6}$alkyl, $C_{3-6}$cycloalkyl or 6-membered heterocyclyl wherein the 6-membered heterocyclyl contains one heteroatom selected from oxygen and nitrogen and is optionally substituted by $C_{1-6}$alkyl, or $R^6$ and $R^7$, together with the nitrogen atom to which they are attached, are linked to form a 5- or 6-membered heterocyclyl optionally containing an oxygen atom or a further nitrogen atom wherein the 5- or 6-membered heterocyclyl is optionally substituted by $C_{1-6}$alkyl. In another embodiment, $R^6$ is hydrogen and $R^7$ is $C_{1-6}$alkyl, $C_{3-6}$cycloalkyl or 6-membered heterocyclyl wherein the 6-membered heterocyclyl contains one heteroatom selected from oxygen and nitrogen and is optionally substituted by $C_{1-6}$alkyl. In another embodiment, $R^6$ is hydrogen and $R^7$ is $C_{3-6}$cycloalkyl, for example cyclopropyl. In another embodiment, $R^6$ and $R^7$, together with the nitrogen atom to which they are attached, are linked to form a 5- or 6-membered heterocyclyl optionally containing an oxygen atom or a further nitrogen atom wherein the 5- or 6-membered heterocyclyl is optionally substituted by $C_{1-6}$alkyl. In another embodiment, $R^6$ and $R^7$, together with the nitrogen atom to which they are attached, are linked to form a 6-membered heterocyclyl optionally containing an oxygen atom or a further nitrogen atom wherein the 5- or 6-membered heterocyclyl is optionally substituted by $C_{1-6}$alkyl. In a further embodiment, $R^6$ and $R^7$, together with the nitrogen atom to which they are attached, are linked to form a 6-membered heterocyclyl wherein the 6-membered heterocyclyl optionally contains an oxygen atom or a further nitrogen atom and is optionally substituted by one or two substituents independently selected from $C_{1-6}$alkyl.

In one embodiment, $R^8$ is $C_{1-4}$alkyl such as methyl.

In one embodiment, $R^9$ is $C_{1-4}$alkyl such as methyl.

In one embodiment, $R^{10}$ is —$(CH_2)_q$phenyl.

In one embodiment, $R^{11}$ and $R^{12}$, together with the nitrogen atom to which they are attached, are linked to form a pyrrolidinyl. In a further embodiment, $R^{11}$ and $R^{12}$, together with the nitrogen atom to which they are attached, are linked to form a morpholinyl.

In one embodiment, $R^{13}$ is $C_{1-4}$alkyl such as methyl.

In one embodiment, $R^{14}$ is $C_{1-4}$alkyl such as methyl.

In one embodiment, m is 0. In a further embodiment, m is 1.

In one embodiment, n is 0. In a further embodiment, n is 1.

In one embodiment, p is one. In a further embodiment, p is 2.

In one embodiment, q is 0. In a further embodiment, q is 1.

It is to be understood that the present invention covers all combinations of substituent groups described hereinabove.

Compounds of the invention include the compounds of Examples 1 to 100 and salts thereof.

In one embodiment, the compound of the invention is:
N-[6-(1H-indol-4-yl)-1H-indazol-4-yl]-3-methyl-2-pyridinecarboxamide;
3-bromo-N-[6-(1H-indol-4-yl)-1H-indazol-4-yl]-2-pyridinecarboxamide;
5-fluoro-N-[6-(1H-indol-4-yl)-1H-indazol-4-yl]-2-pyridinecarboxamide;
N-[6-(1H-indol-4-yl)-1H-indazol-4-yl]-6-[5-methyl-2-(methyloxy)phenyl]-2-pyridinecarboxamide;
N-[6-(1H-indol-4-yl)-1H-indazol-4-yl]-6-(methyloxy)-2-pyridinecarboxamide;
N-[6-(1H-indol-4-yl)-1H-indazol-4-yl]-6-methyl-2-pyridinecarboxamide;
3,5-difluoro-N-[6-(1H-indol-4-yl)-1H-indazol-4-yl]-2-pyridinecarboxamide;
N-[1-ethyl-6-(1H-indol-4-yl)-1H-indazol-4-yl]-6-methyl-2-pyridinecarboxamide;
N-[6-(1H-indol-4-yl)-1-methyl-1H-indazol-4-yl]-2-pyridinecarboxamide;
N-[6-(1H-indol-4-yl)-1H-indazol-4-yl]-3-(methyloxy)-2-pyridinecarboxamide;
6-[(dimethylamino)methyl]-N-[6-(1H-indol-4-yl)-1H-indazol-4-yl]-2-pyridinecarboxamide;
N-[6-(1H-indol-4-yl)-1H-indazol-4-yl]-6-(4-morpholinylmethyl)-2-pyridinecarboxamide;
N-[6-(1H-indol-4-yl)-1H-indazol-4-yl]-6-(1-piperidinylmethyl)-2-pyridinecarboxamide; 3-fluoro-N-[6-(1H-indol-4-yl)-1H-indazol-4-yl]-2-pyridinecarboxamide;
N-[6-(1H-indol-4-yl)-1H-indazol-4-yl]-3-pyridinecarboxamide;
N-[6-(1H-indol-4-yl)-1H-indazol-4-yl]-3-(methylsulfonyl)-2-pyridinecarboxamide;
6-chloro-3-fluoro-N-[6-(1H-indol-4-yl)-1H-indazol-4-yl]-2-pyridinecarboxamide;
6-chloro-N-[6-(1H-indol-4-yl)-1H-indazol-4-yl]-2-pyridinecarboxamide;
N-[6-(1H-indol-4-yl)-1H-indazol-4-yl]-6-(methylamino)-2-pyridinecarboxamide;
N-[6-(1H-indol-4-yl)-1H-indazol-4-yl]-6-[(1-methylethyl)amino]-2-pyridinecarboxamide;
6-(ethylamino)-N-[6-(1H-indol-4-yl)-1H-indazol-4-yl]-2-pyridinecarboxamide;
6-(diethylamino)-N-[6-(1H-indol-4-yl)-1H-indazol-4-yl]-2-pyridinecarboxamide;
6-(cyclopropylamino)-N-[6-(1H-indol-4-yl)-1H-indazol-4-yl]-2-pyridinecarboxamide;
N-[6-(1H-indol-4-yl)-1H-indazol-4-yl]-6-(4-methyl-1-piperazinyl)-2-pyridinecarboxamide;
N-[6-(1H-indol-4-yl)-1H-indazol-4-yl]-6-(1-pyrrolidinyl)-2-pyridinecarboxamide;
6-(dimethylamino)-N-[6-(1H-indol-4-yl)-1H-indazol-4-yl]-2-pyridinecarboxamide;
3,6-dichloro-N-[6-(1H-indol-4-yl)-1H-indazol-4-yl]-2-pyridinecarboxamide;
3-chloro-N-[6-(1H-indol-4-yl)-1H-indazol-4-yl]-6-(4-morpholinyl)-2-pyridinecarboxamide;
3-chloro-N-[6-(1H-indol-4-yl)-1H-indazol-4-yl]-6-(1-piperidinyl)-2-pyridinecarboxamide;
3-chloro-6-(dimethylamino)-N-[6-(1H-indol-4-yl)-1H-indazol-4-yl]-2-pyridinecarboxamide;
6-fluoro-N-[6-(1H-indol-4-yl)-1H-indazol-4-yl]-2-pyridinecarboxamide;
N-[6-(1H-indol-4-yl)-1H-indazol-4-yl]-6-[methyl(tetrahydro-2H-pyran-4-yl)amino]-2-pyridinecarboxamide;
N-[6-(1H-indol-4-yl)-1H-indazol-4-yl]-6-[(1-methyl-4-piperidinyl)amino]-2-pyridinecarboxamide;
N-[6-(1H-indol-4-yl)-1H-indazol-4-yl]-6-(tetrahydro-2H-pyran-4-ylamino)-2-pyridinecarboxamide;
6-chloro-3-(dimethylamino)-N-[6-(1H-indol-4-yl)-1H-indazol-4-yl]-2-pyridinecarboxamide;
3-(dimethylamino)-N-[6-(1H-indol-4-yl)-1H-indazol-4-yl]-6-(4-morpholinyl)-2-pyridinecarboxamide;
3-(dimethylamino)-N-[6-(1H-indol-4-yl)-1H-indazol-4-yl]-6-(1-piperidinyl)-2-pyridinecarboxamide;
3-(dimethylamino)-N-[6-(1H-indol-4-yl)-1H-indazol-4-yl]-6-(methylamino)-2-pyridinecarboxamide;
3-(dimethylamino)-6-(ethylamino)-N-[6-(1H-indol-4-yl)-1H-indazol-4-yl]-2-pyridinecarboxamide;
6-chloro-N-[6-(1H-indol-4-yl)-1H-indazol-4-yl]-3-(4-morpholinyl)-2-pyridinecarboxamide;
6-chloro-N-[6-(1H-indol-4-yl)-1H-indazol-4-yl]-3-(1-piperidinyl)-2-pyridinecarboxamide;
N-[6-(1H-indol-4-yl)-1H-indazol-4-yl]-5-(4-morpholinyl)-2-pyridinecarboxamide;
N-[6-(1H-indol-4-yl)-1H-indazol-4-yl]-5-(1-piperidinyl)-2-pyridinecarboxamide;
3-chloro-N-[6-(1H-indol-4-yl)-1H-indazol-4-yl]-2-pyridinecarboxamide;
6-amino-N-[6-(1H-indol-4-yl)-1H-indazol-4-yl]-2-pyridinecarboxamide;
5-amino-N-[6-(1H-indol-4-yl)-1H-indazol-4-yl]-2-pyridinecarboxamide;
N-[6-(1H-indol-4-yl)-1H-indazol-4-yl]-5-methyl-2-pyridinecarboxamide;
N-[6-(1H-indol-4-yl)-1H-indazol-4-yl]-2-methyl-3-pyridinecarboxamide;
3-amino-N-[6-(1H-indol-4-yl)-1H-indazol-4-yl]-2-pyridinecarboxamide;
N-[6-(1H-indol-4-yl)-1H-indazol-4-yl]-4-(methylamino)-2-pyridinecarboxamide;
N-[6-(1H-indol-4-yl)-1H-indazol-4-yl]-2-pyridinecarboxamide;
N-[6-(1H-indol-6-yl)-1H-indazol-4-yl]-2-pyridinecarboxamide;
N-[6-(1-methyl-1H-indol-5-yl)-1H-indazol-4-yl]-2-pyridinecarboxamide;
N-[6-(1H-indol-4-yl)-1H-indazol-4-yl]-2-(methyloxy)-3-pyridinecarboxamide;
2-(ethyloxy)-N-[6-(1H-indol-4-yl)-1H-indazol-4-yl]-3-pyridinecarboxamide;
5-bromo-N-[6-(1H-indol-4-yl)-1H-indazol-4-yl]-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1H-indazol-4-yl]-6-(4-morpholinyl)-2-pyridinecarboxamide;
N-[6-(1H-indol-4-yl)-1H-indazol-4-yl]-6-oxo-1,6-dihydro-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1-methyl-1H-indazol-4-yl]-6-methyl-2-pyridinecarboxamide;
N-[6-(1H-indol-4-yl)-1H-indazol-4-yl]-3-(1-methylethenyl)-2-pyridinecarboxamide;
N-[6-(1H-indol-4-yl)-1H-indazol-4-yl]-3-(1-methylethyl)-2-pyridinecarboxamide;

N-[6-(1H-indol-4-yl)-1H-indazol-4-yl]-6-(tetrahydro-2H-pyran-4-yloxy)-2-pyridinecarboxamide;
N-[6-(1H-indol-4-yl)-1H-indazol-4-yl]-6-[(4-methyl-1-piperazinyl)methyl]-2-pyridinecarboxamide;
N-[3-fluoro-6-(1H-indol-4-yl)-1H-indazol-4-yl]-3-methyl-2-pyridinecarboxamide;
6-[(4,4-dimethyl-1-piperidinyl)methyl]-N-[6-(1H-indol-4-yl)-1H-indazol-4-yl]-2-pyridinecarboxamide;
6-[(3,3-dimethyl-1-piperidinyl)methyl]-N-[6-(1H-indol-4-yl)-1H-indazol-4-yl]-2-pyridinecarboxamide;
N-[6-(1H-indol-4-yl)-1H-indazol-4-yl]-6-{[4-(2-methylpropyl)-1-piperazinyl]methyl}-2-pyridinecarboxamide;
N-[6-(1H-indol-4-yl)-1H-indazol-4-yl]-6-{[4-(1-methylethyl)-1-piperazinyl]methyl}-2-pyridinecarboxamide;
N-[6-(1H-indol-4-yl)-1H-indazol-4-yl]-6-{[4-(1-methylethyl)-1-piperidinyl]methyl}-2-pyridinecarboxamide;
N-[6-(1H-indol-4-yl)-1H-indazol-4-yl]-6-({4-[2-(4-morpholinyl)ethyl]-1-piperazinyl}methyl)-2-pyridinecarboxamide;
N-[6-(1H-indol-4-yl)-1H-indazol-4-yl]-6-(octahydro-4H-1,4-benzoxazin-4-ylmethyl)-2-pyridinecarboxamide;
6-{[(2R,6S)-2,6-dimethyl-4-morpholinyl]methyl}-N-[6-(1H-indol-4-yl)-1H-indazol-4-yl]-2-pyridinecarboxamide;
6-{[4-(4-fluorophenyl)-1-piperazinyl]methyl}-N-[6-(1H-indol-4-yl)-1H-indazol-4-yl]-2-pyridinecarboxamide;
N-[6-(1H-indol-4-yl)-1H-indazol-4-yl]-6-(octahydro-2H-pyrido[1,2-a]pyrazin-2-ylmethyl)-2-pyridinecarboxamide;
N-[6-(1H-indol-4-yl)-1H-indazol-4-yl]-6-{[2-(1-pyrrolidinylmethyl)-4-morpholinyl]methyl}-2-pyridinecarboxamide;
N-[6-(1H-indol-4-yl)-1H-indazol-4-yl]-6-{[2-(2-methylpropyl)-4-morpholinyl]methyl}-2-pyridinecarboxamide;
N-[6-(1H-indol-4-yl)-1H-indazol-4-yl]-6-{[3-methyl-4-(1-methylethyl)-1-piperazinyl]methyl}-2-pyridinecarboxamide;
N-[6-(1H-indol-4-yl)-1H-indazol-4-yl]-6-[(3-phenyl-1-piperidinyl)methyl]-2-pyridinecarboxamide;
N-[6-(1H-indol-4-yl)-1H-indazol-4-yl]-6-({2-[(phenyloxy)methyl]-4-morpholinyl}methyl)-2-pyridinecarboxamide;
N-[6-(1H-indol-4-yl)-1H-indazol-4-yl]-6-({3-[(phenylmethyl)oxy]-1-piperidinyl}methyl)-2-pyridinecarboxamide;
6-{[4-(1-ethylpropyl)-1-piperazinyl]methyl}-N-[6-(1H-indol-4-yl)-1H-indazol-4-yl]-2-pyridinecarboxamide;
6-[(4-cyclopentyl-1-piperazinyl)methyl]-N-[6-(1H-indol-4-yl)-1H-indazol-4-yl]-2-pyridinecarboxamide;
6-methyl-N-[1-methyl-6-(1H-pyrrolo[2,3-b]pyridin-4-yl)-1H-indazol-4-yl]-2-pyridinecarboxamide;
6-(4-morpholinylmethyl)-N-[6-(1H-pyrrolo[2,3-b]pyridin-4-yl)-1H-indazol-4-yl]-2-pyridinecarboxamide;
6-(1-piperidinylmethyl)-N-[6-(1H-pyrrolo[2,3-b]pyridin-4-yl)-1H-indazol-4-yl]-2-pyridinecarboxamide;
6-[(4-methyl-3-oxo-1-piperazinyl)methyl]-N-[6-(1H-pyrrolo[2,3-b]pyridin-4-yl)-1H-indazol-4-yl]-2-pyridinecarboxamide;
6-[(4-acetyl-1-piperazinyl)methyl]-N-[6-(1H-pyrrolo[2,3-b]pyridin-4-yl)-1H-indazol-4-yl]-2-pyridinecarboxamide;
6-{[4-(methylsulfonyl)-1-piperazinyl]methyl}-N-[6-(1H-pyrrolo[2,3-b]pyridin-4-yl)-1H-indazol-4-yl]-2-pyridinecarboxamide;
6-[(1,1-dioxido-4-thiomorpholinyl)methyl]-N-[6-(1H-pyrrolo[2,3-b]pyridin-4-yl)-1H-indazol-4-yl]-2-pyridinecarboxamide;
6-{[(2R,6S)-2,6-dimethyl-4-morpholinyl]methyl}-N-[6-(1H-pyrrolo[2,3-b]pyridin-4-yl)-1H-indazol-4-yl]-2-pyridinecarboxamide;
6-{[3-methyl-4-(1-methylethyl)-1-piperazinyl]methyl}-N-[6-(1H-pyrrolo[2,3-b]pyridin-4-yl)-1H-indazol-4-yl]-2-pyridinecarboxamide;
6-[(4,4-difluoro-1-piperidinyl)methyl]-N-[6-(1H-pyrrolo[2,3-b]pyridin-4-yl)-1H-indazol-4-yl]-2-pyridinecarboxamide;
6-(4-morpholinylmethyl)-N-[6-(1H-pyrazolo[3,4-b]pyridin-5-yl)-1H-indazol-4-yl]-2-pyridinecarboxamide;
6-{[4-(methylsulfonyl)-1-piperazinyl]methyl}-N-[6-(1H-pyrazolo[3,4-b]pyridin-5-yl)-1H-indazol-4-yl]-2-pyridinecarboxamide;
6-[(1,1-dioxido-4-thiomorpholinyl)methyl]-N-[6-(1H-pyrazolo[3,4-b]pyridin-5-yl)-1H-indazol-4-yl]-2-pyridinecarboxamide;
6-[(4,4-difluoro-1-piperidinyl)methyl]-N-[6-(1H-pyrazolo[3,4-b]pyridin-5-yl)-1H-indazol-4-yl]-2-pyridinecarboxamide;
6-{[(2R,6S)-2,6-dimethyl-4-morpholinyl]methyl}-N-[6-(1H-pyrazolo[3,4-b]pyridin-5-yl)-1H-indazol-4-yl]-2-pyridinecarboxamide;
6-{[3-methyl-4-(1-methylethyl)-1-piperazinyl]methyl}-N-[6-(1H-pyrazolo[3,4-b]pyridin-5-yl)-1H-indazol-4-yl]-2-pyridinecarboxamide; or a salt thereof.

In another embodiment, the compound of the invention is:
N-[6-(1H-indol-4-yl)-1H-indazol-4-yl]-3-methyl-2-pyridinecarboxamide;
3-bromo-N-[6-(1H-indol-4-yl)-1H-indazol-4-yl]-2-pyridinecarboxamide;
5-fluoro-N-[6-(1H-indol-4-yl)-1H-indazol-4-yl]-2-pyridinecarboxamide;
N-[6-(1H-indol-4-yl)-1H-indazol-4-yl]-6-[5-methyl-2-(methyloxy)phenyl]-2-pyridinecarboxamide;
N-[6-(1H-indol-4-yl)-1H-indazol-4-yl]-6-(methyloxy)-2-pyridinecarboxamide;
N-[6-(1H-indol-4-yl)-1H-indazol-4-yl]-6-methyl-2-pyridinecarboxamide;
3,5-difluoro-N-[6-(1H-indol-4-yl)-1H-indazol-4-yl]-2-pyridinecarboxamide;
N-[1-ethyl-6-(1H-indol-4-yl)-1H-indazol-4-yl]-6-methyl-2-pyridinecarboxamide;
N-[6-(1H-indol-4-yl)-1-methyl-1H-indazol-4-yl]-2-pyridinecarboxamide;
N-[6-(1H-indol-4-yl)-1H-indazol-4-yl]-3-(methyloxy)-2-pyridinecarboxamide;
6-[(dimethylamino)methyl]-N-[6-(1H-indol-4-yl)-1H-indazol-4-yl]-2-pyridinecarboxamide;
N-[6-(1H-indol-4-yl)-1H-indazol-4-yl]-6-(4-morpholinylmethyl)-2-pyridinecarboxamide;
N-[6-(1H-indol-4-yl)-1H-indazol-4-yl]-6-(1-piperidinylmethyl)-2-pyridinecarboxamide; 3-fluoro-N-[6-(1H-indol-4-yl)-1H-indazol-4-yl]-2-pyridinecarboxamide;
N-[6-(1H-indol-4-yl)-1H-indazol-4-yl]-3-pyridinecarboxamide;
N-[6-(1H-indol-4-yl)-1H-indazol-4-yl]-3-(methylsulfonyl)-2-pyridinecarboxamide;
6-chloro-3-fluoro-N-[6-(1H-indol-4-yl)-1H-indazol-4-yl]-2-pyridinecarboxamide;
6-chloro-N-[6-(1H-indol-4-yl)-1H-indazol-4-yl]-2-pyridinecarboxamide;
N-[6-(1H-indol-4-yl)-1H-indazol-4-yl]-6-(methylamino)-2-pyridinecarboxamide;
N-[6-(1H-indol-4-yl)-1H-indazol-4-yl]-6-[(1-methylethyl)amino]-2-pyridinecarboxamide;

6-(ethylamino)-N-[6-(1H-indol-4-yl)-1H-indazol-4-yl]-2-pyridinecarboxamide;
6-(diethylamino)-N-[6-(1H-indol-4-yl)-1H-indazol-4-yl]-2-pyridinecarboxamide;
6-(cyclopropylamino)-N-[6-(1H-indol-4-yl)-1H-indazol-4-yl]-2-pyridinecarboxamide;
N-[6-(1H-indol-4-yl)-1H-indazol-4-yl]-6-(4-methyl-1-piperazinyl)-2-pyridinecarboxamide;
N-[6-(1H-indol-4-yl)-1H-indazol-4-yl]-6-(1-pyrrolidinyl)-2-pyridinecarboxamide;
6-(dimethylamino)-N-[6-(1H-indol-4-yl)-1H-indazol-4-yl]-2-pyridinecarboxamide;
3,6-dichloro-N-[6-(1H-indol-4-yl)-1H-indazol-4-yl]-2-pyridinecarboxamide;
3-chloro-N-[6-(1H-indol-4-yl)-1H-indazol-4-yl]-6-(4-morpholinyl)-2-pyridinecarboxamide;
3-chloro-N-[6-(1H-indol-4-yl)-1H-indazol-4-yl]-6-(1-piperidinyl)-2-pyridinecarboxamide;
3-chloro-6-(dimethylamino)-N-[6-(1H-indol-4-yl)-1H-indazol-4-yl]-2-pyridinecarboxamide;
6-fluoro-N-[6-(1H-indol-4-yl)-1H-indazol-4-yl]-2-pyridinecarboxamide;
N-[6-(1H-indol-4-yl)-1H-indazol-4-yl]-6-[methyl(tetrahydro-2H-pyran-4-yl)amino]-2-pyridinecarboxamide;
N-[6-(1H-indol-4-yl)-1H-indazol-4-yl]-6-[(1-methyl-4-piperidinyl)amino]-2-pyridinecarboxamide;
N-[6-(1H-indol-4-yl)-1H-indazol-4-yl]-6-(tetrahydro-2H-pyran-4-ylamino)-2-pyridinecarboxamide;
6-chloro-3-(dimethylamino)-N-[6-(1H-indol-4-yl)-1H-indazol-4-yl]-2-pyridinecarboxamide;
3-(dimethylamino)-N-[6-(1H-indol-4-yl)-1H-indazol-4-yl]-6-(4-morpholinyl)-2-pyridinecarboxamide;
3-(dimethylamino)-N-[6-(1H-indol-4-yl)-1H-indazol-4-yl]-6-(1-piperidinyl)-2-pyridinecarboxamide;
3-(dimethylamino)-N-[6-(1H-indol-4-yl)-1H-indazol-4-yl]-6-(methylamino)-2-pyridinecarboxamide;
3-(dimethylamino)-6-(ethylamino)-N-[6-(1H-indol-4-yl)-1H-indazol-4-yl]-2-pyridinecarboxamide;
6-chloro-N-[6-(1H-indol-4-yl)-1H-indazol-4-yl]-3-(4-morpholinyl)-2-pyridinecarboxamide;
6-chloro-N-[6-(1H-indol-4-yl)-1H-indazol-4-yl]-3-(1-piperidinyl)-2-pyridinecarboxamide;
N-[6-(1H-indol-4-yl)-1H-indazol-4-yl]-5-(4-morpholinyl)-2-pyridinecarboxamide;
N-[6-(1H-indol-4-yl)-1H-indazol-4-yl]-5-(1-piperidinyl)-2-pyridinecarboxamide;
3-chloro-N-[6-(1H-indol-4-yl)-1H-indazol-4-yl]-2-pyridinecarboxamide;
6-amino-N-[6-(1H-indol-4-yl)-1H-indazol-4-yl]-2-pyridinecarboxamide;
5-amino-N-[6-(1H-indol-4-yl)-1H-indazol-4-yl]-2-pyridinecarboxamide;
N-[6-(1H-indol-4-yl)-1H-indazol-4-yl]-5-methyl-2-pyridinecarboxamide;
N-[6-(1H-indol-4-yl)-1H-indazol-4-yl]-2-methyl-3-pyridinecarboxamide;
3-amino-N-[6-(1H-indol-4-yl)-1H-indazol-4-yl]-2-pyridinecarboxamide;
N-[6-(1H-indol-4-yl)-1H-indazol-4-yl]-4-(methylamino)-2-pyridinecarboxamide;
N-[6-(1H-indol-4-yl)-1H-indazol-4-yl]-2-pyridinecarboxamide;
N-[6-(1H-indol-6-yl)-1H-indazol-4-yl]-2-pyridinecarboxamide;
N-[6-(1-methyl-1H-indol-5-yl)-1H-indazol-4-yl]-2-pyridinecarboxamide;
N-[6-(1H-indol-4-yl)-1H-indazol-4-yl]-2-(methyloxy)-3-pyridinecarboxamide;
2-(ethyloxy)-N-[6-(1H-indol-4-yl)-1H-indazol-4-yl]-3-pyridinecarboxamide;
5-bromo-N-[6-(1H-indol-4-yl)-1H-indazol-4-yl]-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1H-indazol-4-yl]-6-(4-morpholinyl)-2-pyridinecarboxamide;
N-[6-(1H-indol-4-yl)-1H-indazol-4-yl]-6-oxo-1,6-dihydro-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1-methyl-1H-indazol-4-yl]-6-methyl-2-pyridinecarboxamide;
N-[6-(1H-indol-4-yl)-1H-indazol-4-yl]-3-(1-methylethenyl)-2-pyridinecarboxamide;
N-[6-(1H-indol-4-yl)-1H-indazol-4-yl]-3-(1-methylethyl)-2-pyridinecarboxamide;
N-[6-(1H-indol-4-yl)-1H-indazol-4-yl]-6-(tetrahydro-2H-pyran-4-yloxy)-2-pyridinecarboxamide;
N-[6-(1H-indol-4-yl)-1H-indazol-4-yl]-6-[(4-methyl-1-piperazinyl)methyl]-2-pyridinecarboxamide;
N-[3-fluoro-6-(1H-indol-4-yl)-1H-indazol-4-yl]-3-methyl-2-pyridinecarboxamide; or a salt thereof.

In another embodiment, the compound of the invention is:
N-[6-(1H-indol-4-yl)-1H-indazol-4-yl]-6-methyl-2-pyridinecarboxamide;
N-[6-(1H-indol-4-yl)-1H-indazol-4-yl]-6-(4-morpholinylmethyl)-2-pyridinecarboxamide;
N-[6-(1H-indol-4-yl)-1H-indazol-4-yl]-6-(1-piperidinylmethyl)-2-pyridinecarboxamide;
6-(cyclopropylamino)-N-[6-(1H-indol-4-yl)-1H-indazol-4-yl]-2-pyridinecarboxamide;
N-[6-(1H-indol-4-yl)-1H-indazol-4-yl]-6-(4-morpholinyl)-2-pyridinecarboxamide;
N-[6-(1H-indol-4-yl)-1H-indazol-4-yl]-6-[(4-methyl-1-piperazinyl)methyl]-2-pyridinecarboxamide;
N-[6-(1H-indol-4-yl)-1H-indazol-4-yl]-3-(1-methylethyl)-2-pyridinecarboxamide; or a salt thereof.

In a further embodiment, the compound of the invention is:
N-[6-(1H-indol-4-yl)-1H-indazol-4-yl]-6-{[4-(1-methylethyl)-1-piperazinyl]methyl}-2-pyridinecarboxamide;
6-{[(2R,6S)-2,6-dimethyl-4-morpholinyl]methyl}-N-[6-(1H-indol-4-yl)-1H-indazol-4-yl]-2-pyridinecarboxamide; or
a salt thereof.

Terms and Definitions

"Alkyl" refers to a saturated hydrocarbon chain having the specified number of member atoms. For example, $C_{1-6}$alkyl refers to an alkyl group having from 1 to 6 member atoms. Similarly, $C_{1-4}$alkyl refers to an alkyl group having from 1 to 4 member atoms. Alkyl groups may be straight or branched. Representative branched alkyl groups have one, two, or three branches. Alkyl includes methyl, ethyl, propyl(n-propyl and isopropyl), butyl(n-butyl, isobutyl, and t-butyl), pentyl(n-pentyl, isopentyl, and neopentyl), and hexyl. In one embodiment, alkyl is methyl. In another embodiment, alkyl is ethyl. In a further embodiment, alkyl is isopropyl.

"Alkenyl" refers to a hydrocarbon chain having the specified number of member atoms and at least one double bond. For example, $C_{2-6}$alkenyl refers to an alkenyl group having from 2 to 6 member atoms, for example 2 to 4 member atoms. Alkenyl groups may be straight or branched. Alkenyl includes ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. In one embodiment, alkenyl is 2-propenyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl includes cyclopropyl, cyclobutyl, cyclopentyl, and cyclohexyl. In one embodiment, cycloalkyl is cyclopropyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo. In one embodiment, the halogen radical is fluoro, chloro or bromo.

"9- or 10-Membered bicyclic heteroaryl" refers to a fused bicyclic aromatic ring system containing from 1 to 3 heteroatoms as member atoms. Heteroaryl groups containing more than one heteroatom may contain different heteroatoms. Heteroaryl groups may be optionally substituted if so defined herein. The heteroaryl groups herein are fused bicyclic ring systems having 9 or 10 member atoms. Bicyclic heteroaryl includes indolyl, isoindolyl, indolizinyl, benzofuranyl, isobenzofuranyl, indazolyl, purinyl, benzimidazolyl, pyrrolopyridinyl, pyrazolopyridinyl, pyrrolopyrimidinyl, quinolyl, isoquinolinyl, quinoxalinyl, quinazolinyl, cinnolinyl, benzopyranyl, benzoxazolyl, furopyridinyl and naphthridinyl. In one embodiment, bicyclic heteroaryl is indolyl.

"Heteroatom" refers to a nitrogen, sulphur, or oxygen atom.

"Heterocyclyl", unless otherwise defined, refers to a saturated or unsaturated ring containing 1 or 2 heteroatoms as member atoms in the ring. However, heterocyclyl rings are not aromatic. In certain embodiments, heterocyclyl is saturated. In other embodiments, heterocyclyl is unsaturated but not aromatic. Heterocyclyl groups containing more than one heteroatom may contain different heteroatoms. In one embodiment, the heterocyclyl groups herein are monocyclic ring systems having 5 or 6 member atoms. Heterocyclyl groups may be optionally substituted with one or more substituents if so defined herein. Monocyclic heterocyclyl includes tetrahydropyranyl, pyrrolidinyl, pyrazolidinyl, imidazolidinyl, isoxazolidinyl, oxazolidinyl, isothiazolidinyl, thiazolidinyl, piperidinyl, piperazinyl, morpholinyl and thiamorpholinyl. In one embodiment, monocyclic heterocyclyl includes pyrrolidinyl, pyrazolidinyl, oxazolidinyl, piperidinyl, piperazinyl and morpholinyl. In another embodiment, heterocyclyl is pyrrolidinyl, piperidinyl, piperazinyl or morpholinyl. In one embodiment the heterocyclyl groups herein are bicyclic systems having 10 member atoms. Bicyclic heterocycyl includes octahydro-4H-1,4-benzoxazinyl and octahydro-2H-pyrido[1,2-a]pyrazinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents if so defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

BINAP 2,2'-Bis(diphenylphosphino)-1,1'-binaphthyl
DCM Dichloromethane
DIPEA Diisopropylethylamine
DMF N,N-Dimethylformamide
DMSO Dimethylsulfoxide
EtOAc Ethyl acetate
g Grams
h or hr Hour(s)
HATU O-(7-Azabenzotriazol-1-yl)-N,N,N',N'-tetramethyluronium hexafluorophosphate
HPLC High performance liquid chromatography
mg Milligrams
LCMS Liquid chromatography/mass spectroscopy
M Molar
MeCN Acetonitrile
MeOH Methanol
mins Minutes
ml or mL Millilitres
mmol Millimoles
MP Macroporous
μl Microlitres
NMR Nucelar Magnetic Resonance
$Pd_2$ $dba_3$ Tris(dibenzylideneacetone)dipalladium(0)

Pd(dppf)Cl$_2$ [1,1'-Bis(diphenylphosphino)ferrocene]dichloropalladium(II)
Pd(PPh$_3$)$_4$ Tetrakis(triphenylphosphine)palladium(0)
Rt or R$_t$ Retention time
SCX Strong Cation Exchange
SPE Solid Phase Extraction
TFA Trifluoroacetic acid
THF Tetrahydrofuran
UPLC Ultrahigh performance liquid chromatography
UV Ultraviolet All references to brine are to a saturated aqueous solution of NaCl.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making or recrystallising the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as 3H, 11C, 14C and 18F.

The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain centers of geometric asymmetry. Where the stereochemistry of a center of geometric asymmetry present in formula (I), or in any chemical structure illustrated herein, is not specified, the structure is intended to encompass the trans geometric isomer, the cis geometric isomer, and all mixtures thereof. Likewise, all tautomeric forms are also included in formula (I) whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to compounds of formula (I) as the free acid or free base. In another embodiment, the invention is directed to compounds of formula (I) and salts thereof. In a further embodiment, the invention is directed to compounds of formula (I) and pharmaceutically acceptable salts thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts impart greater stability or solubility to the molecule thereby facilitating formulation into a dosage form. Accordingly, the invention is further directed to compounds of formula (I) and pharmaceutically acceptable salts thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Process a

Compounds of formula (I) wherein $R^1$, $R^2$ and $R^3$ are as defined above and $R^4$ is hydrogen, and salts thereof, may be prepared by a process comprising deprotection of suitably protected derivatives of compounds of formula (IB). Examples of suitable protection groups and the means of their removal can be found in T. W. Greene and P. G. M. Wuts 'Protective Groups in Organic Synthesis' (3$^{rd}$ Ed., J. Wiley and Sons, 1999).

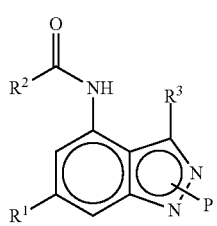

(IB)

As an example of this, compounds of formula (I) may be prepared from compounds of formula (IB) where the indazole ring nitrogen is protected, such as, for example, with 2-tetrahydropyranyl, by deprotecting under appropriate conditions, such as treating with an acid, for example hydrochloric acid.

Compounds of formula (IB), wherein $R^1$, $R^2$ and $R^3$ are as defined above and P is 2-tetrahydropranyl, may be prepared from compounds of formula (II)

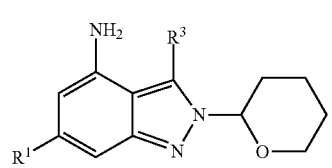

(II)

wherein $R^1$ and $R^3$ are as defined above, by treatment either with (i) a suitable acid of formula $R^2COOH$, wherein $R^2$ is as defined above, followed by deprotection using a suitable acid, or (ii) by treatment with an acid chloride of formula $R^2COCl$, wherein $R^2$ is as defined above, followed by deprotection with a suitable acid. Suitable conditions for (i) include stirring an acid such as, for example, 2-methyl-1,3-thiazole-4-carboxylic acid (commercially available), in a suitable solvent such as N,N-dimethylformamide, at a suitable temperature such as room temperature, for about example 20° C., in the presence of a coupling reagent such as O-(7-azabenzotriazol-1-yl)-N,N,N′N′-tetramethyluronium hexafluorophosphate, in the presence of a suitable base such as N,N-diisopropylethylamine, followed by treatment with a suitable acid such as hydrochloric acid. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C., followed by treatment with a suitable acid such as hydrochloric acid.

Compounds of formula (II) wherein $R^1$ and $R^3$ are as defined above, may be prepared from compounds of formula (III)

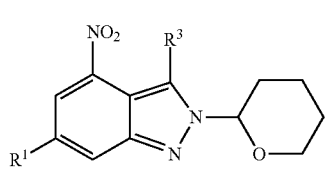

(III)

wherein $R^1$ and $R^3$ are as described above, by hydrogenation in a Thales H-Cube®, in the presence of a suitable catalyst such as palladium on carbon, in a suitable solvent such as ethyl acetate, at a suitable temperature such as 20-40° C., for about example 30° C., at a suitable pressure such as 1-50 bar, for example about 30 bar.

Compounds of formula (III), wherein $R^1$, $R^2$ and $R^3$ are as defined above, may be prepared from compounds of formula (IV)

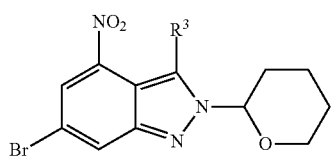

(IV)

wherein R³ is as defined above, by treatment with a suitable boronate ester such as 4-(4,4,5,5-tetramethyl-1,3,2-dioxaborolan-2-yl)-1H-indole, under microwave irradiation, in the presence of a suitable palladium catalyst such as 1,1′-bis(diphenylphosphino)ferrocene palladium dichloride, in a suitable solvent such as 1,4-dioxane and water, in the presence of a suitable base such as sodium carbonate, and at a suitable temperature such as 60-180° C., for example about 150° C.

Compounds of formula (IV) wherein R³ is as defined above, may be prepared from the compound of formula (V) (which is commercially available)

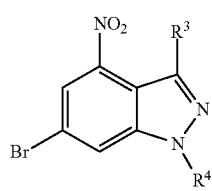

(V)

wherein R³ and R⁴ are H, by treatment with 3,4-dihydro-2H-pyran, with a suitable acid catalyst such as pyridinium p-toluene sulfonate, in a suitable solvent such as dichloromethane, and at a suitable temperature such as reflux temperature.

Process b

Compounds of formula (I) wherein $R^1$, $R^2$, $R^3$ and $R^4$ are as defined above, and salts thereof, may be prepared from compounds of formula (VI)

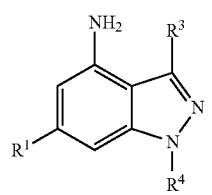

(VI)

wherein $R^1$, $R^3$ and $R^4$ are as defined above, by a process comprising (i) treatment with an acid of formula R²COOH, wherein R² is as defined above, or (ii) treatment with an acid chloride of formula R²COCl, wherein R² is as defined above.

Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N′N′-tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (VI) wherein $R^1$ and $R^3$ are as defined above and $R^4$ is methyl, may be prepared from compounds of formula (VII)

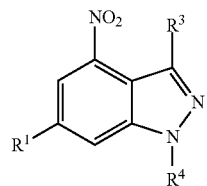

(VII)

wherein $R^1$ and $R^3$ are as defined above and $R^4$ is methyl, by hydrogenation, in the presence of a suitable catalyst such as palladium on carbon, in a suitable solvent such as ethyl acetate, and at a suitable temperature such as room temperature, for example about 20° C.

Compounds of formula (VII) wherein $R^1$ and $R^3$ are as defined above and $R^4$ is methyl, may be prepared from compounds of formula (VIII)

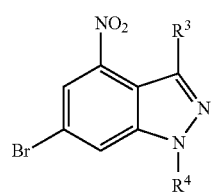

(VIII)

wherein R³ is as defined above and R⁴ is methyl, by treatment with a suitable boronate ester such as 4-(4,4,5,5-tetramethyl-1,3,2-dioxaborolan-2-yl)-1H-indole, under microwave irradiation, in the presence of a suitable palladium catalyst such as 1,1′-bis(diphenylphosphino)ferrocene palladium dichloride, in a suitable solvent such as 1,4-dioxane and water, in the presence of a suitable base such as sodium carbonate, and at a suitable temperature such as 60-180° C., for example about 150° C.

Compounds of formula (VIII) wherein R³ is as defined above and R⁴ is methyl, may be prepared from the compound of formula (V) as described above by treatment with a suitable alkylating agent such as iodomethane, in a suitable solvent such as tetrahydrofuran, in the presence of a suitable base such as sodium hydride, and at a suitable temperature such as between −10-20° C., for example about 0° C.

Compounds of formula (VI) wherein $R^1$, $R^3$ and $R^4$ are as defined above, may also be prepared from the compound of formula (IX) (which is commercially available)

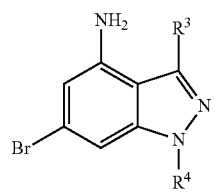

(IX)

wherein R³ and R⁴ are H, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis (diphenylphosphino)ferrocene palladium dichloride, in a suitable solvent such as a mixture of 1,4-dioxane and water, in the presence of a suitable base such as sodium carbonate, at a suitable temperature such as 60-200° C., for example about 115° C. Alternatively, this process may be carried out under microwave irradiation, at a suitable temperature such as 60-200° C., for example about 150° C.

Process c

Compounds of formula (I) wherein $R^1$, $R^2$, $R^3$ and $R^4$ are as defined above, and salts thereof, may be prepared from compounds of formula (X)

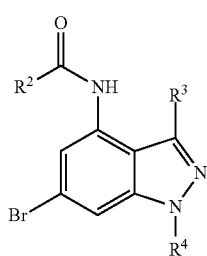

(X)

wherein $R^2$, $R^3$ and $R^4$ are as defined above, by a process comprising treatment with a suitable boronic acid or boronate ester such as 4-(4,4,5,5-tetramethyl-1,3,2-dioxaborolan-2-yl)-1H-indole (commercially available), under microwave irradiation, in the presence of a suitable palladium catalyst such as 1,1'-bis(diphenylphosphino)ferrocene palladium dichloride, in a suitable solvent such as a mixture of 1,4-dioxane and water, in the presence of a suitable base such as sodium carbonate, and at a suitable temperature such as 60-200° C., for example 150° C.

Compounds of formula (X) wherein $R^2$, $R^3$ and $R^4$ are as defined above, may be prepared from compounds of formula (XI)

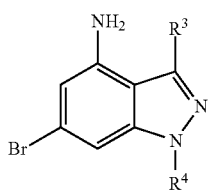

(XI)

wherein $R^3$ and $R^4$ are as defined as above, by (i) treatment with an acid of formula $R^2$COOH, wherein $R^2$ is as defined above, or (ii) by treatment with an acid chloride of formula $R^2$COCl, wherein $R^2$ is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N' tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XI) wherein $R^3$ is as described above and $R^4$ is ethyl, may be prepared from the compound of formula (IX) as described above (which is commercially available) by treatment with a suitable alkylating agent such as iodoethane, in a suitable solvent such as tetrahydrofuran, in the presence of a suitable base such as sodium hydride, and at a suitable temperature, such as between −10-20° C., for example 0° C.

Process d

Compounds of formula (I) wherein $R^1$, $R^2$ and $R^4$ are as defined above and $R^3$ is F, and salts thereof, may be prepared from compounds of formula (XII)

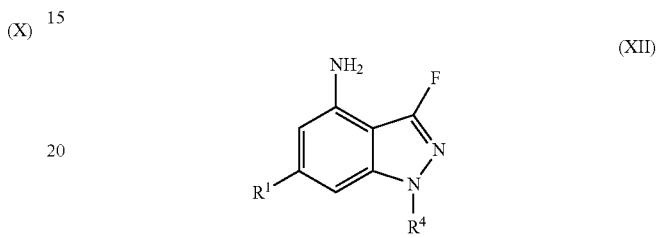

(XII)

wherein $R^1$ and $R^4$ are as defined above, by a process comprising (i) treatment with an acid of formula $R^2$COOH, wherein $R^2$ is as defined above, or (ii) treatment with an acid chloride of formula $R^2$COCl, wherein $R^2$ is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (i) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XII) wherein $R^1$ and $R^4$ are as defined above, may be prepared from compounds of formula (XIII)

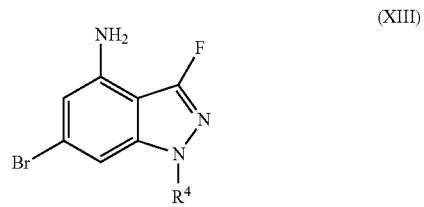

(XIII)

wherein $R^4$ is as defined above, by treatment with a suitable boronic acid or boronate ester such as 4-(4,4,5,5-tetramethyl-1,3,2-dioxaborolan-2-yl)-1H-indole (commercially available), under microwave irradiation, in the presence of a suitable palladium catalyst such as 1,1'-bis(diphenylphosphino) ferrocene palladium dichloride, in a suitable solvent such as a mixture of 1,4-dioxane and water, in the presence of a suitable base such as sodium carbonate, and at a suitable temperature such as 60-200° C., for example about 150° C.

Compounds of formula (XIII) wherein $R^4$ is as defined above, may be prepared from compounds of formula (XIV)

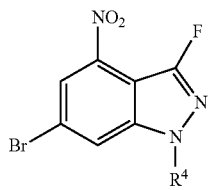

(XIV)

wherein $R^4$ is as described above, by treatment with a suitable reducing agent such as sodium dithionite, in a suitable solvent such as methanol, and at a suitable temperature such as between 0-50° C., for example about 20° C.

Compounds of formula (XIV) wherein $R^4$ is H, may be prepared from the compound of formula (V) as described above, by treatment with a suitable fluorinating agent such as 1-(chloromethyl)-4-fluoro-1,4-diazoniabicyclo[2.2.2]octane (commercially available), under microwave irradiation, in a suitable solvent such as acetonitrile and acetic acid, and at a suitable temperature such as between 80-180° C., for example about 150° C.

Compounds of formula (IB) wherein $R^1$ and $R^3$ are as defined above and $R^2$ is pyridinyl optionally substituted by —$(CH_2)_m NR^6 R^7$, and wherein P is a protecting group, for example benzenesulphonyl, and compounds of formula (I) wherein $R^1$, $R^2$ and $R^3$ are as defined above and $R^4$ is methyl, and salts thereof, may be prepared from compounds of formula (XVA) and (XVB)

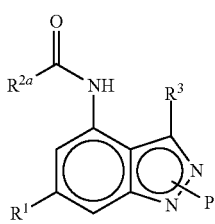

(XVA)

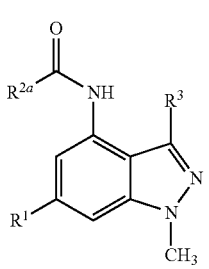

(XVB)

wherein $R^1$ and $R^3$ are as defined above and $R^{2a}$ is pyridinyl optionally substituted by —$(CH_2)_m X$, wherein X is a leaving group such as for example, Cl and wherein P is a protecting group, such as for example benzenesulphonyl, by a process comprising treatment with an amine of formula $NHR^6R^7$ in the presence of a suitable base such as DIPEA, a suitable activating agent such as sodium iodide and in a suitable solvent such as acetonitrile, heating to a suitable temperature such as 20° C.-120° C., for example about 70° C.

As the skilled person will appreciate, in the compound of formula (XVA), the protecting group P may be on the 1 or 2 position of the indazole.

Compounds of formula (XVA) and (XVB) wherein $R^1$ and $R^3$ are as defined above and $R^{2a}$ is pyridinyl optionally substituted by —$(CH_2)_m X$, wherein X is a leaving group such as Cl and wherein P is a protecting group, for example benzenesulphonyl, may be prepared from compounds of formula (XVIA) and (XVIB)

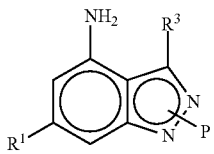

(XVIA)

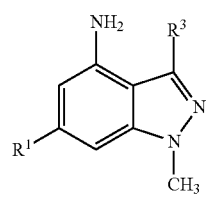

(XVIB)

wherein $R^1$ and $R^3$ are as defined above, by a process comprising treatment with an acid chloride of formula $R^{2a}COCl$, wherein $R^{2a}$ is as defined above, in the presence of a suitable base such as pyridine, in a suitable solvent such as DCM, and at a suitable temperature such as room temperature.

Compounds of formula $R^{2a}COCl$ wherein $R^{2a}$ is as defined above, can be prepared from compounds of formula $R^{2a}CO_2H$ wherein $R^{2a}$ is as defined above, by treatment with thionyl chloride in a suitable solvent such as chloroform, in the presence of DMF (catalytic quantity) and heating to a suitable temperature such as reflux.

Thus, in one embodiment, the invention provides a a process for preparing a compound of the invention comprising:

a) deprotection of a suitably protected derivative of a compound of formula (IB)

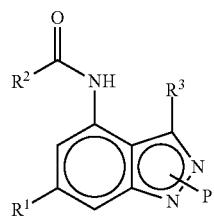

(Ia)

wherein $R^1$, $R^2$, $R^3$ and $R^4$ are as defined above;

b) reacting a compound of formula (VI)

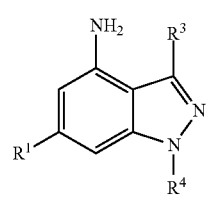

(VI)

wherein $R^1$, $R^3$ and $R^4$ are as defined above, with (i) an acid of formula $R^2COOH$, wherein $R^2$ is as defined above, or (ii) an acid chloride of formula $R^2COCl$, wherein $R^2$ is as defined above;

c) reacting a compound of formula (X)

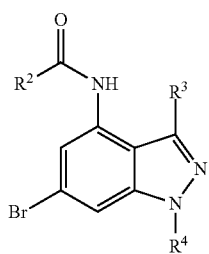

(X)

wherein $R^2$, $R^3$ and $R^4$ are as defined above, with a suitable boronic acid or boronate ester; or d) for a compound of formula (I) wherein $R^1$, $R^2$ and $R^4$ are as defined above and $R^3$ is F, or a salt thereof, reacting a compound of formula (XII)

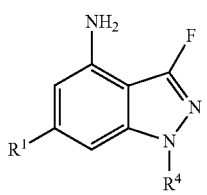

(XIII)

wherein $R^1$ and $R^4$ are as defined above, with (i) an acid of formula $R^2COOH$, wherein $R^2$ is as defined above, or (ii) an acid chloride of formula $R^2COCl$, wherein $R^2$ is as defined above.

e) for a compound of formula (I) wherein $R^1$, $R^3$ and $R^4$ are as defined above and $R^2$ is pyridinyl optionally substituted by $-(CH_2)_mNR^6R^7$, and salts thereof, reacting a compound of formula (XVA) or (XVB)

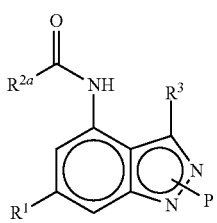

(XVA)

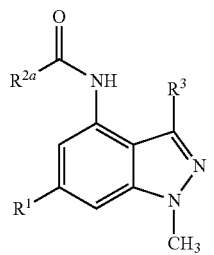

(XVB)

wherein $R^1$ and $R^3$ are as defined above and $R^{2a}$ is pyridinyl optionally substituted by $-(CH_2)_{mq}X$, wherein X is a leaving group, and wherein P is a protecting group, with an amine of formula $NHR^6R^7$, followed where necessary by deprotection.

Methods of Use

The compounds of the invention are inhibitors of PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally. Preferably, the compounds of formula (I) or pharmaceutically acceptable salts thereof are administered by inhalation.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate PI3-kinase activity comprising administering a safe and effective amount of a compound of formula (I) or a pharmaceutically acceptable salt thereof to a patient in need thereof.

In one embodiment, the disorder mediated by inappropriate PI3-kinase activity is selected from the group consisting of respiratory diseases (including asthma and chronic obstructive pulmonary disease (COPD)); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trama), trigeminal neuralgia and central pain).

In one embodiment, the disorder mediated by inappropriate PI3-kinase activity is a respiratory disease. In a further embodiment, the disorder mediated by inappropriate PI3-kinase activity is asthma. In a further embodiment, the disorder mediated by inappropriate PI3-kinase activity is chronic obstructive pulmonary disease (COPD).

In one embodiment, the disorder mediated by inappropriate PI3-kinase activity is pain.

In one embodiment, the invention provides a compound of formula (I) or a pharmaceutically acceptable salt thereof for use in medical therapy. In another embodiment, the invention provides a compound of formula (I) or a pharmaceutically acceptable salt thereof for use in the treatment of a disorder mediated by inappropriate PI3-kinase activity. In a further embodiment, the invention provides the use of a compound of formula (I) or a pharmaceutically acceptable salt thereof in the manufacture of a medicament for use in the treatment of a disorder mediated by inappropriate PI3-kinase activity.

Compositions

The compounds of formula (I) and pharmaceutically acceptable salts thereof will normally, but not necessarily, be formulated into pharmaceutical compositions prior to administration to a patient. Accordingly, in another aspect the invention is directed to pharmaceutical compositions comprising a compound of formula (I) or a pharmaceutically acceptable salt thereof and one or more pharmaceutically-acceptable excipients.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when comingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable e.g. of sufficiently high purity.

The compound of formula (I) or a pharmaceutically acceptable salt thereof and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration. Preferably, the compounds of formula (I) or pharmaceutically acceptable salts thereof will be formulated for inhaled administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example, as a dry powder, an aerosol, a suspension, or a solution composition. Preferably, the invention is directed to a dry powder composition adapted for inhalation comprising compound of formula (I) or a pharmaceutically acceptable salt thereof.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminum or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminum can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example of a bulk manufacturing method for preparing solution aerosol formulations, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a β₂-adrenoreceptor agonist, an antiinfective agent, such as an antibiotic or an antiviral, or an antihistamine. One embodiment of the invention encompasses combinations comprising a compound of formula (I) or a pharmaceutically acceptable salt thereof together with a β₂-adrenoreceptor agonist, and/or an anticholinergic, and/or a PDE-4 inhibitor, and/or an antihistamine.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a β₂-adrenoreceptor agonist.

Examples of β₂-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting β₂-adrenoreceptor agonists, for example, compounds which provide effective bronchodilation for about 12 hrs or longer, are preferred.

Other β₂-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of β₂-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The β₂-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid. Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;

3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., J. Med. Chem. 46:3957-3960 (2003).

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

In a preferred aspect, the invention provides a combination comprising a compound of formula (I) or a pharmaceutically acceptable salt thereof together with a corticosteroid.

In a further preferred aspect, the invention provides a combination comprising a compound of formula (I) or a pharmaceutically acceptable salt thereof together with a $\beta_2$-adrenoreceptor agonist.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

In a preferred aspect, the invention provides a pharmaceutical composition comprising a combination of a compound of formula (I) or a pharmaceutically acceptable salt thereof together with a corticosteroid.

In a further preferred aspect, the invention provides a pharmaceutical composition comprising a combination of a compound of formula (I) or a pharmaceutically acceptable salt thereof together with a $\beta_2$-adrenoreceptor agonist.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

General Methods

LCMS (Liquid Chromatography Mass Spectroscopy)

LCMS analysis has been carried out using one of the methods listed below.

LCMS Method A

Waters ZQ mass spectrometer operating in positive ion electrospray mode, mass range 100-1000 amu.
UV wavelength: 215-330 nm
Column: 3.3 cm×4.6 mm ID, 3 µm ABZ+PLUS
Flow Rate: 3 ml/min
Injection Volume: 5 µl
Solvent A: 95% acetonitrile+0.05% of a 1% v/v solution of formic acid in water
Solvent B: 0.1% v/v solution of formic acid in 10 mM aqueous ammonium acetate
Gradient: Mixtures of Solvent A and Solvent B are used according to the following gradient profiles (expressed as % Solvent A in the mixture): 0% A/0.7 min, 0-100% A/3.5 min, 100% A/0.4 min, 100-0% A/0.2 min LCMS Method B LCMS instrumentation consists of the following:
Column: Acquity HPLC BEH $C_{18}$ 1.7 µm 2.1 mm×50 mm. Column oven set to 40 degrees centigrade
Solvent A: Water 0.1% Formic Acid+10 mM Ammonium Acetate
Solvent B: MeCN:Water 95:5+0.05% Formic Acid
Injection volume: 0.5 µl
Injection technique: Partial loop overfill
UV detection: 220 to 330 nm
UV sampling rate: 40 points per second
MS scan range: 100 to 1000 amu
MS scanning rate: 0.2 second scan with a 0.1 second inter scan delay
MS scan function: Electrospray with pos neg switching
Cycle time: 2 minutes and 30 seconds
Gradient:

| Time | Flow ml/min | % A | % B |
|------|-------------|-----|-----|
| 0    | 1           | 97  | 3   |
| 0.1  | 1           | 97  | 3   |
| 1.4  | 1           | 0   | 100 |
| 1.9  | 1           | 0   | 100 |
| 2    | 1           | 97  | 3   |

LCMS Method C

The HPLC analysis was conducted on a Sunfire C18 column (30 mm×4.6 mm i.d. 3.5 µm packing diameter) at 30 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
|------------|--------------------|-----|-----|
| 0          | 3                  | 97  | 3   |
| 0.1        | 3                  | 97  | 3   |
| 4.2        | 3                  | 0   | 100 |
| 4.8        | 3                  | 0   | 100 |
| 4.9        | 3                  | 97  | 3   |
| 5.0        | 3                  | 97  | 3   |

The UV detection was an averaged signal from wavelength of 210 nm to 350 nm and mass spectra were recorded on a mass spectrometer using alternate-scan positive and negative mode electrospray ionization.

Mass Directed Automated Preparative HPLC

The methods for the Mass Directed Automated Preparative HPLC used for the purification of compounds are described below:

Mass Directed Automated Preparative HPLC Column, Conditions and Eluent

Method A

Column

The column used is typically a Supelco LCABZ++ column whose dimensions are 20 mm internal diameter by 100 mm in length. The stationary phase particle size is 5 µm.

Solvents

A: Aqueous solvent=Water+0.1% Formic Acid
B: Organic solvent=MeCN:Water 95:5+0.05% Formic Acid
Make up solvent=MeOH:Water 80:20+50 mMol Ammonium Acetate
Needle rinse solvent=MeOH: Water:DMSO 80:10:10

Methods

There are five methods used depending on the analytical retention time of the compound of interest. They all have a 15-minute runtime, which comprises of a 10-minute gradient followed by a 5-minute column flush and re-equilibration step.
compound retention time 1.5-2.2 mins=0-30% B
compound retention time 2.0-2.8 mins=5-30% B
compound retention time 2.5-3.0 mins=15-55% B
compound retention time 2.8-4.0 mins=30-80% B
compound retention time 3.8-5.5 mins=50-90% B
Flow Rate
　All of the above methods have a flow rate of 20 ml/min
　It is thought that basic compounds isolated by this method are formate salts.
Mass Directed Automated Preparative HPLC Column, Conditions and Eluent
Method B
Columns
Small Scale Prep Column
　Supelcosil ABZ+Plus column whose dimensions are 21.2 mm internal diameter by 100 mm in length. The stationary phase particle size is 5 μm.
Large Scale Prep Column
　Supelcosil ABZ+Plus column whose dimensions are 30.0 mm internal diameter by 150 mm in length. The stationary phase particle size is 12 μm.
Solvents
A: Aqueous solvent=Water+0.1% Formic Acid
B: Organic solvent=MeCN:Water 95:5+0.05% Formic Acid
　Make up solvent to ZQ=MeOH:Water 80:20+50 mMol Ammonium Acetate 2767 Needle rinse solvent=MeOH:Water:DMSO 80:10:10
Methods for Small Scale Prep for up to 30 mg
　There are ten methods available for use. The choice of method is dependant on the analytical retention time of the compound of interest.
　Five methods have a 15-minute runtime, this comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.
compound retention time 1.5-2.2 mins=00-30% B
compound retention time 2.0-2.8 mins=10-40% B
compound retention time 2.5-3.0 mins=15-55% B
compound retention time 2.8-4.0 mins=30-80% B
compound retention time 3.8-5.5 mins=60-90% B
　Flow rates for the above methods are 20 ml/min
Methods for Large Scale Prep for up to 90 mgs
　Due to the different column dimension and the phase particle size the percentage organic content varies slightly to the small scale methods. As for small scale there are ten methods available for use. The choice of method is dependant on the analytical retention time of the compound of interest.
　Five methods have a 15-minute runtime, which comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.
compound retention time 1.5-2.2 mins=00-30% B
compound retention time 2.0-2.8 mins=10-40% B
compound retention time 2.5-3.0 mins=25-55% B
compound retention time 2.8-4.0 mins=40-75% B
compound retention time 3.8-5.5 mins=60-90% B
　Flow rates for the above methods are 40 ml/min
　It is thought that basic compounds isolated by this method are formate salts.
Mass Directed Automated Preparative HPLC Column, Conditions and Eluent
Method C
　Column details: Zorbax Eclipse XDB-C18 prep HT (dimensions 212×100 mm, 5 um packing)
　Software/hardware: Agilent 1100 series LCMSD hardware, chemstation 32 purification software
Solvents:
A=0.1% v/v solution of Trifluoroacetic Acid in Water.
B=0.1% v/v solution of Trifluoroacetic Acid in Acetonitrile.
　20 ml/min solvent speed, gradient elution:
1 min 90% Water (0.1% TFA):10% MECN (0.1% TFA) increasing over 9 mins to 5% Water (0.1% TFA):95% MECN (0.1% TFA) to elute compounds,
or 1 min 70% Water (0.1% TFA):30% MECN (0.1% TFA) increasing over 9 mins to 5% Water (0.1% TFA):95% MECN (0.1% TFA) to elute compounds.
　Collects on uv or uv/mass ion trigger
Mass Directed Automated Preparative HPLC Column, Conditions and Eluent
Method D
　Column Details: XBRIDGE C18 column (100 mm×19 mm id 5 uM packing diameter)
Solvents
A=10 mM ammonium bicarbonate in water adjusted to pH 10 with aq. ammonia solution
B=Acetonitrile
　The UV detection was an averaged signal from wavelength of 210 nm to 350 nm and mass spectra were recorded on a mass spectrometer using an alternate-scan positive and negative mode electrospray ionization.
Mass Directed Automated Preparative HPLC Column, Conditions and Eluent
Method E
　Mass Directed Auto Prep System consists of:
Waters ZQ Mass spectrometer
Waters 2525 pump
Waters Reagent Manager
Waters 2767 autosampler
Gilson 202 autosampler
Gilson 115 UV detector
Splitter Box
Phenomenex column switcher
Injection volume: 0.5 ml
Flow rate (mobile phase): 20 ml/minute
Column: Supelco ABZ+plus 100 mm×21.2 mm, 5 um
　Mobile Phase: A) 0.1% v/v solution of formic acid in water.
　B) 95% acetonitrile+5% of a 1% v/v solution of formic acid in water.
　Make up Flow: 80% methanol+20% 0.1% v/v solution of formic acid in 10 mM aqueous ammonium acetate.
　Two injections per sample were made on the generic methods 2.5-3.0 and 2.8-4.0.
Gradient

| Time (minutes) | 2.5-3.0% B | 2.8-4.0% B |
|---|---|---|
| 0 | 15 | 30 |
| 1 | 15 | 30 |
| 10 | 55 | 85 |
| 14 | 99 | 99 |
| 14.8 | 99 | 99 |
| 15 | 15 | 30 |

Mass Directed Automated Preparative HPLC Column, Conditions and Eluent

Method F

Column Details: SUNFIRE C18 column (100 mm×19 mm id 5 uM packing diameter)

The solvents employed were:
A=0.1% v/v solution of Trifluoroacetic Acid in Water.
B=0.1% v/v solution of Trifluoroacetic Acid in Acetonitrile.

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Intermediates and Examples

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

Similarly, when a literature or a patent reference is given after the name of a compound, for instance compound Y (EP 0 123 456), this means that the preparation of the compound is described in the named reference.

The names of the Examples have been obtained using a compound naming programme which matches name to structure (e.g. ACD/Name Batch v 9.0).

Intermediate 1

6-Bromo-4-nitro-2-(tetrahydro-2H-pyran-2-yl)-2H-indazole

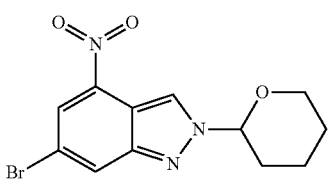 [SMILES: O=[N+]([O-])c1cc(Br)cc2nn(C3CCCCO3)cc12]

A mixture of 6-bromo-4-nitro-1H-indazole (available from Sinova, 10 g, 0.041 mol), 3,4-dihydro-2H-pyran (7.85 g, 8.52 ml, 0.093 mol) and pyridine 4-methylbenzenesulfonate (0.125 g, 0.496 mol) in dichloromethane (150 ml) was heated at reflux for 4.5 hours. The reaction was allowed to cool to room temperature and was poured onto saturated aqueous sodium bicarbonate (200 ml). The layers were separated and the aqueous layer extracted with dichloromethane (2×100 ml). The combined organic layers were washed with 5% aqueous citric acid (w/v, 100 ml) and brine (100 ml) and dried over magnesium sulphate. Solvent was removed in vacuo to give the title compound (12.9 g) as a dark orange solid.

LCMS (Method A) $R_t$=3.42 mins, MH$^+$=328.

Intermediate 2

6-(1H-Indol-4-yl)-4-nitro-2-(tetrahydro-2H-pyran-2-yl)-2H-indazole

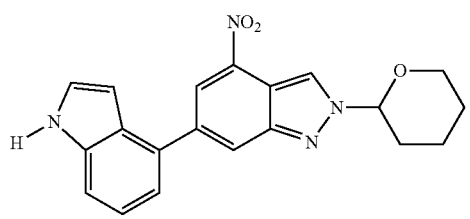

Five reactions were set up with 6-bromo-4-nitro-2-(tetrahydro-2H-pyran-2-yl)-2H-indazole (500 mg, 1.53 mmol), [1,1'-bis(diphenylphosphino)ferrocene]dichloropalladium (II) (125 mg, 0.153 mmol), 1H-indol-4-ylboronic acid (370 mg, 2.3 mmol), saturated aqueous sodium hydrogen carbonate (3 ml) and isopropyl alcohol (12 ml) in each. They were all heated at 150° C. for 10 minutes in the microwave. The reaction mixtures were combined and water (250 ml) and ethyl acetate (250 ml) added. The mixture was filtered and the organic layer collected. The organic layer was washed with water followed by brine. The organic layer was dried over magnesium sulphate, filtered and solvent removed in vacuo. The residue was dissolved in dichloromethane and pre-absorbed onto silica. Purification was carried out using chromatography on silica eluting with 0-25% ethyl acetate in cyclohexane. The desired fractions were collected and combined and solvent removed in vacuo to give the title compound as a yellow solid (1.72 g).

LCMS (Method A) m/z 363 [MH$^+$], $R_t$=3.61 min.

Intermediate 3

6-(1H-Indol-4-yl)-2-(tetrahydro-2H-pyran-2-yl)-2H-indazol-4-amine

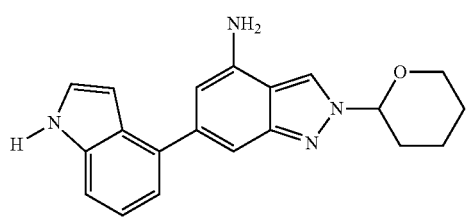 [SMILES: Nc1cc(-c2cccc3[nH]ccc23)cc2nn(C3CCCCO3)cc12]

6-(1H-Indol-4-yl)-4-nitro-2-(tetrahydro-2H-pyran-2-yl)-2H-indazole (714 mg, 1.97 mmol) was dissolved in ethyl acetate (100 ml) and the compound was hydrogenated using the H-cube® (available from THALESNano) using 10% Pd/C catalyst at 30° C. and under 30 bar pressure of hydrogen. Solvent was removed in vacuo to give the title compound (629 mg) as an orange/brown solid.

LCMS (Method A) $R_t$=2.86 mins, MH$^+$=333.

Intermediate 4

6-(1H-Indol-4-yl)-1H-indazol-4-amine

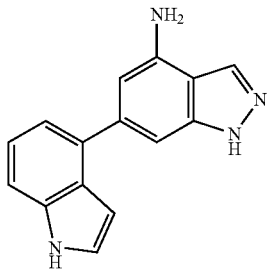 [SMILES: Nc1cc(-c2cccc3[nH]ccc23)cc2[nH]ncc12]

6-Bromo-1H-indazol-4-amine (available from Sinova, 10.0 g, 47.2 mmol) and 4-(4,4,5,5-tetramethyl-1,3,2-dioxaborolan-2-yl)-1H-indole (available from Frontier Scientific, Europe Ltd, 16.05 g, 66.0 mmol) were dissolved in 1,4-dioxane (60 ml) and water (60 ml). Sodium carbonate solution (2 M, 70.7 ml) and Pd(dppf)Cl$_2$-DCM adduct (1.926 g, 2.36 mmol) were added and the mixture was heated at 115° C. for 18 hr. The reaction mixture was diluted with dichloromethane (200 ml) and the organic and aqueous layers were separated by hydrophobic frit. The aqueous layer was extracted with further quantities of dichloromethane (2×200 ml), using a hydrophobic frit to separate the layers. The organic layers were combined and silica (80 g) was added. The solvent was removed in vacuo to give a crude material which was purified by chromatography on silica gel (750 g cartridge, Flashmaster II) eluting with 0-100% ethyl acetate in cyclohexane over 60 minutes. The oil was dried in vacuo on a drying rack overnight. The yellow foam was dissolved in dichloromethane (3×400 ml), removing the solvent in vacuo after each dissolution. ethyl acetate (50 ml) was then added and the solvent was removed in vacuo. The solid obtained was dried in a vacuum oven to give the title compound (12.8 g) as a yellow foam.

LCMS (Method A) R$_t$=2.71 mins, MH$^+$=249.

Intermediate 5

6-Bromo-1-ethyl-1H-indazol-4-amine

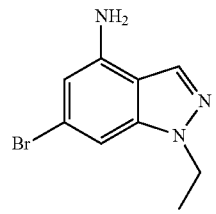

To a solution of 6-bromo-1H-indazol-4-amine (available from Sinova, 300 mg, 1.41 mmol) in THF (7 ml), cooled to 0° C. was added 60% sodium hydride in mineral oil (62 mg, 1.55 mmol) and the reaction was stirred for 15 mins. Iodoethane (0.124 ml, 1.55 mmol) was added and the reaction was stirred overnight. The reaction was quenched with MeOH (1 ml), diluted with water (10 ml), then extracted into ethyl acetate, which was separated and evaporated to dryness. The residue was purified by silica chromatography using 0-100% ethyl acetate in cyclohexane over 80 mins. Pure fractions were evaporated to give the title compound (110 mg).

LCMS (Method B) R$_t$=0.99 mins, MH$^+$=281.

Intermediate 6

N-(6-Bromo-1-ethyl-1H-indazol-4-yl)-6-methyl-2-pyridinecarboxamide

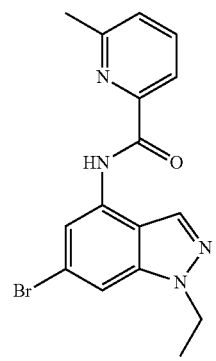 [SMILES: CCn1ncc2c(NC(=O)c3cccc(C)n3)cc(Br)cc21]

DIPEA (0.161 ml, 0.93 mmol) was added to 6-methyl-2-pyridinecarboxylic acid (available from Fluorochem, 51 mg, 0.37 mmol) and O-(7-azabenzotriazol-1-yl)-1,1,3,3-tetramethyluronium hexafluorophosphate (174 mg, 0.46 mmol) in DMF (3 ml). The reaction was stirred for 30 mins under nitrogen then 6-bromo-1-ethyl-1H-indazol-4-amine (100 mg, 0.42 mmol) was added and the reaction was stirred overnight. The solvent was evaporated and water (5 ml) was added before extraction into DCM (2×20 ml). The compound was loaded onto an aminopropyl cartridge (20 g), eluted with 10% MeOH in DCM and evaporated to dryness. The residue was purified by silica chromatography, eluting with 0-50% ethyl acetate in DCM over 60 mins. Appropriate fractions were evaporated to give the title compound (107 mg).

LCMS (Method B) R$_t$=1.32 mins, MH$^+$=361.

Intermediate 7

6-Bromo-1-methyl-4-nitro-1H-indazole

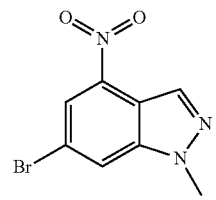

6-Bromo-4-nitro-1H-indazole (available from Sinova, 1.05 g, 4.13 mmol) was dissolved in THF (20 ml) and cooled to 0° C. under nitrogen. 60% Sodium hydride in mineral oil (191 mg, 7.57 mmol) was added portion-wise allowing the evolution of gas to subside before adding the next portion. This was left under nitrogen, stirring at 0° C. for 15 mins. Iodomethane (0.298 ml, 4.78 mmol) in THF (5 ml) was added dropwise to the reaction, washing through with further THF (5 ml). The reaction was then allowed to warm to room temperature. The reaction was stirred for 5 h then partitioned between ethyl acetate and water, washing the water with ethyl acetate (x3). The combined organics were washed with brine, dried over magnesium sulphate, filtered and evaporated to dryness. The residue was purified by silica chromatography using a gradient of 0-25% ethyl acetate in cyclohexane, to give the title compound (388 mg).

LCMS (Method B) $R_t$=1.08, no ionisation. $^1$H NMR: (400 MHz, d$^6$-DMSO) δ ppm 8.61 (1H, s), 8.47 (1H, s), 8.20 (1H, s), 4.15 (3H, s).

Intermediate 8

6-(1H-Indol-4-yl)-1-methyl-4-nitro-1H-indazole

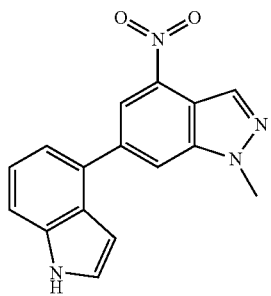 [SMILES: Cn1ncc2c([N+](=O)[O-])cc(-c3cccc4[nH]ccc34)cc21]

6-Bromo-1-methyl-4-nitro-1H-indazole (100 mg, 0.39 mmol), Pd(dppf)Cl$_2$ (32 mg, 0.04 mmol) and 1H-indol-4-ylboronic acid (94 mg, 0.59 mmol) were treated with a 4:1 mixture of propan-2-ol and saturated sodium bicarbonate solution (3 ml) and the reaction was heated in a microwave at 150° C. for 10 mins. Ethyl acetate was added, a solid was filtered off and the filtrate was partitioned between ethyl acetate and water. The water was washed twice with ethyl acetate and the combined organics were washed with brine, dried over magnesium sulphate, filtered and evaporated. The residue was purified by silica chromatography, eluting with 0-25% ethyl acetate in cyclohexane. Appropriate fractions were combined and evaporated to give the title compound (49 mg) as an orange solid.

LCMS (Method A) $R_t$=3.42 mins, MH$^+$=293.

Intermediate 9

6-(1H-Indol-4-yl)-1-methyl-1H-indazol-4-amine

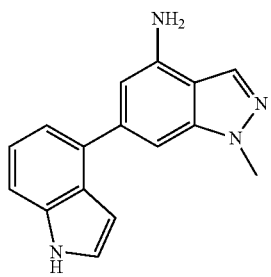 [SMILES: Cn1ncc2c(N)cc(-c3cccc4[nH]ccc34)cc21]

6-(1H-Indol-4-yl)-1-methyl-4-nitro-1H-indazole (49 mg, 0.17 mmol) was dissolved in ethyl acetate (10 ml) and treated with 10% Pd/C (5 mg) then stirred under hydrogen for 2 h before stirring under nitrogen over the weekend. The reaction was filtered through a Celite cartridge, washing with ethyl acetate, then evaporated to dryness to give the title compound (70 mg) as a grey solid.

LCMS (Method A) $R_t$=2.82 mins, MH$^+$=263.

Intermediate 10

6-[(Dimethylamino)methyl]-2-pyridinecarboxylic acid

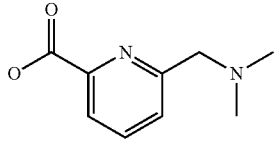

To a solution of 6-formyl-2-pyridinecarboxylic acid (available from Chemstep Product List, 250 mg, 1.65 mmol) in dichloromethane (4.6 ml) was added dimethylamine (2M solution in THF, 2.17 ml, 4.34 mmol) and acetic acid (0.083 ml). The mixture was stirred at room temperature for 15 mins when sodium triacetoxyborohydride (459 mg, 2.17 mmol) was added and the mixture stirred overnight. The reaction mixture was quenched by the addition of a few drops of methanol. The mixture was loaded onto an aminopropyl-SPE cartridge (5 g) pre-eluted with dichloromethane, which was eluted with dichloromethane followed by methanol. Fractions containing product were combined and dried under vacuum. The crude product was taken up in sodium hydroxide solution (2M, 25 ml) and washed with dichloromethane (2×25 ml). The aqueous layer was acidified to pH7 using hydrochloric acid (5M) and concentrated under vacuum to approximately 25 ml. The solution was loaded onto an Oasis cartridge (6 g), which had been pre-eluted with methanol (1 volume) followed by water (1 volume). The cartridge was eluted with water (1 volume) followed by methanol. Fractions containing product were combined and dried to give the title compound (85 mg).

LCMS (Method B) $R_t$=0.25 mins, MH$^+$=181.

Intermediate 11

6-(4-Morpholinylmethyl)-2-pyridinecarboxylic acid

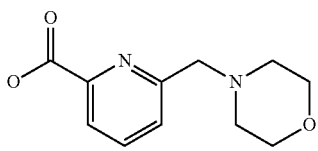 [SMILES: O=C(O)c1cccc(CN2CCOCC2)n1]

To a solution of 6-formyl-2-pyridinecarboxylic acid (available from Chemstep Product List, 250 mg, 1.65 mmol) in dichloromethane (6.8 ml) was added morpholine (0.377 ml, 4.31 mmol) and acetic acid (0.083 ml). The mixture was stirred at room temperature for 15 min when sodium triacetoxyborohydride (459 mg, 2.17 mmol) was added and the mixture stirred overnight. The crude reaction mixture was diluted with dichloromethane (10 ml) and methanol was added until a clear solution was observed. The mixture was loaded onto an aminopropyl cartridge (5 g) pre-eluted with dichloromethane. The cartridge was eluted with dichloromethane followed by methanol and fractions containing product were combined and blown to dryness under a stream of nitrogen. The crude product was taken up in sodium hydroxide solution (2M, 25 ml) and washed with dichloromethane (2×25 ml). The aqueous layer was acidified to pH7 using hydrochloric acid (5M) and concentrated under vacuum to approximately 25 ml. The solution was loaded onto an Oasis cartridge (6 g), which had been pre-eluted with methanol (1 volume) followed by water (1 volume). The cartridge was eluted with water (1 volume) followed by methanol. Fractions containing product were combined and dried to give the title compound (129 mg).

LCMS (Method B) $R_t$=0.26 mins, MH$^+$=223.

Intermediate 12

6-(1-Piperidinylmethyl)-2-pyridinecarboxylic acid

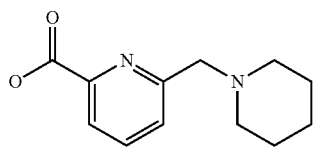 [SMILES: O=C(O)c1cccc(CN2CCCCC2)n1]

To a solution of 6-formyl-2-pyridinecarboxylic acid (available from Chemstep Product List, 250 mg, 1.65 mmol) in dichloromethane (5.8 ml) was added piperidine (0.428 ml, 4.33 mmol) and acetic acid (0.083 ml). The mixture was stirred at room temperature for 30 mins when sodium triacetoxyborohydride (459 mg, 2.17 mmol) was added and the mixture stirred for 45 mins. The mixture was loaded onto an aminopropyl cartridge (5 g) pre-eluted with dichloromethane. The cartridge was eluted with dichloromethane and methanol, and fractions containing product were combined and blown to dryness under a stream of nitrogen. The crude product was taken up in ethyl acetate (25 ml) and washed with sodium hydroxide solution (2M, 3×25 ml). The aqueous layer was acidified to pH6 using hydrochloric acid (5M) and concentrated under vacuum to approximately 25 ml. The solution was loaded onto an Oasis cartridge (6 g), which had been pre-eluted with methanol (1 volume) followed by water (1 volume). The cartridge was eluted with water (1 volume) followed by methanol. Fractions containing product were combined and dried to give the title compound (376 mg).

LCMS (Method B) $R_t$=0.44 mins, MH$^+$=221.

Intermediate 13

6-[(4-Methyl-1-piperazinyl)methyl]-2-pyridinecarboxylic acid

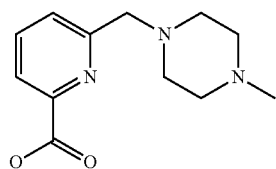 [SMILES: CN1CCN(Cc2cccc(C(=O)O)n2)CC1]

To a solution of 6-formyl-2-pyridinecarboxylic acid [Chemstep Product List] (0.25 g) in dichloromethane (6.8 ml) was added 1-methylpiperazine (0.481 ml) and acetic acid (0.083 ml). The mixture was stirred at room temperature for 15 min when sodium triacetoxyborohydride (0.459 g) was added and the mixture stirred overnight. The crude reaction mixture was diluted with dichloromethane (60 ml) and methanol was added until a clear solution was observed. The mixture was loaded onto an aminopropyl-SPE cartridge (5 g) pre-eluted with dichloromethane. The cartridge was eluted with dichloromethane and methanol and fractions containing product were combined and blown to dryness under a stream of nitrogen. The crude product was taken up in dichloromethane (2×25 ml) and washed with 2M sodium hydroxide solution (25 ml). The aqueous layer was acidified to pH7 using 5N hydrochloric acid and concentrated under vacuum to approximately 25 ml. The solution was loaded onto an Oasis cartridge (6 g) and eluted with water (one volume) and methanol. Fractions containing product were combined and dried to give the title compound (0.171 g).

LCMS (Method B): m/z 236 [MH$^+$], $R_t$=0.25 min.

Intermediate 14

6-Chloro-3-fluoro-N-[6-(1H-indol-4-yl)-1H-indazol-4-yl]-2-pyridinecarboxamide

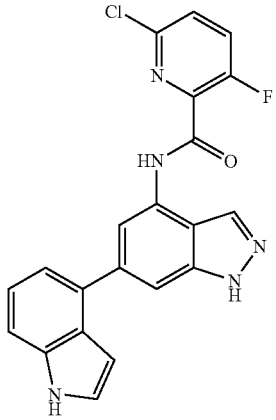 [SMILES: O=C(Nc1cc(-c2cccc3[nH]ccc23)cc2[nH]ncc12)c1nc(Cl)ccc1F]

To a solution of 6-fluoro-3-chloro-2-pyridinecarboxylic acid (available from Asymchem Laboratories, 848 mg, 4.83 mmol) in DMF (15 ml) was added O-(7-azabenzotriazol-1-yl)-1,1,3,3-tetramethyluronium hexafluorophosphate (1838 mg, 4.84 mmol) and DIPEA (2.53 ml). The mixture was stirred at room temperature for 30 mins then 6-(1H-indol-4-yl)-1H-indazol-4-amine (600 mg, 2.42 mmol) was added and the mixture stirred at room temperature for 36 h. The reaction mixture was concentrated in vacuo to 5 ml which was added to 2×50 g aminopropyl cartridges that had been preconditioned with methanol. The reaction mixture remained on the cartridges for 2 h before being eluted with methanol. The mixture was concentrated in vacuo and a precipitate formed, which was collected by filtration to give the title compound (531 mg) as a yellow solid.

LCMS (Method B) $R_t$=1.02 mins, MH$^+$=406.

Intermediate 15

N-(6-Bromo-1H-indazol-4-yl)-2-pyridinecarboxamide

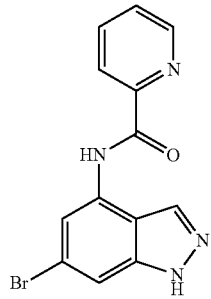 [SMILES: O=C(Nc1cc(Br)cc2[nH]ncc12)c1ccccn1]

A mixture of 6-bromo-1H-indazol-4-amine (available from Sinova, 100 mg, 0.47 mmol), 2-pyridinecarbonyl chloride hydrochloride (available from Apollo, 100 mg, 0.71 mmol), DIPEA (0.164 ml) in DCM (10 ml) was stirred at room temperature overnight. The reaction mixture was concentrated in vacuo. Purification by Mass Directed Automated Preparative HPLC (Method B) gave after evaporation of solvents the title compound (38 mg) as a white solid. LCMS (Method B) $R_t$=0.97 mins, MH$^+$=318.

Intermediate 16

6-Bromo-1-methyl-1H-indazol-4-amine

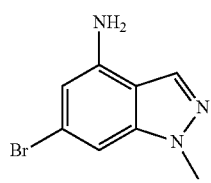

6-Bromo-1H-indazol-4-amine (available from Sinova, 300 mg, 1.42 mmol) was dissolved in THF (7.5 ml) and the mixture cooled to 0° C. Sodium hydride (62 mg, 1.56 mmol) was then slowly added. The mixture was stirred for 15 minutes, then methyl iodide (221 mg, 1.56 mmol) was added and stirring continued at 0° C. for 3 h. The reaction mixture was quenched by careful addition of methanol (2 ml), then water (10 ml), then extracted into ethyl acetate and the organic layer was concentrated in vacuo. The residue was purified by column chromatography on silica eluting with a gradient of 0-50% ethyl acetate in cyclohexane. Fractions containing desired product were combined and concentrated in vacuo to afford the title compound (48 mg).

LCMS (Method B): $R_t$=0.91 mins, MH$^+$=227

Intermediate 17

N-(6-Bromo-1-methyl-1H-indazol-4-yl)-6-methyl-2-pyridinecarboxamide

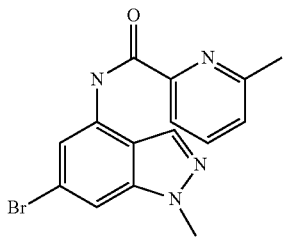 [SMILES: Cc1cccc(C(=O)Nc2cc(Br)cc3c2cnn3C)n1]

6-Methyl-2-pyridinecarboxylic acid (74 mg, 0.54 mmol) and HATU (250 mg, 0.65 mmol) were dissolved in DMF (4 ml) and then DIPEA (0.23 ml) was then added. The mixture was stirred under nitrogen for 30 min. 6-bromo-1-methyl-1H-indazol-4-amine (135 mg, 0.60 mmol) was then added and stirring was continued under nitrogen overnight. Addition of water was followed by extraction of the resultant mixture with DCM (2×10 ml). The organics were combined and concentrated in vacuo then the residue was purified by chromatography on silica eluting with a gradient of 0-100% ethyl acetate in DCM. Fractions containing desired material were combined and concentrated in vacuo to afford the title compound (120 mg).

LCMS (Method B): $R_t$=1.24 mins, MH$^+$=346

Intermediate 18

3-Bromo-N-[6-(1H-indol-4-yl)-1H-indazol-4-yl]-2-pyridinecarboxamide

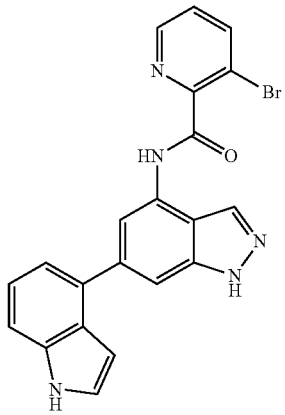 [SMILES: O=C(Nc1cc(-c2cccc3[nH]ccc23)cc2[nH]ncc12)c1ncccc1Br]

To a solution of 3-bromo-2-pyridinecarboxylic acid (available from Fluorochem Ltd, 0.81 g, 4.03 mmol) in DMF (10 ml) was added O-(7-azabenzotriazol-1-yl)-1,1,3,3-tetramethyluronium hexafluorophosphate (1.53 g, 4.03 mmol) and DIPEA (2.11 ml). The mixture was stirred at room temperature for 10 mins then 6-(1H-indol-4-yl)-1H-indazol-4-amine (0.5 g, 2.01 mmol) was added and the mixture stirred at room temperature for 2 h. The reaction mixture was concentrated in vacuo to 5 ml which was added to 2×50 g aminopropyl cartridges that had been preconditioned with MeOH. The reaction mixture remained on the cartridges for 2 h before being eluted with MeOH. The solvent was removed in vacuo to give a brown oil that was placed in the vacuum oven overnight. DCM was added to the oil and a precipitate occurred, which was collected by filtration to give the title compound (0.58 g) as a cream solid.

LC/MS (Method B) R$_t$ 1.00 mins, m/z 433 [M+H]$^+$.

Intermediate 19

6-Bromo-3-fluoro-4-nitro-1H-indazole: 6-bromo-4-nitro-1H-indazole (3:2)

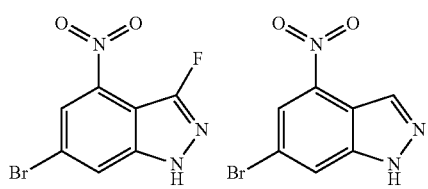

A microwave vial was charged with 6-bromo-4-nitro-1H-indazole (available from Sinova) (363 mg) and 1-(chloromethyl)-4-fluoro-1,4-diazoniabicyclo[2.2.2]octane ditetrafluoroborate (691 mg) followed by acetonitrile (5 ml) and acetic acid (1 ml). The reaction vessel was sealed and heated under microwave irradiation at 100° C. for two periods of 30 min then at 150° C. for two periods of 30 min. The solution was evaporated to dryness, dissolved in chloroform (~10 ml) and loaded onto a 20 g silica cartridge which was eluted on the Flashmaster 2 with a gradient of 0 to 100% ethyl acetate in cyclohexane over 60 min. The appropriate fractions were combined and blown to dryness to give the title compound (187 mg) as a yellow solid.

LC/MS R$_t$ 1.02 min m/z 258 [MH$^-$] and 0.98 min m/z 240. [MH$^-$]. Method B

Intermediate 20

6-Bromo-3-fluoro-1H-indazol-4-amine

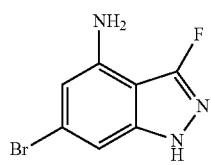 [SMILES: Nc1cc(Br)cc2[nH]nc(F)c12]

A mixture of 6-bromo-3-fluoro-4-nitro-1H-indazole and 6-bromo-4-nitro-1H-indazole (3:2) (187 mg) was dissolved in methanol (6 ml) and water (1.2 ml) and treated with sodium dithionate (519 mg). The solution was stirred for 2 h at 20° C. then left to stand for 3 days. This solution was then treated with sodium dithionite (438 mg) and stirred at 20° C. for 20 h. The solution was filtered through a filter tube, the residue washed with methanol (5 ml) then the combined filtrates were evaporated to dryness to give a yellow solid. This was treated with ethyl acetate (10 ml) and water (10 ml) and the solid dissolved. The organic phase was separated, dried with sodium sulphate, filtered then evaporated to give a pale yellow solid. This solid was treated with DCM (5 ml), methanol (5 ml) and ethyl acetate (10 ml), but some white solid did not dissolve. The supernatant was pipetted off, then blown to dryness to give a yellow solid which was dissolved in 1:1 methanol:DMSO (1 ml) and purified by mass directed preparative HPLC (Method A). The residue was azeotroped with methanol (5 ml) to give the title compound (19 mg) as a white solid.

LC/MS R$_t$ 2.83 min m/z 228 [MH]. Method A

Intermediate 21

3-Fluoro-6-(1H-indol-4-yl)-1H-indazol-4-amine

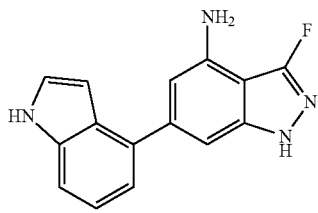 [SMILES: Nc1cc(-c2cccc3[nH]ccc23)cc2[nH]nc(F)c12]

To 4-(4,4,5,5-tetramethyl-1,3,2-dioxaborolan-2-yl)-1H-indole (24 mg) and 1,1'-bis(diphenylphosphino)ferrocene-dichloropalladium(II) (3 mg) at 20° C. in a microwave vial was added a solution of 6-bromo-3-fluoro-1H-indazol-4-amine (19 mg) in 1,4-dioxane (0.75 ml) followed by water (0.5 ml) and aqueous sodium carbonate (2M, 0.124 ml). The reaction vessel was sealed and heated under microwave irradiation at 150° C. for 15 min. After cooling, the black solution was loaded onto a 500 mg silica cartridge which was then eluted with methanol (4 column volumes). The eluant was blown to dryness, re-dissolved in methanol (3 ml), filtered and blown to dryness to give the title compound (67 mg) as a brown film.

LC/MS R$_t$ 2.99 min m/z 267 [MH$^+$]. Method A

Intermediate 22

6-(Chloromethyl)-N-[6-(1H-indol-4-yl)-1-(phenylsulfonyl)-1H-indazol-4-yl]-2-pyridinecarboxamide

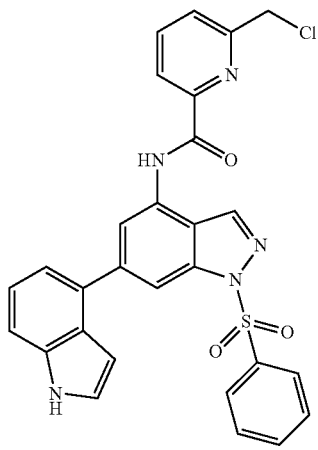 [SMILES: O=C(Nc1cc(-c2cccc3[nH]ccc23)cc2c1cnn2S(=O)(=O)c1ccccc1)c1cccc(CCl)n1]

To a solution of 6-(hydroxymethyl)-2-pyridinecarboxylic acid (500 mg, 3.27 mmol) in chloroform (10 ml) and N,N-dimethylformamide (DMF) (0.1 ml) was added thionyl chloride (1 ml, 13.70 mmol) and the mixture heated at 65° C. for 1 hr. Solvent was removed in vacuo and the residue was azeotroped with chloroform (5 ml) then dried on a high vacuum line for 30 mins to afford an orange oil (650 mg), presumed to be 6-(chloromethyl)-2-pyridinecarbonyl chloride. To solution of 6-(1H-indol-4-yl)-1-(phenylsulfonyl)-1H-indazol-4-amine (1.37 g, 3.53 mmol) in chloroform (30 ml) at 0° C. was added DIPEA (1.232 ml, 7.05 mmol). Crude 6-(chloromethyl)-2-pyridinecarbonyl chloride (1.519 g, crude) in chloroform (15 ml) was added dropwise and the mixture was stirred at 0° C. for 15 min. Water (30 ml) was added and the mixture was extracted with DCM (50 ml), separating the layers by hydrophobic frit. The solvent was removed in vacuo and the residue was dissolved in DCM (5 ml) and added to the top of 2×100 g silica SPE cartridges. One cartridge was eluted with 0-100% EtOAc/cyclohexane over 60 mins on the FlashMaster II. Product-containing fractions were and concentrated. The resultant solid was dissolved in 1:1 DCM/MeOH and loaded onto a 20 g aminopropyl cartridge that had been pre-conditioned with MeOH. The cartridge was then eluted with 1:1 DCM/MeOH and the fraction obtained was blown down under a stream of nitrogen. The solvent was removed in vacuo to give the title compound as a pink solid (487 mg). The second cartridge was eluted with 0-100% EtOAc/DCM over 60 mins on the FlashMaster II. The product-containing fractions were combined and concentrated to give a further portion of the title compound as a pink solid (449 mg).

LCMS (Method C) $R_t$=1.31 min, MH+=542.

Intermediate 23

6-(1H-Indol-4-yl)-1-(phenylsulfonyl)-1H-indazol-4-amine

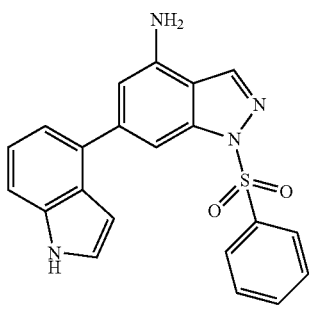 [SMILES: Nc1cc(-c2cccc3[nH]ccc23)cc2c1cnn2S(=O)(=O)c1ccccc1]

6-Bromo-1-(phenylsulfonyl)-1H-indazol-4-amine (3 g, 8.52 mmol), 4-(4,4,5,5-tetramethyl-1,3,2-dioxaborolan-2-yl)-1H-indole (2.28 g, 9.37 mmol), Pd(dppf)Cl$_2$ (0.623 g, 0.852 mmol) and sodium carbonate (2.71 g, 25.6 mmol) were divided equally between 2× microwave vials and each dissolved in 1,4-dioxane (8 mL) and water (8 mL). The vials were heated in the microwave at 110° C. for 15 min, then allowed to cool. The mixtures were combined and filtered through Celite, washing with EtOAc. The resulting mixture was partitioned between water (100 ml) and EtOAc (100 ml) and the layers separated. The aqueous layer was extracted with further EtOAc (2×50 ml) and the organic extracts were combined and the solvent removed in vacuo. The residue (4.6 g) was pre-adsorbed onto silica, which was added to the top of 2×100 g silica SPE cartridges. These were eluted with 0-100% EtOAc/cyclohexane over 60 minutes on the FlashMaster II. The product-containing fractions were combined and the solvent was removed in vacuo to afford the title compound as an orange solid (920 mg).

LCMS (Method C) $R_t$=1.04 min, MH$^+$=389.

Intermediate 24

1-(Phenylsulfonyl)-6-(trimethylstannanyl)-1H-indazol-4-amine

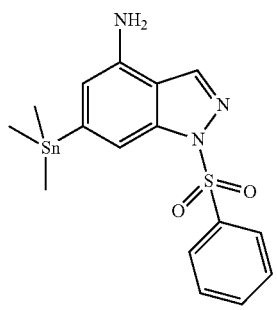 [SMILES: [CH3][Sn]([CH3])([CH3])[c]1cc(N)c2cnn(S(=O)(=O)c3ccccc3)c2c1]

A mixture of 6-bromo-1-(phenylsulfonyl)-1H-indazol-4-amine (1.3 g), hexamethylditin (2.4 g), triethylamine (1 ml) and Pd(PPh$_3$)$_4$ (0.2 g) in toluene (15 ml) was heated under microwave irradiation at 120° C. for 1 h. The reaction was applied to a silica cartridge using light petroleum 40-60° C. as eluent. This was changed to ether/light petroleum 40-60° C. The appropriate fractions were evaporated to give title compound, 1.2 g.

LCMS (Method C) $R_t$=3.3 min, MH$^+$ 438.

Intermediate 25

6-Bromo-1-(phenylsulfonyl)-1H-indazol-4-amine

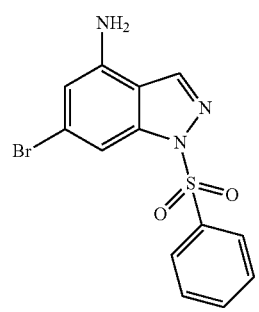 [SMILES: Nc1cc(Br)cc2c1cnn2S(=O)(=O)c1ccccc1]

6-Bromo-1H-indazol-4-amine (5 g) was dissolved in DMF (20 ml) and cooled in an ice bath. 60% Sodium hydride in mineral oil (0.94 g) was added portionwise and the reaction was left under an ice bath for 30 min. Benzenesulfonyl chloride (3 ml) in DMF (5 ml) was added slowly over 15 minutes and the reaction was left to warm up to room temperature overnight. Water (100 ml) was added and the reaction stirred for 20 minutes. Ethyl acetate (120 ml) was added and the water was separated, washed with ethyl acetate (50 ml×2) and the combined organics were washed with 7.5% lithium chloride (aq) (50 ml×2) then water (50 ml) before being separated and passed through a hydrophobic frit. The ethyl acetate was evaporated and the residue passed through a silica cartridge, eluting with DCM (ca. 300 ml) followed by diethyl ether (ca. 400 ml). Product containing pure fractions were combined and evaporated to dryness to give title compound, 5.9 g.

LCMS (Method B) $R_t$=1.12 min, MH$^+$354.

Intermediate 26

6-(Chloromethyl)-N-[1-(phenylsulfonyl)-6-(1H-pyrrolo[2,3-b]pyridin-4-yl)-1H-indazol-4-yl]-2-pyridinecarboxamide

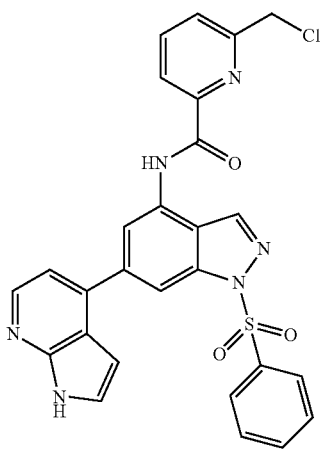 [SMILES: O=C(Nc1cc(-c2ccnc3[nH]ccc23)cc2c1cnn2S(=O)(=O)c1ccccc1)c1cccc(CCl)n1]

To a solution of 6-(hydroxymethyl)-2-pyridinecarboxylic acid (500 mg, 3.27 mmol) in chloroform (10 ml) and N,N-dimethylformamide (DMF) (0.1 ml) was added thionyl chloride (1 ml, 13.70 mmol) and the mixture heated at 65° C. for 1 hr. Solvent was removed in vacuo and the residue was azeotroped with chloroform (5 ml) then dried on a high vacuum line for 30 mins to afford an orange oil (650 mg), presumed to be 6-(chloromethyl)-2-pyridinecarbonyl chloride. To solution of 1-(phenylsulfonyl)-6-(1H-pyrrolo[2,3-b]pyridin-4-yl)-1H-indazol-4-amine (1.63 g, 4.19 mmol) in chloroform (25 ml) at 0° C. was added DIPEA (1.462 ml, 8.37 mmol). 6-(chloromethyl)-2-pyridinecarbonyl chloride (1.193 g, 6.28 mmol) in Chloroform (20 ml) was then added dropwise and the mixture was stirred at 0° C. for 15 min. A further portion of 6-(chloromethyl)-2-pyridinecarbonyl chloride (1.193 g, 6.28 mmol) in chloroform (20 ml) was added and the mixture was stirred at 0° C. for 15 min then warmed to room temperature and stirred for 18 h. The reaction mixture was quenched with water (100 ml) and extracted with DCM (100 ml). The solvent was removed in vacuo to give an orange solid. Trituration with DCM afforded the title compound (370 mg). The filtrate from the trituration was concentrated in vacuo to ~5 ml volume and then added to the top of 2×100 g silica SPE cartridges. The cartridges were eluted with a gradient of 0-100% EtOAc/DCM over 60 mins on the Flash Master II. The product-containing fractions were combined and the solvent removed in vacuo to give a further portion of the title compound as an off-white solid (530 mg).

LCMS (Method B) $R_t$=1.19 min, MH$^+$=543.

Intermediate 27

1-(Phenylsulfonyl)-6-(1H-pyrrolo[2,3-b]pyridin-4-yl)-1H-indazol-4-amine

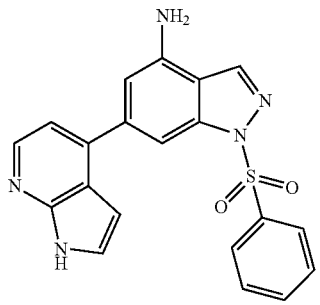 [SMILES: Nc1cc(-c2ccnc3[nH]ccc23)cc2c1cnn2S(=O)(=O)c1ccccc1]

1-(Phenylsulfonyl)-6-(4,4,6,6-tetramethyl-1,3,2-dioxaborinan-2-yl)-1H-indazol-4-amine (2 g, 4.84 mmol), 4-bromo-1H-pyrrolo[2,3-b]pyridine (0.953 g, 4.84 mmol), Pd(dppf)Cl$_2$ (0.708 g, 0.968 mmol) and Tripotassium phosphate (3.08 g, 14.52 mmol) were divided between 2× microwave vials and dissolved in 1,4-dioxane (24 ml) and water (8.00 ml); 12 ml dioxane and 4 ml water in each vial. The mixtures were heated in the microwave at 80° C. for 20 min. Solvent was removed in vacuo and the residue was partitioned between DCM (100 ml) and water (100 ml). The organic layer was collected using a hydrophobic frit and the solvent removed in vacuo. DCM was added to dissolve the crude residue but a suspension resulted. The yellow solid was filtered off and dried in a vacuum oven for 30 mins to afford the title compound (919 mg). The filtrate was concentrated in vacuo and dissolved in DCM, then applied to the top of a 50 g silica SPE cartridge. This was eluted with 0-100% EtOAc/DCM over 60 mins on the FlashMaster II. The product-containing fractions were combined to give a further portion of the title compound as a yellow solid (220 mg).

LCMS (Method B) $R_t$=0.89 min, MH$^+$=390.

Intermediate 28

6-(Chloromethyl)-N-{1-(phenylsulfonyl)-6-[1-(phenylsulfonyl)-1H-pyrazolo[3,4-b]pyridin-5-yl]-1H-indazol-4-yl}-2-pyridinecarboxamide

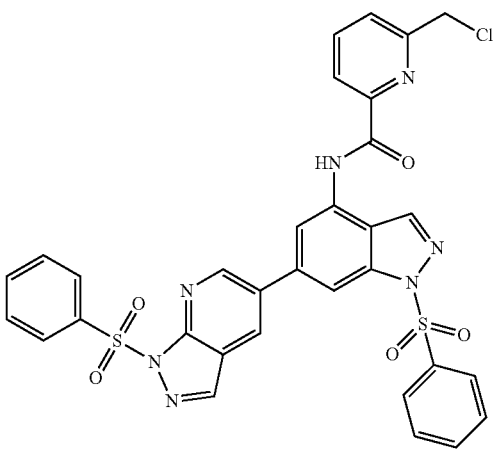 [SMILES: O=C(Nc1cc(-c2cnc3c(cnn3S(=O)(=O)c3ccccc3)c2)cc2c1cnn2S(=O)(=O)c1ccccc1)c1cccc(CCl)n1]

To a solution of 6-(hydroxymethyl)-2-pyridinecarboxylic acid (500 mg, 3.27 mmol) in chloroform (10 ml) and N,N-dimethylformamide (DMF) (0.1 ml) was added thionyl chloride (1 ml, 13.70 mmol) and the mixture heated at 65° C. for 1 hr. Solvent was removed in vacuo and the residue was azeotroped with chloroform (5 ml) then dried on a high vacuum line for 30 mins to afford an orange oil (650 mg), presumed to be 6-(chloromethyl)-2-pyridinecarbonyl chloride. To solution of 1-(phenylsulfonyl)-6-[1-(phenylsulfonyl)-1H-pyrazolo[3,4-b]pyridin-5-yl]-1H-indazol-4-amine (581 mg, 1.095 mmol) in chloroform (5 ml) at 0° C. was added DIPEA (0.383 ml, 2.190 mmol). 6-(chloromethyl)-2-pyridinecarbonyl chloride (330 mg, 1.737 mmol) in chloroform (5 ml) was added dropwise and the mixture was stirred at 0° C. for 15 min then allowed to warm to room temperature and stirred for another 30 mins. Water (10 ml) was added to quench the reaction and the mixture was extracted with DCM (2×20 ml), separating the layers using a hydrophobic frit. The solvent was removed in vacuo to give a brown solid, which was triturated with ether (5 ml). The resultant cream solid was filtered off and dried in a vacuum oven for 30 mins to afford the title compound (658 mg).

LCMS (Method B) $R_t$=1.35 min, MH$^+$=684.

Intermediate 29

1-(Phenylsulfonyl)-6-[1-(phenylsulfonyl)-1H-pyrazolo[3,4-b]pyridin-5-yl]-1H-indazol-4-amine

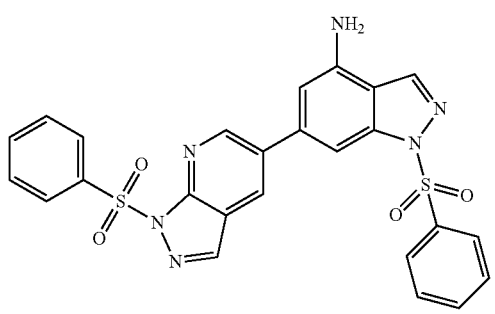 [SMILES: Nc1cc(-c2cnc3c(cnn3S(=O)(=O)c3ccccc3)c2)cc2c1cnn2S(=O)(=O)c1ccccc1]

1-(Phenylsulfonyl)-6-(4,4,6,6-tetramethyl-1,3,2-dioxaborinan-2-yl)-1H-indazol-4-amine (1.5 g, 3.63 mmol), 5-bromo-1-(phenylsulfonyl)-1H-pyrazolo[3,4-b]pyridine (1.350 g, 3.99 mmol), Pd(dppf)Cl$_2$ (0.531 g, 0.726 mmol) and tripotassium phosphate (2.311 g, 10.89 mmol) were divided between 2 microwave vials and dissolved in 1,4-dioxane (18 mL) and Water (6 mL); 9 ml dioxane and 3 ml water in each. Each vial was heated to 100° C. for 10 min in the microwave. Solvent was removed in vacuo and the residue was partitioned between DCM (100 ml) and water (100 ml). The organic layer was collected using a hydrophobic frit and the solvent was removed in vacuo. The residue was taken up in DCM (4 ml) and added to the top of 2×70 g silica SPE cartridges. These were subsequently eluted with 0-100% EtOAc/DCM over 40 mins. The product-containing fractions were combined to give the title compound as a pale yellow solid (581 mg).

LCMS (Method B) $R_t$=1.15 min, MH$^+$=531.

Intermediate 30

1-(Phenylsulfonyl)-6-[1-(phenylsulfonyl)-1H-pyrrolo[2,3-b]pyridin-4-yl]-1H-indazol-4-amine

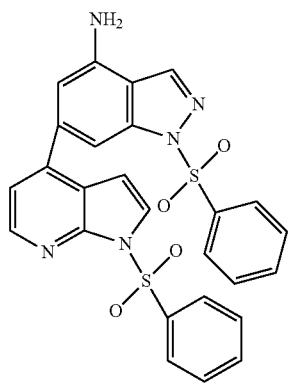 [SMILES: Nc1cc(-c2ccnc3c2ccn3S(O)(O)c2ccccc2)cc2c1cnn2S(O)(O)c1ccccc1]

4-Bromo-1-(phenylsulfonyl)-1H-pyrrolo[2,3-b]pyridine (1.546 g, 4.59 mmol), 1-(phenylsulfonyl)-6-(trimethylstannanyl)-1H-indazol-4-amine (2 g, 4.59 mmol) and Pd(Ph$_3$P)$_4$ (0.265 g, 0.229 mmol) were added to N,N-dimethylformamide (30 mL) under nitrogen. The mixture was heated at 100° C. for 2 days then cooled at room temperature and concentrated in vacuo. The mixture was purified by column chromatography on silica (70 g) eluting with ammonia and methanol in DCM, then again using the Companion technology and eluting with a gradient of 30 to 85% MeCN (+0.1% TFA)/H2O (0.1% TFA). Fractions containing desired product were combined and the solvent was removed to afford the title compound as a brown solid (663 mg).

LCMS (Method B) Rt=1.17 min, MH$^+$=530.

Intermediate 31

4-Bromo-1-(phenylsulfonyl)-1H-pyrrolo[2,3-b]pyridine

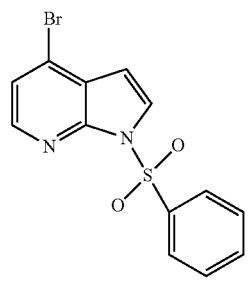 [SMILES: OS(O)(c1ccccc1)n1ccc2c(Br)ccnc21]

4-Bromo-1H-pyrrolo[2,3-b]pyridine (2 g, 10.15 mmol) and sodium hydride (0.406 g, 10.15 mmol) were added to N,N-dimethylformamide (30 mL) with stirring and under nitrogen. After 15 minutes the reaction was cooled in an ice bath and benzenesulfonyl chloride (1.295 mL, 10.15 mmol) was added. The reaction mixture was stirred in the ice bath for 30 min and then allowed to warm up to room temperature. Water (30 mL) was added and the precipitate collected by filtration to afford the title compound as an orange solid (4.8 g).

LCMS (Method B) $R_t$=1.19 min, MH$^+$=339.

Example 1

N-[6-(1H-Indol-4-yl)-1H-indazol-4-yl]-3-methyl-2-pyridinecarboxamide

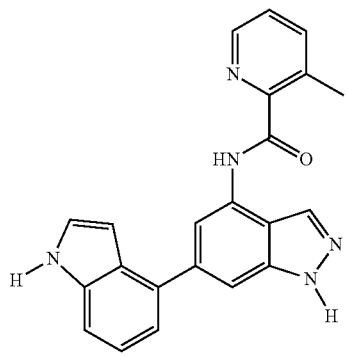 [SMILES: Cc1cccnc1C(=O)Nc1cc(-c2cccc3[nH]ccc23)cc2[nH]ncc12]

3-Methyl-2-pyridinecarboxylic acid (11 mg, 0.08 mmol) in DMF (0.20 ml) was treated with O-(7-azabenzotriazol-1-yl)-1,1,3,3-tetramethyluronium hexafluorophosphate (27 mg, 0.07 mmol) in DMF (0.20 ml) and DIPEA (0.030 ml). The reaction mixture was shaken for five minutes then treated with 6-(1H-Indol-4-yl)-2-(tetrahydro-2H-pyran-2-yl)-2H-indazol-4-amine (20 mg, 0.06 mmol) in DMF (0.20 ml). The reaction mixture was shaken then left to stand at room temperature overnight. Solvent was removed in vacuo and the product re-dissolved in methanol (1 ml) then applied to an SCX cartridge (1 g) which had been pre-rinsed with methanol. After 1 h, the cartridge was eluted with ammonia in methanol (2M, 2×3 ml). Fractions containing product were combined, dried and then further purified by Mass Directed Automated Preparative HPLC (Method D). Fractions containing product were combined and dried to give the title compound (5.5 mg) as a pale yellow gum.

LCMS (Method A) $R_t$=3.38 mins, MH$^+$=368.

Similarly prepared were:

| Example Number | Name | Structure | Precursor | LCMS $R_t$ (mins) | MH+ |
|---|---|---|---|---|---|
| 2 | 3-bromo-N-[6-(1H-indol-4-yl)-1H-indazol-4-yl]-2-pyridinecarboxamide | 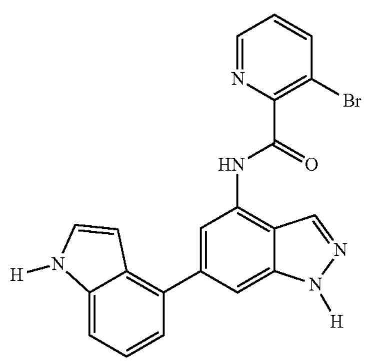 [SMILES: O=C(Nc1cc(-c2cccc3[nH]ccc23)cc2[nH]ncc12)c1ncccc1Br] | 3-bromo-2-pyridinecarboxylic acid | 3.20 (Method A) | 434 |
| 3 | 5-fluoro-N-[6-(1H-indol-4-yl)-1H-indazol-4-yl]-2-pyridinecarboxamide | 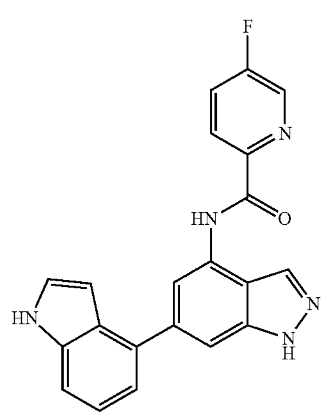 [SMILES: O=C(Nc1cc(-c2cccc3[nH]ccc23)cc2[nH]ncc12)c1ccc(F)cn1] | 5-fluoro-2-pyridinecarboxylic acid (available from Apollo); Purification by MDAP HPLC (Method C) | 1.02 (Method B) | 372 |

| Example Number | Name | Structure | Precursor | LCMS R$_t$ (mins) | MH+ |
|---|---|---|---|---|---|
| 4 | N-[6-(1H-indol-4-yl)-1H-indazol-4-yl]-6-[5-methyl-2-(methyloxy)phenyl]-2-pyridinecarboxamide | 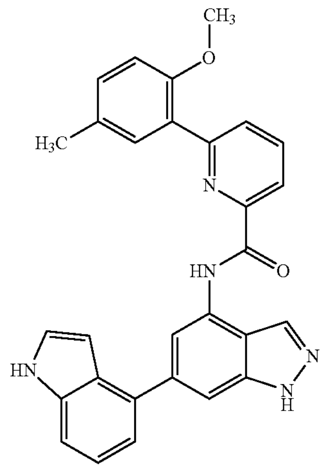 [SMILES: COc1ccc(C)cc1-c1cccc(C(=O)Nc2cc(-c3cccc4[nH]ccc34)cc3[nH]ncc23)n1] | 6-[5-methyl-2-(methyloxy)phenyl]-2-pyridinecarboxylic acid (Prepared as in WO 2001089457) Purification by MDAP HPLC (Method C) | 1.27 (Method B) | 474 |
| 5 | N-[6-(1H-indol-4-yl)-1H-indazol-4-yl]-6-(methyloxy)-2-pyridinecarboxamide | 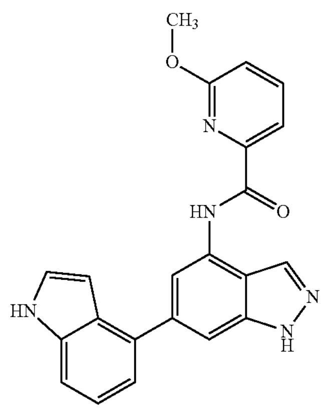 [SMILES: COc1cccc(C(=O)Nc2cc(-c3cccc4[nH]ccc34)cc3[nH]ncc23)n1] | 6-(methyloxy)-2-pyridinecarboxylic acid; Purification by MDAP HPLC (Method C) | 1.08 (Method B) | 384 |

Example 6

N-[6-(1H-Indol-4-yl)-1H-indazol-4-yl]-6-methyl-2-pyridinecarboxamide

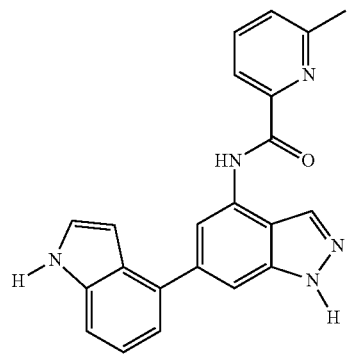 [SMILES: Cc1cccc(C(=O)Nc2cc(-c3cccc4[nH]ccc34)cc3[nH]ncc23)n1]

6-Methyl-2-pyridinecarboxylic acid (8 mg, 0.06 mmol) in DMF (0.20 ml) was treated with O-(7-azabenzotriazol-1-yl)-1,1,3,3-tetramethyluronium hexafluorophosphate (27 mg, 0.07 mmol) in DMF (0.20 ml) and DIPEA (0.030 ml). The reaction mixture was shaken for five minutes then treated with 6-(1H-Indol-4-yl)-2-(tetrahydro-2H-pyran-2-yl)-2H-indazol-4-amine (20 mg, 0.06 mmol) in DMF (0.20 ml). The reaction mixture was shaken for 5 mins then left to stand at room temperature overnight. Solvent was removed, and the product re-dissolved in methanol (1 ml) then applied to an SCX cartridge (1 g) which had been pre-rinsed with methanol. After 1 h, the cartridge was eluted with ammonia in methanol (2M, 2×3 ml). Fractions containing product were combined, dried and then further purified by Mass Directed Automated Preparative HPLC (Method D). Fractions containing product were combined and dried to give the title compound (6.6 mg) as a pale brown gum.

LCMS (Method B) R$_t$=1.06 mins, MH+=368.

Similarly prepared was:

| Example Number | Name | Structure | Precursor acid | LCMS $R_t$ (mins) | MH+ |
|---|---|---|---|---|---|
| 7 | 3,5-difluoro-N-[6-(1H-indol-4-yl)-1H-indazol-4-yl]-2-pyridinecarboxamide | 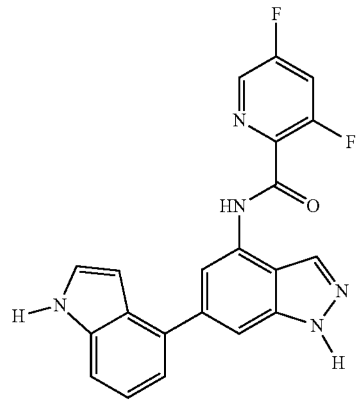 [SMILES: O=C(Nc1cc(-c2cccc3[nH]ccc23)cc2[nH]ncc12)c1ncc(F)cc1F] | 3,5-difluoro-2-pyridinecarboxylic acid | 0.99 | 390 |

Example 8

N-[1-Ethyl-6-(1H-indol-4-yl)-1H-indazol-4-yl]-6-methyl-2-pyridinecarboxamide

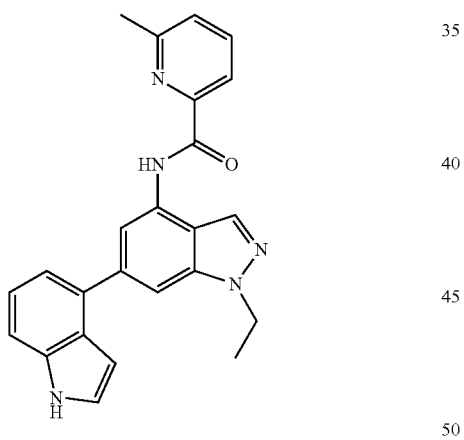

N-(6-Bromo-1-ethyl-1H-indazol-4-yl)-6-methyl-2-pyridinecarboxamide (50 mg, 0.14 mmol), 4-(4,4,5,5-tetramethyl-1,3,2-dioxaborolan-2-yl)-1H-indole (available from Frontier Scientific, 38 mg, 0.17 mmol), Pd(dppf)Cl$_2$ (23 mg), aqueous sodium carbonate (2M, 0.272 ml) and 1,4-dioxane (2 ml) were combined and heated at 150° C. for 10 mins under microwave conditions. The reaction was extracted into DCM (2×20 ml) and the combined organic layers were evaporated to dryness, before purification by Mass Directed Automated Preparative HPLC (Method B). Pure fractions were evaporated to give the title compound (25 mg).

LCMS (Method B) $R_t$=1.25 mins, MH$^+$=396.

Example 9

N-[6-(1H-Indol-4-yl)-1-methyl-1H-indazol-4-yl]-2-pyridinecarboxamide

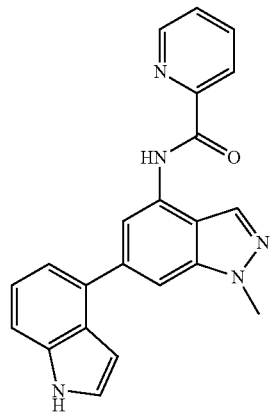 [SMILES: Cn1ncc2c(NC(=O)c3ccccn3)cc(-c3cccc4[nH]ccc34)cc21]

6-(1H-Indol-4-yl)-1-methyl-1H-indazol-4-amine (70 mg, 0.27 mmol) was dissolved in DCM (3 ml) and treated with DIPEA (0.145 ml). 2-Pyridinecarbonyl chloride hydrochloride (59.5 mg, 0.34 mmol) was added and the reaction was stirred for 5 h. MeOH (2 ml) was added and the reaction stirred overnight. The solvent was evaporated and the residue was treated with DCM/Methanol (1:1, 2 ml) then evaporated to dryness. The product was dissolved in DMSO (2 ml) and purified by Mass Directed Automated Preparative HPLC (Method B). Fractions containing product were combined and dried to give the title compound (23 mg).

LCMS (Method B) $R_t$=1.07 mins, MH$^+$=368.

Example 10

N-[6-(1H-Indol-4-yl)-1H-indazol-4-yl]-3-(methyloxy)-2-pyridinecarboxamide

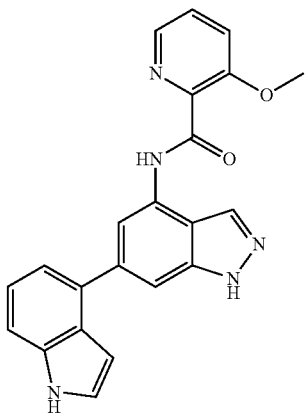 [SMILES: COc1cccnc1C(=O)Nc1cc(-c2cccc3[nH]ccc23)cc2[nH]ncc12]

3-(Methyloxy)-2-pyridinecarboxylic acid (available from Milestone Pharm Tech, 123 mg, 0.81 mmol), O-(7-azabenzotriazol-1-yl)-1,1,3,3-tetramethyluronium hexafluorophosphate (306 mg, 0.81 mmol) and DIPEA (0.422 ml) were stirred in DMF (2 ml) for 30 mins under nitrogen. Then 6-(1H-indol-4-yl)-1H-indazol-4-amine (100 mg, 0.40 mmol) was added and the reaction was stirred overnight. The reaction was loaded onto an aminopropyl column and left for 3 h, before eluting with 10% MeOH in DCM. Appropriate fractions were combined and evaporated under vacuum. The residue was purified by Mass Directed Automated Preparative HPLC (Method B). The solvent was dried under a stream of nitrogen to give the title compound (49 mg).

LCMS (Method B) $R_t$=0.90 mins, MH$^+$=384.

Example 11

6-[(Dimethylamino)methyl]-N-[6-(1H-indol-4-yl)-1H-indazol-4-yl]-2-pyridinecarboxamide

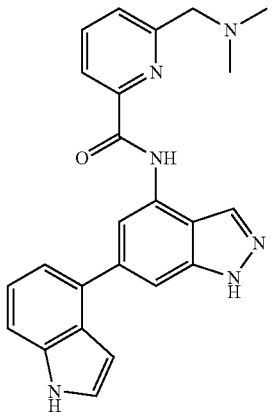 [SMILES: CN(C)Cc1cccc(C(=O)Nc2cc(-c3cccc4[nH]ccc34)cc3[nH]ncc23)n1]

A solution of 6-[(dimethylamino)methyl]-2-pyridinecarboxylic acid (27 mg, 0.15 mmol) in DMF (0.0008 ml) was treated with O-(7-azabenzotriazol-1-yl)-1,1,3,3-tetramethyluronium hexafluorophosphate (72 mg, 0.19 mmol) and DIPEA (0.052 ml). After 5 minutes the resulting solution was added to 6-(1H-indol-4-yl)-2-(tetrahydro-2H-pyran-2-yl)-2H-indazol-4-amine (33 mg, 0.10 mmol). After stirring for 90 mins at room temperature the mixture was treated with saturated sodium bicarbonate solution (10 ml) and extracted with dichloromethane (3×10 ml). The extracts were passed through a hydrophobic frit, combined and the solvent was evaporated under nitrogen flow. The residue was dissolved in methanol (2 ml) and hydrochloric acid (2M, 0.080 ml) was added. The solvents were evaporated under nitrogen stream to give a crude product which was purified by Mass Directed Automated Preparative HPLC (Method B). Fractions containing pure product were evaporated under a nitrogen stream to give the title compound (22 mg) as a pale solid.

LCMS (Method B) $R_t$=0.76 mins, MH$^+$=411.

Example 12

N-[6-(1H-Indol-4-yl)-1H-indazol-4-yl]-6-(4-morpholinylmethyl)-2-pyridinecarboxamide

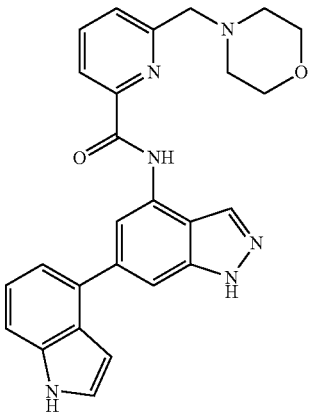 [SMILES: O=C(Nc1cc(-c2cccc3[nH]ccc23)cc2[nH]ncc12)c1cccc(CN2CCOCC2)n1]

A solution of 6-(4-morpholinylmethyl)-2-pyridinecarboxylic acid (33 mg, 0.15 mmol) in DMF (0.8 ml) was treated with O-(7-azabenzotriazol-1-yl)-1,1,3,3-tetramethyluronium hexafluorophosphate (72 mg, 0.19 mmol) and DIPEA (0.052 ml). After 5 minutes the resulting solution was added to 6-(1H-indol-4-yl)-2-(tetrahydro-2H-pyran-2-yl)-2H-indazol-4-amine (33 mg, 0.10 mmol). The mixture was stirred at room temperature for 15 mins then left to stand for 2 h. The reaction was treated with saturated sodium bicarbonate solution (10 ml) and extracted with dichloromethane (3×10 ml). The extracts were passed through a hydrophobic frit, combined and the solvent was evaporated under nitrogen flow. The residue was dissolved in methanol (1 ml) and hydrochloric acid (2M, 0.080 ml) was added. After about 1 hour the solvent was evaporated under a stream of nitrogen to give a crude product which was purified by Mass Directed Automated Preparative HPLC (Method B). Fractions containing pure product were evaporated under a nitrogen stream to give the title compound (11 mg) as a pale solid.

LCMS (Method B) $R_t$=0.77 mins, MH$^+$=453.

Example 13

N-[6-(1H-Indol-4-yl)-1H-indazol-4-yl]-6-(1-piperidinylmethyl)-2-pyridinecarboxamide

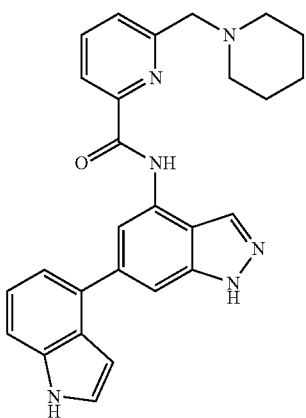 [SMILES: O=C(Nc1cc(-c2cccc3[nH]ccc23)cc2[nH]ncc12)c1cccc(CN2CCCCC2)n1]

To a solution of 6-(1-piperidinylmethyl)-2-pyridinecarboxylic acid (33 mg, 0.15 mmol) in DMF (0.6 ml) was added O-(7-azabenzotriazol-1-yl)-1,1,3,3-tetramethyluronium hexafluorophosphate (57 mg, 0.15 mmol) and DIPEA (0.052 ml) and the mixture was stirred for 5 mins at room temperature. 6-(1H-Indol-4-yl)-2-(tetrahydro-2H-pyran-2-yl)-2H-indazol-4-amine (33 mg, 0.10 mmol) was added and the mixture was stirred for 3 h and then overnight. The mixture was then treated with saturated sodium bicarbonate solution (10 ml) and extracted with dichloromethane (3×10 ml). The extracts were passed through a hydrophobic frit and blown to dryness under a stream of nitrogen. The crude product was dissolved in methanol (2 ml) and hydrochloric acid (5M, 2-3 drops) were added. The solution was shaken for 2 h then blown to dryness under a stream of nitrogen then purified by Mass Directed Automated Preparative HPLC (Method B) to give the title compound (17 mg).

LCMS (Method B) $R_t$=0.82 mins, MH$^+$=451.

Example 14

3-Fluoro-N-[6-(1H-indol-4-yl)-1H-indazol-4-yl]-2-pyridinecarboxamide

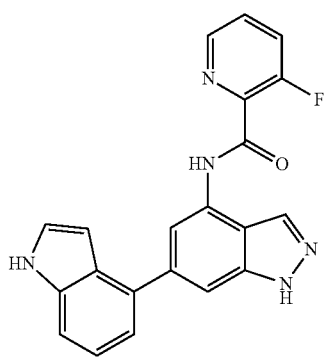 [SMILES: O=C(Nc1cc(-c2cccc3[nH]ccc23)cc2[nH]ncc12)c1ncccc1F]

To 3-fluoro-2-pyridinecarboxylic acid (available from Fluorochem, 63 mg, 0.44 mmol) was added O-(7-azabenzotriazol-1-yl)-1,1,3,3-tetramethyluronium hexafluorophosphate (172 mg, 0.45 mmol), DIPEA (0.106 ml) and DMF (1 ml). The reaction was stirred for 20 mins at 25° C. 6-(1H-indol-4-yl)-1H-indazol-4-amine (50 mg, 0.20 mmol) was added and the reaction was stirred for a further 20 h at 25° C. The solvent was dried under a stream of nitrogen to give the crude product. This sample in DMF was loaded onto an aminopropyl cartridge (5 g) and after standing for 3 h, the column was washed with 10% methanol in dichloromethane. The appropriate fractions were combined and dried under a stream of nitrogen to give the crude product which was purified by Mass Directed Automated Preparative HPLC (Method B). The solvent was dried under a stream of nitrogen to give the title compound (23 mg).

LCMS (Method B) $R_t$=0.94 mins, MH$^+$=372.

Example 15

N-[6-(1H-Indol-4-yl)-1H-indazol-4-yl]-3-pyridinecarboxamide

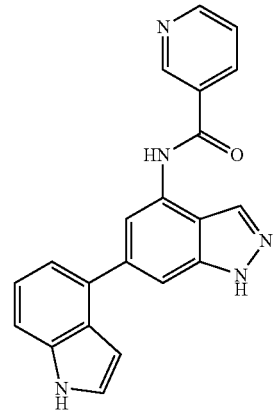 [SMILES: O=C(Nc1cc(-c2cccc3[nH]ccc23)cc2[nH]ncc12)c1cccnc1]

A mixture of 6-(1H-indol-4-yl)-2-(tetrahydro-2H-pyran-2-yl)-2H-indazol-4-amine (50 mg, 0.15 mmol), O-(7-azabenzotriazol-1-yl)-1,1,3,3-tetramethyluronium hexafluorophosphate (63 mg, 0.17 mmol) and 3-pyridinecarboxylic acid (20 mg, 0.16 mmol) was treated with DMF (2 ml) and DIPEA (0.052 ml). The reaction was stirred at room temperature for approximately 67.5 hours, then the solvent was removed in vacuo and the residue dissolved in methanol (3 ml). This was treated with macroporous p-toluenesulfonic acid resin (loading 1.43 mmol/g, 316 mg, 0.45 mmol), stirred for approximately 2 hours and then overnight, then treated with ammonia solution (0.88, 0.30 ml). The mixture was stirred for 5 mins, then the resin was filtered and the filtrate evaporated (blown down). The residue was purified by Mass Directed Automated Preparative HPLC (Method B). One fraction was evaporated to give the title compound (22 mg) as a yellow solid.

LCMS (Method B) $R_t$=0.85 mins, MH$^+$=354.

Example 16

N-[6-(1H-Indol-4-yl)-1H-indazol-4-yl]-3-(methylsulfonyl)-2-pyridinecarboxamide

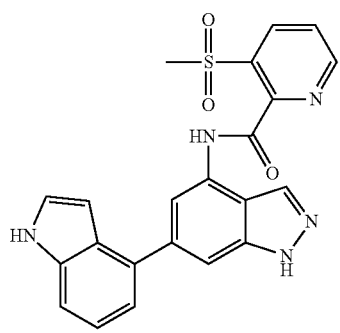 [SMILES: CS(=O)(=O)c1cccnc1C(=O)Nc1cc(-c2cccc3[nH]ccc23)cc2[nH]ncc12]

To 3-(methylsulfonyl)-2-pyridinecarboxylic acid (which may be prepared as described by Blank, Benjamin; DiTullio, Nicholas W.; Owings, Franklin F.; Deviney, Linda; Miao, Clara K.; Saunders, Harry L. *Journal of Medicinal Chemistry* (1977), 20(4), 572-576.) (89 mg, 0.44 mmol) was added O-(7-azabenzotriazol-1-yl)-1,1,3,3-tetramethyluronium hexafluorophosphate (172 mg, 0.45 mmol), DIPEA (0.106 ml) and DMF (1 ml). The reaction was stirred for 20 mins at 25° C. 6-(1H-Indol-4-yl)-1H-indazol-4-amine (50 mg, 0.20 mmol) was added and the reaction was stirred for a further 20 h at 25° C. The solvent was dried under a stream of nitrogen to give the crude product. This sample in DMF was loaded onto an aminopropyl cartridge (5 g) and after standing for 3 h, the column was washed with 10% methanol in dichloromethane. The appropriate fractions were combined and dried under a stream of nitrogen to give the crude product which was purified by Mass Directed Automated Preparative HPLC (Method B). The solvent was dried under a stream of nitrogen to give the title compound (29 mg).

LCMS (Method B) $R_t$=0.86 mins, MH$^+$=432.

Example 17

6-Chloro-3-fluoro-N-[6-(1H-indol-4-yl)-1H-indazol-4-yl]-2-pyridinecarboxamide

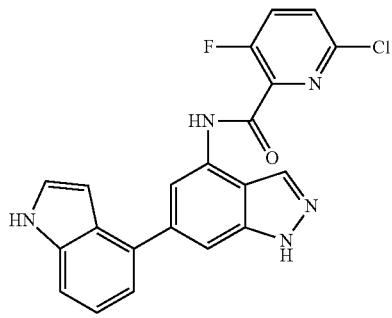 [SMILES: O=C(Nc1cc(-c2cccc3[nH]ccc23)cc2[nH]ncc12)c1nc(Cl)ccc1F]

6-Chloro-3-fluoro-2-pyridinecarboxylic acid (available from Asymchem, 848 mg, 4.83 mmol) and O-(7-azabenzotriazol-1-yl)-1,1,3,3-tetramethyluronium hexafluorophosphate (1838 mg, 4.83 mmol) were dissolved in DMF (15 ml) and DIPEA (2.53 ml) was added. The mixture was stirred at room temperature for 30 mins. 6-(1H-indol-4-yl)-1H-indazol-4-amine (600 mg, 2.42 mmol) was added and the mixture was stirred at room temperature for 36 h. Some solvent was removed in vacuo to give ~5 ml which was added to 2×50 g aminopropyl cartridges which had been preconditioned with methanol. The reaction mixture remained on the cartridges for 2 h before being eluted with methanol. Some solvent was removed in vacuo and a yellow precipitate crashed out which was filtered off to give the title compound (531 mg).

LCMS (Method B) $R_t$=1.02 mins, MH$^+$=406.

Example 18

6-Chloro-N-[6-(1H-indol-4-yl)-1H-indazol-4-yl]-2-pyridinecarboxamide

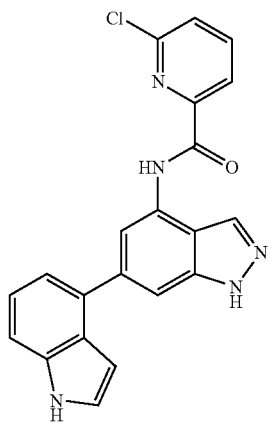 [SMILES: O=C(Nc1cc(-c2cccc3[nH]ccc23)cc2[nH]ncc12)c1cccc(Cl)n1]

6-Chloro-2-pyridinecarboxylic acid (available from Fluorochem, 2540 mg, 16.1 mmol) and O-(7-azabenzotriazol-1-yl)-1,1,3,3-tetramethyluronium hexafluorophosphate (6130 mg, 16.1 mmol) were dissolved in DMF (40 ml) and DIPEA (8.44 ml) was added. The mixture was stirred at room temperature for 30 mins then 6-(1H-indol-4-yl)-1H-indazol-4-amine (2000 mg, 8.06 mmol) was added and the mixture stirred at room temperature overnight. The reaction mixture was concentrated in vacuo to ~15 ml which was added to 4×50 g aminopropyl cartridges which had been preconditioned with MeOH. The reaction mixture remained on the cartridges for 3 h before being eluted with MeOH. The fractions were combined and the solvent was removed in vacuo to give a brown oil which was purified by chromatography on silica gel (2×100 g cartridges) eluting with 0-25% MeOH in dichloromethane over 40 mins. Appropriate fractions were combined and the solvent was removed in vacuo to give the title compound (809 mg) as an orange solid.

LCMS (Method B) $R_t$=1.07 mins, MH$^+$=388.

Example 19

N-[6-(1H-Indol-4-yl)-1H-indazol-4-yl]-6-(methylamino)-2-pyridinecarboxamide

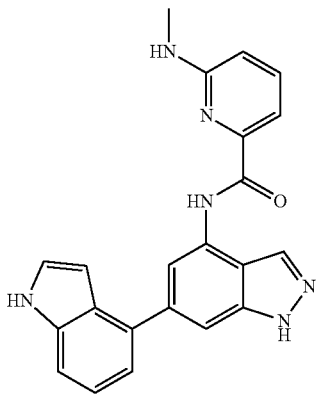 [SMILES: CNc1cccc(C(=O)Nc2cc(-c3cccc4[nH]ccc34)cc3[nH]ncc23)n1]

To a microwave vial was added 2 ml of a solution of 6-chloro-N-[6-(1H-indol-4-yl)-1H-indazol-4-yl]-2-pyridinecarboxamide (350 mg, 0.90 mmol, prepared as described in Example 18) in DMSO (14 ml). Methylamine (2M in THF, 0.129 ml, 0.26 mmol) and DIPEA (0.113 ml) were added and the mixture was heated at 160° C. for 4 h under microwave irradiation. Further methylamine (2M in THF, 0.129 ml, 0.26 mmol) was added and the mixture was again heated at 160° C. for 1 h under microwave irradiation. The crude reaction mixture was dissolved in DMSO/MeOH (1:1) and purified by Mass Directed Automated Preparative HPLC (Method B). Product-containing fractions were dried under a stream of nitrogen to afford the title compound (4.4 mg) as a pale yellow gum.

LCMS (Method B) $R_t$=1.02 mins, MH$^+$=383.

Example 20

N-[6-(1H-Indol-4-yl)-1H-indazol-4-yl]-6-[(1-methylethyl)amino]-2-pyridinecarboxamide

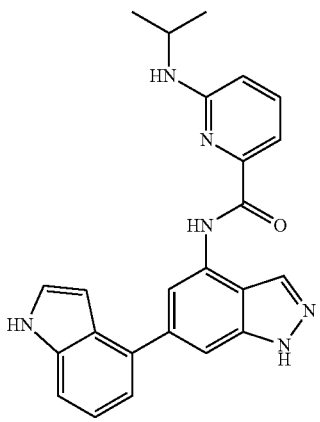 [SMILES: CC(C)Nc1cccc(C(=O)Nc2cc(-c3cccc4[nH]ccc34)cc3[nH]ncc23)n1]

To a microwave vial was added 2 ml of a solution of 6-chloro-N-[6-(1H-indol-4-yl)-1H-indazol-4-yl]-2-pyridinecarboxamide (350 mg, 0.90 mmol, prepared as described in Example 18) in DMSO (14 ml). 2-Propanamine (0.022 ml, 0.26 mmol) and DIPEA (0.113 ml) were added and the mixture was heated at 160° C. for 2 h under microwave irradiation. Further 2-propanamine (0.022 ml, 0.26 mmol) was added and the mixture was heated at 160° C. for 2 h under microwave irradiation. Again, 2-propanamine (0.02 ml, 0.26 mmol) was added and the mixture was heated at 160° C. for 1 h under microwave irradiation. After this time 2-propanamine (0.022 ml, 0.26 mmol) and DIPEA (0.113 ml) were both added to the mixture and it was heated at 160° C. for 2 h under microwave irradiation. The crude reaction mixture was dissolved in DMSO/MeOH (1:1) and purified by Mass Directed Automated Preparative HPLC (Method E). The sample was re-purified by Mass Directed Automated Preparative HPLC (Method E, using Waters Atlantis column 100 mm×19 mm, 5 um). Product-containing fractions were dried under a stream of nitrogen to afford the title compound (2.1 mg).

LCMS (Method B) $R_t$=1.16 mins, MH$^+$=411.

Example 21

6-(Ethylamino)-N-[6-(1H-indol-4-yl)-1H-indazol-4-yl]-2-pyridinecarboxamide

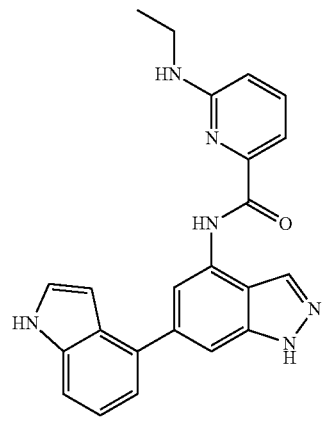 [SMILES: CCNc1cccc(C(=O)Nc2cc(-c3cccc4[nH]ccc34)cc3[nH]ncc23)n1]

To a microwave vial was added 2 ml of a solution of 6-chloro-N-[6-(1H-indol-4-yl)-1H-indazol-4-yl]-2-pyridinecarboxamide (350 mg, 0.90 mmol, prepared as described in Example 18) in DMSO (14 ml). Ethylamine (0.021 ml, 0.26 mmol) and DIPEA (0.113 ml) were added and the mixture was heated at 160° C. for 2 h under microwave irradiation. Further ethylamine (0.021 ml, 0.26 mmol) was added and the mixture was heated at 160° C. for 2 h under microwave irradiation. Again, ethylamine (0.021 ml, 0.26 mmol) was added and the mixture was heated at 160° C. for 1 h under microwave irradiation. After this time ethylamine (0.021 ml, 0.26 mmol) and DIPEA (0.113 ml) were both added to the mixture and it was heated at 160° C. for 2 h under microwave irradiation. Finally, additional ethylamine (0.021 ml, 0.26 mmol) and DIPEA (0.113 ml) were added and the mixture was heated at 170° C. for 1 h under microwave irradiation. The crude reaction mixture was dissolved in DMSO/MeOH (1:1) and purified by Mass Directed Automated Preparative HPLC (Method E). The sample was re-purified by Mass Directed Automated Preparative HPLC (Method E, using Waters Atlantis column 100 mm×19 mm, 5 um). Product-containing fractions were dried under a stream of nitrogen to afford the title compound (3.3 mg).

LCMS (Method B) $R_t$=1.11 mins, MH$^+$=397.

Example 22

6-(Diethylamino)-N-[6-(1H-indol-4-yl)-1H-indazol-4-yl]-2-pyridinecarboxamide

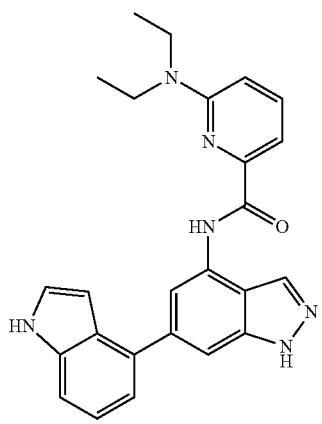 [SMILES: CCN(CC)c1cccc(C(=O)Nc2cc(-c3cccc4[nH]ccc34)cc3[nH]ncc23)n1]

To a microwave vial was added 2 ml of a solution of 6-chloro-N-[6-(1H-indol-4-yl)-1H-indazol-4-yl]-2-pyridinecarboxamide (350 mg, 0.90 mmol, prepared as described in Example 18) in DMSO (14 ml). Diethylamine (0.027 ml, 0.26 mmol) and DIPEA (0.113 ml) were added and the mixture was heated at 160° C. for 2 h under microwave irradiation. Further diethylamine (0.027 ml, 0.26 mmol) was added and the mixture was heated at 160° C. for 2 h under microwave irradiation. Again, diethylamine (0.027 ml, 0.26 mmol) was added and the mixture was heated at 160° C. for 1 h under microwave irradiation. After this time, diethylamine (0.027 ml, 0.26 mmol) and DIPEA (0.113 ml) were both added to the mixture and it was heated at 160° C. for 2 h under microwave irradiation. The crude reaction mixture was dissolved in DMSO/MeOH (1:1) and purified by Mass Directed Automated Preparative HPLC (Method E). Product-containing fractions were dried under a stream of nitrogen to afford the title compound (4.7 mg).

LCMS (Method B) $R_t$=1.27 mins, $MH^+$=425.

Example 23

6-(Cyclopropylamino)-N-[6-(1H-indol-4-yl)-1H-indazol-4-yl]-2-pyridinecarboxamide

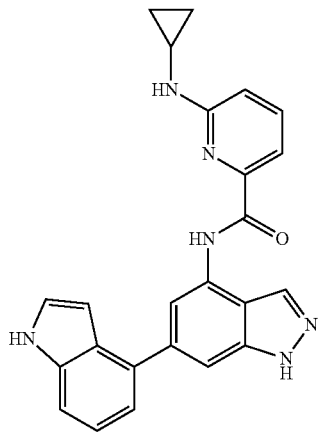 [SMILES: O=C(Nc1cc(-c2cccc3[nH]ccc23)cc2[nH]ncc12)c1cccc(NC2CC2)n1]

To a microwave vial was added 2 ml of a solution of 6-chloro-N-[6-(1H-indol-4-yl)-1H-indazol-4-yl]-2-pyridinecarboxamide (350 mg, 0.90 mmol, prepared as described in Example 18) in DMSO (14 ml). Cyclopropylamine (0.018 ml, 0.26 mmol) and DIPEA (0.113 ml) were added and the mixture was heated at 160° C. for 2 h under microwave irradiation. Further cyclopropylamine (0.018 ml, 0.26 mmol) was added and the mixture was heated at 160° C. for 2 h under microwave irradiation. Again, cyclopropylamine (0.018 ml, 0.26 mmol) was added and the mixture was heated at 160° C. for 1 h under microwave irradiation. After this time, cyclopropylamine (0.018 ml, 0.26 mmol) and DIPEA (0.113 ml) were both added to the mixture and it was heated at 160° C. for 2 h under microwave irradiation. The crude reaction mixture was dissolved in DMSO/MeOH (1:1) and purified by Mass Directed Automated Preparative HPLC (Method E). The sample was re-purified by Mass Directed Automated Preparative HPLC (Method E, using Waters Atlantis column 100 mm×19 mm, 5 um). Product-containing fractions were dried under a stream of nitrogen to afford the title compound (1.9 mg).

LCMS (Method B) $R_t$=1.15 mins, $MH^+$=409.

Example 24

N-[6-(1H-Indol-4-yl)-1H-indazol-4-yl]-6-(4-methyl-1-piperazinyl)-2-pyridinecarboxamide

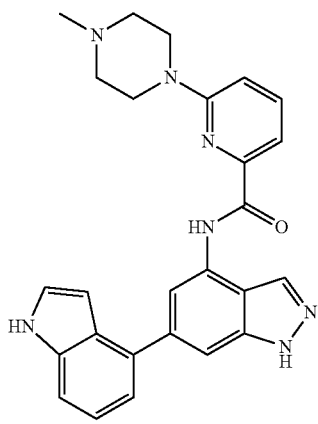 [SMILES: CN1CCN(c2cccc(C(=O)Nc3cc(-c4cccc5[nH]ccc45)cc4[nH]ncc34)n2)CC1]

To a microwave vial was added 2 ml of a solution of 6-chloro-N-[6-(1H-indol-4-yl)-1H-indazol-4-yl]-2-pyridinecarboxamide (350 mg, 0.90 mmol, prepared as described in Example 18) in DMSO (14 ml). 1-methylpiperazine (0.029 ml, 0.26 mmol) and DIPEA (0.113 ml) were added and the mixture was heated at 160° C. for 4 h under microwave irradiation. The crude reaction mixture was dissolved in DMSO/MeOH (1:1) and purified by using Mass Directed Automated Preparative HPLC (Method E). Product-containing fractions were dried under a stream of nitrogen to afford the title compound (12.8 mg).

LCMS (Method B) $R_t$ 0.82 mins, $MH^+$=452.

Example 25

N-[6-(1H-Indol-4-yl)-1H-indazol-4-yl]-6-(1-pyrrolidinyl)-2-pyridinecarboxamide

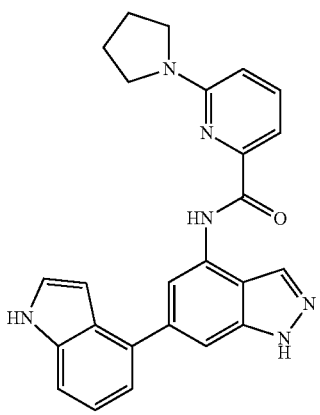 [SMILES: O=C(Nc1cc(-c2cccc3[nH]ccc23)cc2[nH]ncc12)c1cccc(N2CCCC2)n1]

To a microwave vial was added 2 ml of a solution of 6-chloro-N-[6-(1H-indol-4-yl)-1H-indazol-4-yl]-2-pyridinecarboxamide (350 mg, 0.26 mmol, prepared as described in Example 18) in DMSO (14 ml). Pyrrolidine (0.022 ml, 0.26 mmol) and DIPEA (0.113 ml) were added and the mixture was heated at 160° C. for 3 h under microwave irradiation. The crude reaction mixture was dissolved in DMSO/MeOH (1:1) and purified by Mass Directed Automated Preparative HPLC (Method B). Product-containing fractions were dried under a stream of nitrogen to afford the title compound (17.6 mg).

LCMS (Method B) $R_t$=1.23 mins, $MH^+$=423.

Example 26

6-(Dimethylamino)-N-[6-(1H-indol-4-yl)-1H-indazol-4-yl]-2-pyridinecarboxamide

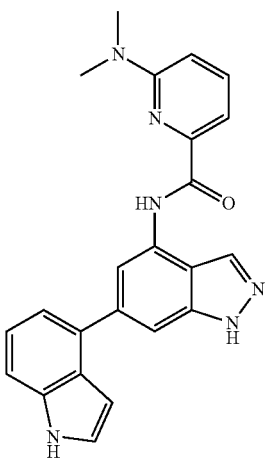 [SMILES: CN(C)c1cccc(C(=O)Nc2cc(-c3cccc4[nH]ccc34)cc3[nH]ncc23)n1]

To a solution of 6-chloro-N-[6-(1H-indol-4-yl)-1H-indazol-4-yl]-2-pyridinecarboxamide (40 mg, 0.10 mmol, prepared as described in Example 18) in DMSO (1 ml) was added dimethylamine (2M in THF, 0.052 ml, 0.10 mmol) and DIPEA (0.09 ml). The mixture was heated under microwave irradiation firstly at 140° C. for 1 h, then at 160° C. for 1 h and then at 180° C. for 1 h. Further dimethylamine (2M in THF, 0.052 ml, 0.10 mmol) was added and the mixture was heated under microwave irradiation at 160° C. for 2 h. The product was then purified by Mass Directed Automated Preparative HPLC (Method B), then further purified by chromatography using an SCX cartridge (1 g), which was eluted with MeOH (2 column volumes) and then ammonia in MeOH (2M, 1 column volume). The product-containing fractions were combined and blown down under a stream of nitrogen. Purification using an aminopropyl cartridge (1 g), which was eluted with MeOH (1 column volume), afforded the title compound (9.8 mg) as a pale orange gum.

LCMS (Method B) $R_t$=1.13 mins, $MH^+$=397.

Example 27

3,6-Dichloro-N-[6-(1H-indol-4-yl)-1H-indazol-4-yl]-2-pyridinecarboxamide

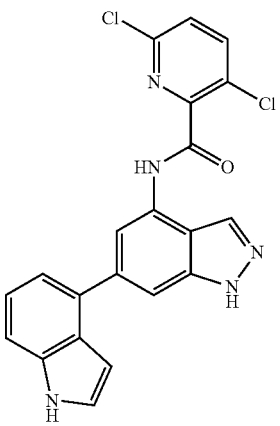 [SMILES: O=C(Nc1cc(-c2cccc3[nH]ccc23)cc2[nH]ncc12)c1nc(Cl)ccc1Cl]

To a solution of 3,6-dichloro-2-pyridinecarboxylic acid (available from Matrix Scientific, 930 mg, 4.8 mmol) and O-(7-azabenzotriazol-1-yl)-1,1,3,3-tetramethyluronium hexafluorophosphate (1840 mg, 4.8 mmol) were dissolved in DMF (15 ml) and treated with DIPEA (2.53 ml). The mixture was stirred at room temperature for 30 mins then 6-(1H-indol-4-yl)-1H-indazol-4-amine (600 mg, 2.4 mmol) was added and the mixture stirred at room temperature overnight. The reaction mixture was concentrated in vacuo to approx. 5 ml which was added to 2×50 g aminopropyl cartridges that had been preconditioned with MeOH. The reaction mixture remained on the cartridges for 3 h before being eluted with MeOH. The mixture was concentrated in vacuo and a precipitate occurred, which was collected by filtration to give the title compound (0.55 g) as a yellow solid.

LCMS (Method B) $R_t$=1.06 mins, $MH^+$=422.

Example 28

3-Chloro-N-[6-(1H-indol-4-yl)-1H-indazol-4-yl]-6-(4-morpholinyl)-2-pyridinecarboxamide

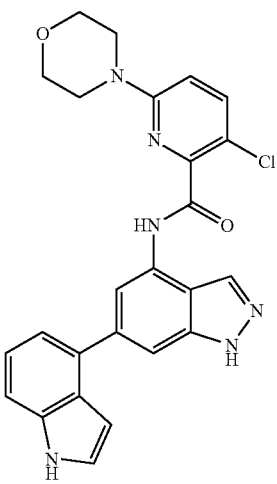 [SMILES: O=C(Nc1cc(-c2cccc3[nH]ccc23)cc2[nH]ncc12)c1nc(N2CCOCC2)ccc1Cl]

To a microwave vial was added 2 ml of a solution of 3,6-dichloro-N-[6-(1H-indol-4-yl)-1H-indazol-4-yl]-2-pyridinecarboxamide (306 mg, 0.71 mmol) in DMSO (6 ml). Morpholine (0.022 ml, 0.25 mmol) and DIPEA (0.129 ml) were added and the mixture was heated at 160° C. for 3 h under microwave irradiation. The crude reaction mixture was dissolved in DMSO/MeOH (1:1) and purified by Mass Directed Automated Preparative HPLC (Method E). The sample was further purified by Mass Directed Automated Preparative HPLC (Method E) and product-containing fractions were dried under a stream of nitrogen to afford the title compound (19 mg).

LCMS (Method B) $R_t$=1.08 mins, MH$^+$=473.

Example 29

3-Chloro-N-[6-(1H-indol-4-yl)-1H-indazol-4-yl]-6-(1-piperidinyl)-2-pyridinecarboxamide

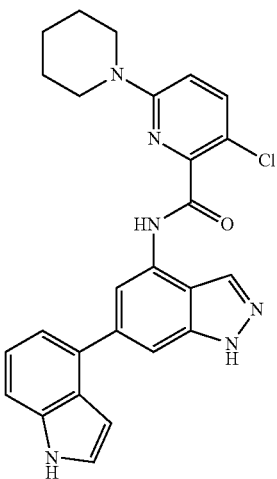 [SMILES: O=C(Nc1cc(-c2cccc3[nH]ccc23)cc2[nH]ncc12)c1nc(N2CCCCC2)ccc1Cl]

To a microwave vial was added 2 ml of a solution of 3,6-dichloro-N-[6-(1H-indol-4-yl)-1H-indazol-4-yl]-2-pyridinecarboxamide (306 mg, 0.71 mmol) in DMSO (6 ml). Piperidine (0.024 ml, 0.25 mmol) and DIPEA (0.129 ml) were added and the mixture was heated at 160° C. for 2 h under microwave irradiation. The crude reaction mixture was dissolved in DMSO/MeOH (1:1) and purified by Mass Directed Automated Preparative HPLC (Method E). The sample was further purified by Mass Directed Automated Preparative HPLC (Method E) and product-containing fractions were dried under a stream of nitrogen to afford the title compound (22 mg).

LCMS (Method B) $R_t$=1.28 mins, MH$^+$=471.

Example 30

3-Chloro-6-(dimethylamino)-N-[6-(1H-indol-4-yl)-1H-indazol-4-yl]-2-pyridinecarboxamide

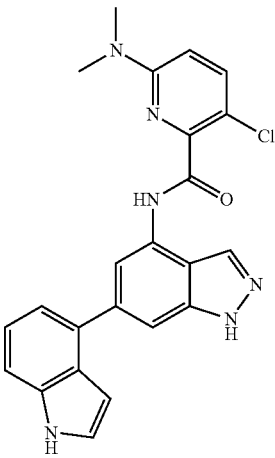 [SMILES: CN(C)c1ccc(Cl)c(C(=O)Nc2cc(-c3cccc4[nH]ccc34)cc3[nH]ncc23)n1]

To a microwave vial was added 2 ml of a solution of 3,6-dichloro-N-[6-(1H-indol-4-yl)-1H-indazol-4-yl]-2-pyridinecarboxamide (306 mg, 0.71 mmol) in DMSO (6 ml). Dimethylamine (2M in THF, 0.123 ml, 0.25 mmol) and DIPEA (0.129 ml) were added and the mixture was heated at 160° C. for 2 h under microwave irradiation. The crude reaction mixture was dissolved in DMSO/MeOH (1:1) and purified by Mass Directed Automated Preparative HPLC (Method E). The sample was further purified by Mass Directed Automated Preparative HPLC (Method E) and product-containing fractions were dried under a stream of nitrogen to afford the title compound (15 mg).

LCMS (Method B) $R_t$=1.16 mins, MH$^+$=431.

Example 31

6-Fluoro-N-[6-(1H-indol-4-yl)-1H-indazol-4-yl]-2-pyridinecarboxamide

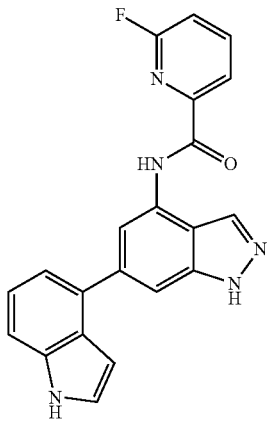 [SMILES: O=C(Nc1cc(-c2cccc3[nH]ccc23)cc2[nH]ncc12)c1cccc(F)n1]

6-Fluoro-2-pyridinecarboxylic acid (available from Asymchem Laboratories, 570 mg, 4.0 mmol) and O-(7-azabenzotriazol-1-yl)-1,1,3,3-tetramethyluronium hexafluorophosphate (1531 mg, 4.0 mmol) were dissolved in DMF (15 ml) and treated with DIPEA (2.11 ml). The mixture was stirred at room temperature for 30 mins then 6-(1H-indol-4-yl)-1H-indazol-4-amine (500 mg, 2.0 mmol) was added and the mixture stirred at room temperature overnight. The reaction mixture was concentrated in vacuo to approx. 5 ml which was added to 2×50 g aminopropyl cartridges that had been preconditioned with MeOH. The reaction mixture remained on the cartridges for 2 h before being eluted with MeOH. The mixture was concentrated in vacuo to give an orange oil. DCM (5 ml) was added and the resultant precipitate was collected by filtration to give the title compound (235 mg) as a yellow solid.

LCMS (Method B) $R_t$=1.04 mins, $MH^+$=372.

Example 32

N-[6-(1H-Indol-4-yl)-1H-indazol-4-yl]-6-[methyl(tetrahydro-2H-pyran-4-yl)amino]-2-pyridinecarboxamide

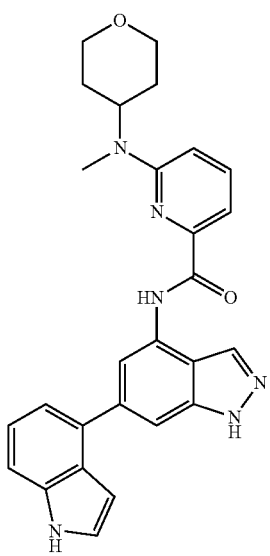 [SMILES: CN(c1cccc(C(=O)Nc2cc(-c3cccc4[nH]ccc34)cc3[nH]ncc23)n1)C1CCOCC1]

6-Fluoro-N-[6-(1H-indol-4-yl)-1H-indazol-4-yl]-2-pyridinecarboxamide (50 mg, 0.14 mmol) and methyl(tetrahydro-2H-pyran-4-yl)amine (31 mg, 0.27 mmol) were dissolved in DMSO (0.5 ml) in a microwave vial. DIPEA (0.141 ml) was added and the mixture was heated at 160° C. for 4 h under microwave irradiation. The reaction mixture was diluted with MeOH (0.5 ml) and was purified by Mass Directed Automated Preparative HPLC (Method C). Fractions containing product were blown to dryness and the residue dissolved in methanol. This solution was loaded onto a 1 g aminopropyl column which was eluted with MeOH (1 column volume). The solvent was removed under a stream of nitrogen to give the title compound (17 mg) as a cream solid.

LCMS (Method B) $R_t$=1.14 mins, $MH^+$=467.

Example 33

N-[6-(1H-Indol-4-yl)-1H-indazol-4-yl]-6-[(1-methyl-4-piperidinyl)amino]-2-pyridinecarboxamide

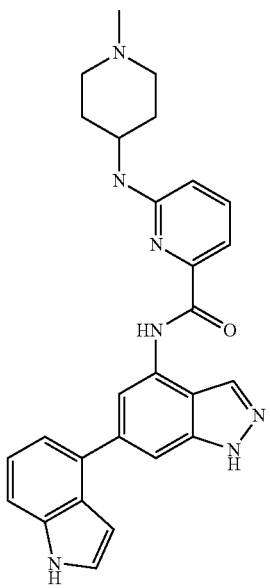 [SMILES: CN1CCC(Nc2cccc(C(=O)Nc3cc(-c4cccc5[nH]ccc45)cc4[nH]ncc34)n2)CC1]

6-Fluoro-N-[6-(1H-indol-4-yl)-1H-indazol-4-yl]-2-pyridinecarboxamide (50 mg, 0.14 mmol) and 1-methyl-4-piperidinamine (30.7 mg, 0.27 mmol) were dissolved in DMSO (0.5 ml) in a microwave vial. DIPEA (0.141 ml) was added and the mixture was heated at 160° C. for 4 h under microwave irradiation. The reaction mixture was diluted with MeOH (0.5 ml) and was purified by Mass Directed Automated Preparative HPLC (Method C). Fractions containing product were blown to dryness and the residue dissolved in methanol. This solution was loaded onto a 1 g aminopropyl column which was eluted with MeOH (1 column volume). The solvent removed under a stream of nitrogen to give the title compound (28 mg) as a cream solid.

LCMS (Method B) $R_t$=0.86 mins, $MH^+$=466.

Example 34

N-[6-(1H-Indol-4-yl)-1H-indazol-4-yl]-6-(tetrahydro-2H-pyran-4-ylamino)-2-pyridinecarboxamide

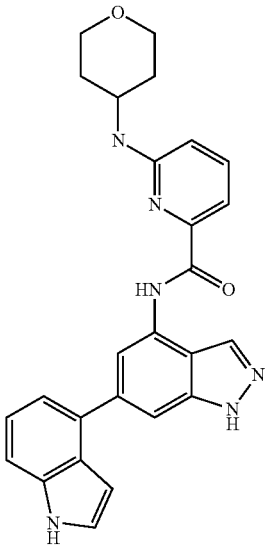 [SMILES: O=C(Nc1cc(-c2cccc3[nH]ccc23)cc2[nH]ncc12)c1cccc(NC2CCOCC2)n1]

6-Fluoro-N-[6-(1H-indol-4-yl)-1H-indazol-4-yl]-2-pyridinecarboxamide (100 mg, 0.27 mmol) and tetrahydro-2H-pyran-4-amine (55 mg, 0.54 mmol) were dissolved in DMSO (1.5 ml) in a microwave vial. DIPEA (0.282 ml) was added and the mixture was heated at 160° C. for 3 h under microwave irradiation. The reaction mixture was concentrated under a stream of nitrogen and redissolved in methanol. This solution was loaded onto a 2 g aminopropyl column, which was been preconditioned with methanol. The column was eluted with methanol (2 column volumes) and the desired fraction was blown to dryness under nitrogen. The sample was then purified by Mass Directed Automated Preparative HPLC (Method B) to give the title compound (57 mg) as a white solid.

LCMS (Method B) $R_t$=1.00 mins, $MH^+$=453.

Example 35

6-Chloro-3-(dimethylamino)-N-[6-(1H-indol-4-yl)-1H-indazol-4-yl]-2-pyridinecarboxamide

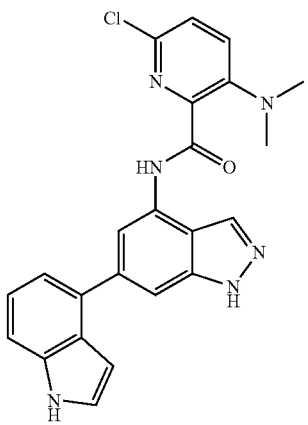 [SMILES: CN(C)c1ccc(Cl)nc1C(=O)Nc1cc(-c2cccc3[nH]ccc23)cc2[nH]ncc12]

6-Chloro-3-fluoro-N-[6-(1H-indol-4-yl)-1H-indazol-4-yl]-2-pyridinecarboxamide (188 mg, 0.46 mmol) was placed in a microwave vial and dissolved in THF (4 ml). Dimethylamine (0.463 ml, 0.93 mmol) and DIPEA (0.485 ml) were added and the mixture was heated at 160° C. for 1 h under microwave irradiation. The solvent was removed in vacuo and the yellow residue was dissolved in DCM (10 ml) and washed with water (10 ml). The DCM was removed in vacuo and the solid was dried in vacuo on a high vacuum line to afford the title compound (400 mg) as a yellow solid.

LCMS (Method B) $R_t$=1.07 mins, $MH^+$=431.

Example 36

3-(Dimethylamino)-N-[6-(1H-indol-4-yl)-1H-indazol-4-yl]-6-(4-morpholinyl)-2-pyridinecarboxamide

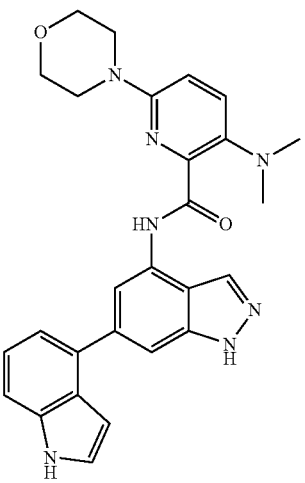 [SMILES: CN(C)c1ccc(N2CCOCC2)nc1C(=O)Nc1cc(-c2cccc3[nH]ccc23)cc2[nH]ncc12]

6-Chloro-3-fluoro-N-[6-(1H-indol-4-yl)-1H-indazol-4-yl]-2-pyridinecarboxamide (50 mg, 0.12 mmol) was placed in a microwave vial and dissolved in morpholine (0.5 ml). The mixture was heated at 160° C. for 2 h under microwave irradiation. The solvent was removed under a stream of nitrogen to give a crude residue that was dissolved in DMSO/MeOH (1:1) and purified by Mass Directed Automated Preparative HPLC (Method C). The product was loaded onto a 1 g aminopropyl column, eluted with MeOH and the solvent removed under a stream of nitrogen to give the title compound (16 mg) as an orange solid.

LCMS (Method B) $R_t$=0.87 min, $MH^+$=482.

Example 37

3-(Dimethylamino)-N-[6-(1H-indol-4-yl)-1H-indazol-4-yl]-6-(1-piperidinyl)-2-pyridinecarboxamide

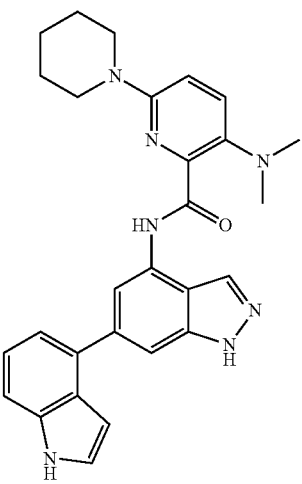 [SMILES: CN(C)c1ccc(N2CCCCC2)nc1C(=O)Nc1cc(-c2cccc3[nH]ccc23)cc2[nH]ncc12]

6-Chloro-3-fluoro-N-[6-(1H-indol-4-yl)-1H-indazol-4-yl]-2-pyridinecarboxamide (50 mg, 0.12 mmol) was placed in a microwave vial and dissolved in piperidine (0.5 ml). The mixture was heated at 160° C. for 1 h under microwave irradiation. The solvent was removed under a stream of nitrogen to give a crude residue that was dissolved in DMSO/MeOH (1:1) and purified by Mass Directed Automated Preparative HPLC (Method C). The product was loaded onto a 1 g aminopropyl column, eluted with MeOH and the solvent removed under a stream of nitrogen to give the title compound (7 mg) as a yellow solid.

LCMS (Method B) $R_t$=1.01 mins, MH$^+$=480.

Example 38

3-(Dimethylamino)-N-[6-(1H-indol-4-yl)-1H-indazol-4-yl]-6-(methylamino)-2-pyridinecarboxamide

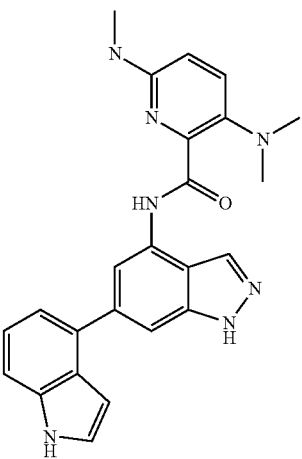 [SMILES: CNc1ccc(N(C)C)c(C(=O)Nc2cc(-c3cccc4[nH]ccc34)cc3[nH]ncc23)n1]

6-Chloro-3-fluoro-N-[6-(1H-indol-4-yl)-1H-indazol-4-yl]-2-pyridinecarboxamide (50 mg, 0.12 mmol) was placed in a microwave vial and dissolved in methylamine (40% weight in water, 1 ml). The mixture was heated at 160° C. for 2 h under microwave irradiation. The solvent was removed under a stream of nitrogen to give a crude residue that was dissolved in DMSO/MeOH (1:1) and purified by Mass Directed Automated Preparative HPLC (Method C). The product was loaded onto a 1 g aminopropyl column, eluted with MeOH and the solvent removed under a stream of nitrogen to give the title compound (4 mg).

LCMS (Method B) $R_t$=0.86 mins, MH$^+$=426.

Example 39

3-(Dimethylamino)-6-(ethylamino)-N-[6-(1H-indol-4-yl)-1H-indazol-4-yl]-2-pyridinecarboxamide

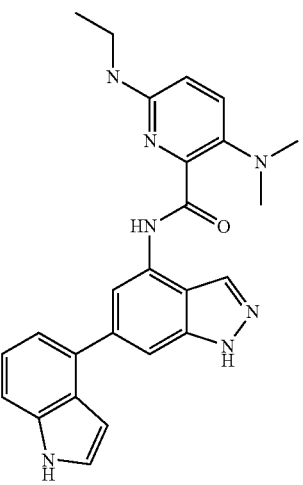 [SMILES: CCNc1ccc(N(C)C)c(C(=O)Nc2cc(-c3cccc4[nH]ccc34)cc3[nH]ncc23)n1]

6-Chloro-3-fluoro-N-[6-(1H-indol-4-yl)-1H-indazol-4-yl]-2-pyridinecarboxamide (50 mg, 0.12 mmol) was placed in a microwave vial and dissolved in ethylamine (70% weight in water, 1 ml). The mixture was heated at 160° C. for 3 h under microwave irradiation. The solvent was removed under a stream of nitrogen to give a crude residue that was dissolved in DMSO/MeOH (1:1) and purified by Mass Directed Automated Preparative HPLC (Method C). The product was loaded onto a 1 g aminopropyl column, eluted with MeOH and the solvent removed under a stream of nitrogen to give the title compound (5 mg) as an orange solid.

LCMS (Method B) $R_t$=0.91 mins, MH$^+$=440.

Example 40

6-Chloro-N-[6-(1H-indol-4-yl)-1H-indazol-4-yl]-3-(4-morpholinyl)-2-pyridinecarboxamide

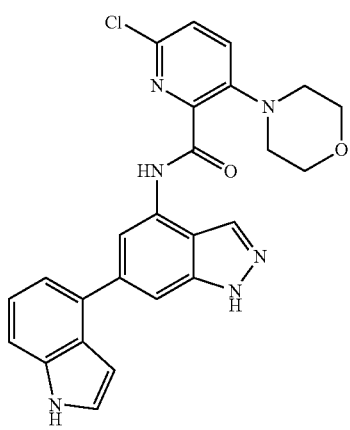 [SMILES: O=C(Nc1cc(-c2cccc3[nH]ccc23)cc2[nH]ncc12)c1nc(Cl)ccc1N1CCOCC1]

6-Chloro-3-fluoro-N-[6-(1H-indol-4-yl)-1H-indazol-4-yl]-2-pyridinecarboxamide (28 mg, 0.07 mmol) was placed in a microwave vial and dissolved in DMSO (1 ml). Morpholine (0.006 ml, 0.07 mmol) and DIPEA (0.07 ml) were added and the mixture was heated at 100° C. for 1 h under microwave irradiation. The crude reaction mixture was purified by Mass Directed Automated Preparative HPLC (Method B) to afford the title compound (5 mg) as a cream solid.

LCMS (Method B) $R_t$=1.03 mins, $MH^+$=473.

Example 41

6-Chloro-N-[6-(1H-indol-4-yl)-1H-indazol-4-yl]-3-(1-piperidinyl)-2-pyridinecarboxamide

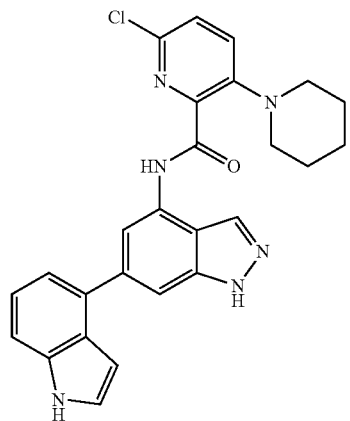 [SMILES: O=C(Nc1cc(-c2cccc3[nH]ccc23)cc2[nH]ncc12)c1nc(Cl)ccc1N1CCCCC1]

To a microwave vial was added 2 ml of a solution of 6-chloro-3-fluoro-N-[6-(1H-indol-4-yl)-1H-indazol-4-yl]-2-pyridinecarboxamide (300 mg, 0.74 mmol) in DMSO (6 ml). Piperidine (0.024 ml, 0.25 mmol) and DIPEA (0.129 ml) were added and the mixture was heated at 160° C. for 2 h under microwave irradiation. The crude reaction mixture was dissolved in DMSO/MeOH (1:1) and purified by Mass Directed Automated Preparative HPLC (Method E). The sample was further purified by Mass Directed Automated Preparative HPLC (Method E) and product-containing fractions were dried under a stream of nitrogen to afford the title compound (16 mg).

LCMS (Method B) $R_t$=1.16 mins, $MH^+$=471.

Example 42

N-[6-(1H-Indol-4-yl)-1H-indazol-4-yl]-5-(4-morpholinyl)-2-pyridinecarboxamide

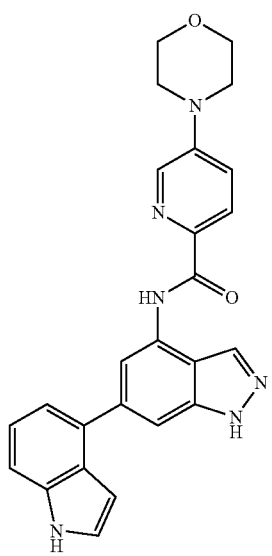 [SMILES: O=C(Nc1cc(-c2cccc3[nH]ccc23)cc2[nH]ncc12)c1ccc(N2CCOCC2)cn1]

5-Bromo-N-[6-(1H-indol-4-yl)-1H-indazol-4-yl]-2-pyridinecarboxamide (35 mg, 0.08 mmol) and morpholine (1 ml, 11.5 mmol) were placed in a microwave vial. $Pd_2dba_3$ (4 mg, 0.004 mmol), BINAP (5 mg, 0.008 mmol) and cesium carbonate (40 mg, 0.12 mmol) were added and the mixture was heated at 150° C. for 75 mins under microwave irradiation. The reaction mixture was concentrated in vacuo to give a crude residue that was suspended in 1:1 DMSO/MeOH (1 ml) and filtered to give an orange solution that was purified by Mass Directed Automated Preparative HPLC (Method C). The product was loaded onto a 1 g aminopropyl column, eluted with MeOH and the solvent removed under a stream of nitrogen to give the title compound (8 mg) as a pale orange solid.

LCMS (Method B) $R_t$=1.01 mins, $MH^+$=439.

Example 43

N-[6-(1H-Indol-4-yl)-1H-indazol-4-yl]-5-(1-piperidinyl)-2-pyridinecarboxamide

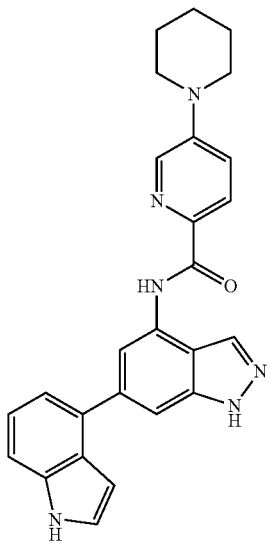 [SMILES: O=C(Nc1cc(-c2cccc3[nH]ccc23)cc2[nH]ncc12)c1ccc(N2CCCCC2)cn1]

5-Bromo-N-[6-(1H-indol-4-yl)-1H-indazol-4-yl]-2-pyridinecarboxamide (50 mg, 0.12 mmol) and piperidine (1 ml, 10.1 mmol) were placed in a microwave vial. $Pd_2dba_3$ (5 mg, 0.006 mmol), BINAP (7.2 mg, 0.012 mmol) and cesium carbonate (57 mg, 0.17 mmol) were added and the mixture was heated at 150° C. for 75 mins under microwave irradiation. The reaction mixture was concentrated in vacuo to give a crude residue that was suspended in 1:1 DMSO/MeOH (1 ml) and filtered to give an orange solution that was purified by Mass Directed Automated Preparative HPLC (Method C). The product was loaded onto a 1 g aminopropyl column, eluted with MeOH and the solvent removed under a stream of nitrogen to give the title compound (18 mg) as a yellow gum.

LCMS (Method B) $R_t$=1.23 mins, $MH^+$=437.

Example 44

3-Chloro-N-[6-(1H-indol-4-yl)-1H-indazol-4-yl]-2-pyridinecarboxamide

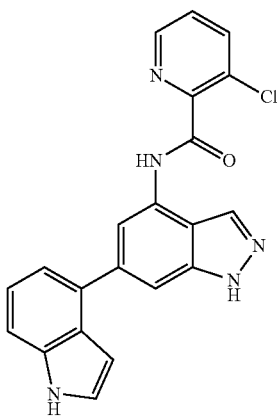 [SMILES: O=C(Nc1cc(-c2cccc3[nH]ccc23)cc2[nH]ncc12)c1ncccc1Cl]

To a solution of 3-chloropicolinic acid (380 mg, 2.42 mmol, available from Fluorochem Ltd.) in DMF (5 ml) was added HATU (920 mg, 2.42 mmol) and DIPEA (1.266 ml, 7.25 mmol). The mixture was stirred at room temperature for 20 mins then 6-(1H-indol-4-yl)-1H-indazol-4-amine (300 mg, 1.21 mmol) was added and the mixture stirred at room temperature overnight. The reaction mixture was concentrated in vacuo to give a volume of approx. 1 ml which was added to the top of a 20 g aminopropyl cartridge that had been preconditioned with MeOH. The reaction mixture remained on the cartridges for 2 h before being eluted with MeOH. The solvent was removed in vacuo to give a brown oil that was purified by chromatography using silica gel (70 g cartridge, FlashMaster II) eluting with 0-25% MeOH in DCM over 30 mins to afford the title compound (130 mg) as a brown solid.

LCMS (Method B) $R_t$=0.94 mins, $MH^+$=388.

Example 45

6-Amino-N-[6-(1H-indol-4-yl)-1H-indazol-4-yl]-2-pyridinecarboxamide

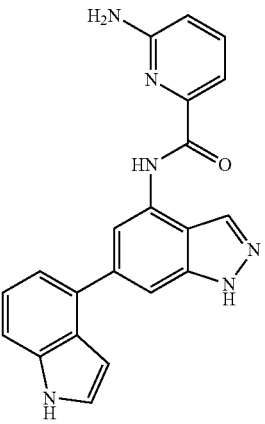 [SMILES: Nc1cccc(C(=O)Nc2cc(-c3cccc4[nH]ccc34)cc3[nH]ncc23)n1]

To a solution of 6-amino-2-pyridinecarboxylic acid (120 mg, 0.89 mmol, available from Apollo Scientific) in DMF (2 ml) was added HATU (340 mg, 0.89 mmol) and DIPEA (0.464 ml, 2.67 mmol). The mixture was stirred at room temperature for 20 mins then 6-(1H-indol-4-yl)-1H-indazol-4-amine (110 mg, 0.44 mmol) was added and the mixture stirred at room temperature overnight. The reaction mixture was applied to the top of a 50 g aminopropyl cartridge that had been preconditioned with DCM/MeOH (1:1). The reaction mixture remained on the cartridges for 2 h before being eluted with DCM/MeOH (1:1). The solvent was removed in vacuo to give a brown oil that was purified by chromatography using silica gel (50 g cartridge, FlashMaster II) eluting with 0-100% ethyl acetate in cyclohexane over 30 mins followed by 0-20% MeOH in ethyl acetate over 10 mins to afford the title compound (26 mg) as a pale yellow gum.

LCMS (Method B) $R_t$=0.92 mins, $MH^+$=369.

Example 46

5-Amino-N-[6-(1H-indol-4-yl)-1H-indazol-4-yl]-2-pyridinecarboxamide

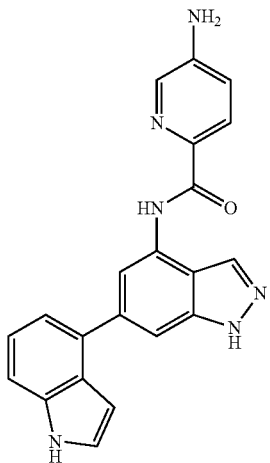 [SMILES: Nc1ccc(C(=O)Nc2cc(-c3cccc4[nH]ccc34)cc3[nH]ncc23)nc1]

To a solution of 5-amino-2-pyridinecarboxylic acid (56 mg, 0.40 mmol, available from ChemPacific) in DMF (2 ml) was added HATU (150 mg, 0.40 mmol) and DIPEA (0.211 ml, 1.21 mmol). The mixture was stirred at room temperature for 20 mins then 6-(1H-indol-4-yl)-1H-indazol-4-amine (50 mg, 0.20 mmol) was added and the mixture stirred at room temperature for 18 h. The reaction mixture was added to the top of a 20 g aminopropyl cartridge that had been preconditioned with MeOH. The reaction mixture remained on the cartridges for 3 h before being eluted with MeOH. The solvent was removed in vacuo to give a crude residue that was dissolved in DMSO/MeOH (1:1) and purified by Mass Directed Automated Preparative HPLC (Method C). The product was loaded onto a 1 g aminopropyl column, eluted with DCM/MeOH (1:1) and the solvent removed under a stream of nitrogen to give the title compound (28 mg) as a white solid.

LCMS (Method B) $R_t$=0.90 min, $MH^+$=369.

Example 47

N-[6-(1H-Indol-4-yl)-1H-indazol-4-yl]-5-methyl-2-pyridinecarboxamide

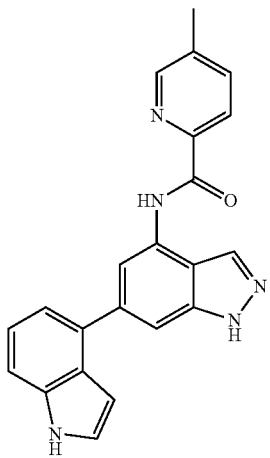 [SMILES: Cc1ccc(C(=O)Nc2cc(-c3cccc4[nH]ccc34)cc3[nH]ncc23)nc1]

To a solution of 5-methyl-2-pyridinecarboxylic acid (55 mg, 0.40 mmol, available from Synchem OHG) in DMF (2 ml) was added HATU (150 mg, 0.40 mmol) and DIPEA (0.211 ml, 1.21 mmol). The mixture was stirred at room temperature for 20 mins then 6-(1H-indol-4-yl)-1H-indazol-4-amine (50 mg, 0.20 mmol) was added and the mixture stirred at room temperature for 18 h. The reaction mixture was added to the top of a 2 g aminopropyl cartridge that had been preconditioned with MeOH. The reaction mixture remained on the cartridges for 3 h before being eluted with MeOH. The solvent was removed in vacuo to give a crude residue that was dissolved in DMSO/MeOH (1:1) and purified by Mass Directed Automated Preparative HPLC (Method C). The product was loaded onto a 1 g aminopropyl column, eluted with DCM/MeOH (1:1) and the solvent removed under a stream of nitrogen to give the title compound (20 mg) as a cream solid.

LCMS (Method B) $R_t$=1.08 min, $MH^+$=368.

Example 48

N-[6-(1H-Indol-4-yl)-1H-indazol-4-yl]-2-methyl-3-pyridinecarboxamide

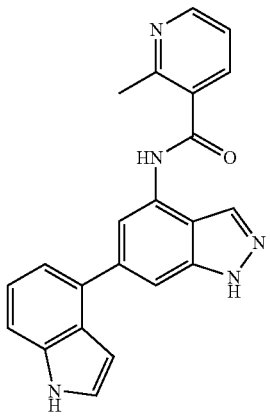 [SMILES: Cc1ncccc1C(=O)Nc1cc(-c2cccc3[nH]ccc23)cc2[nH]ncc12]

To a solution of 2-methylnicotinic acid (55 mg, 0.40 mmol) in DMF (2 ml) was added HATU (150 mg, 0.40 mmol) and DIPEA (0.211 ml, 1.21 mmol). The mixture was stirred at room temperature for 20 mins then 6-(1H-indol-4-yl)-1H-indazol-4-amine (50 mg, 0.20 mmol) was added and the mixture was stirred at room temperature for 18 h. The reaction mixture was added to the top of a 20 g aminopropyl cartridge that had been pre-conditioned with MeOH. The reaction mixture remained on the cartridges for 3 h before being eluted with MeOH. The solvent was removed in vacuo to give a crude residue that was dissolved in DMSO/MeOH (1:1) and purified by Mass Directed Automated Preparative HPLC (Method E). The sample was further purified using Mass Directed Automated Preparative HPLC (Method E) and product-containing fractions were dried under a stream of nitrogen to give the title compound (19 mg) as a pale yellow solid.

LCMS (Method B) $R_t$=0.83 min, $MH^+$=368.

Example 49

3-Amino-N-[6-(1H-indol-4-yl)-1H-indazol-4-yl]-2-pyridinecarboxamide

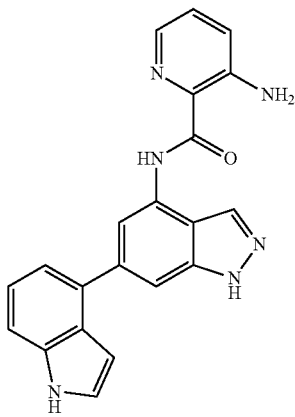 [SMILES: Nc1cccnc1C(=O)Nc1cc(-c2cccc3[nH]ccc23)cc2[nH]ncc12]

To a solution of 3-amino-2-pyridinecarboxylic acid (56 mg, 0.40 mmol, available from Apollo Scientific) in DMF (2 ml) was added HATU (150 mg, 0.40 mmol) and DIPEA (0.211 ml, 1.21 mmol). The mixture was stirred at room temperature for 20 mins then 6-(1H-indol-4-yl)-1H-indazol-4-amine (50 mg, 0.20 mmol) was added and the mixture stirred at room temperature for 18 h. The reaction mixture was added to the top of a 20 g aminopropyl cartridge that had been preconditioned with MeOH. The reaction mixture remained on the cartridges for 3 h before being eluted with MeOH. The solvent was removed in vacuo to give a crude residue that was dissolved in DMSO/MeOH (1:1) and purified by Mass Directed Automated Preparative HPLC (Method C). The product was loaded onto a 1 g aminopropyl column, eluted with MeOH and the solvent removed under a stream of nitrogen to give the title compound (9 mg) as a pale yellow solid.

LCMS (Method B) $R_t$=1.03 min, $MH^+$=369.

Example 50

N-[6-(1H-Indol-4-yl)-1H-indazol-4-yl]-4-(methylamino)-2-pyridinecarboxamide

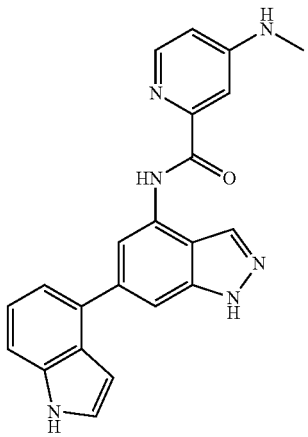 [SMILES: CNc1ccnc(C(=O)Nc2cc(-c3cccc4[nH]ccc34)cc3[nH]ncc23)c1]

To a solution of 4-(methylamino)pyridine-2-carboxylic acid (61 mg, 0.40 mmol, available from Zerenex Molecular Ltd) in DMF (2 ml) was added HATU (150 mg, 0.40 mmol) and DIPEA (0.211 ml, 1.21 mmol). The mixture was stirred at room temperature for 30 mins then 6-(1H-indol-4-yl)-1H-indazol-4-amine (50 mg, 0.20 mmol) was added and the mixture stirred at room temperature for 18 h. The reaction mixture was added to the top of a 10 g aminopropyl cartridge that had been pre-conditioned with MeOH. The reaction mixture remained on the cartridges for 2 h before being eluted with MeOH. The solvent was removed in vacuo to give a crude residue that was dissolved in DMSO/MeOH (1:1) and purified by Mass Directed Automated Preparative HPLC (Method C). The product was loaded onto a 1 g aminopropyl column, eluted with MeOH and the solvent removed under a stream of nitrogen to give the title compound (17 mg) as a cream solid.

LCMS (Method B) $R_t$=0.78 min, $MH^+$=383.

Example 51

N-[6-(1H-Indol-4-yl)-1H-indazol-4-yl]-2-pyridinecarboxamide

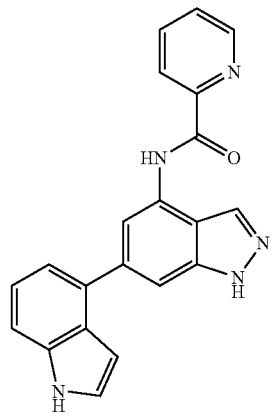 [SMILES: O=C(Nc1cc(-c2cccc3[nH]ccc23)cc2[nH]ncc12)c1ccccn1]

A mixture of N-(6-bromo-1H-indazol-4-yl)-2-pyridinecarboxamide (38 mg, 0.12 mmol), 1H-indol-4-ylboronic acid (23 mg, 0.14 mmol, available from Apollo), Pd(dppf)Cl$_2$ (10 mol %, 12 mg, 0.015 mmol), aqueous sodium carbonate solution (2M, 0.18 ml, 0.36 mmol) in dioxane/water 1:1 (2 ml) was heated at 150° C. for 30 mins under microwave irradiation. The reaction mixture was filtered through a silica cartridge eluting with MeOH, then the solvent was removed in vacuo. Purification by mass directed preparative HPLC (Method B) give after evaporation of solvents the title compound as a light brown solid (21 mg).

LCMS (Method B) $R_1$=0.97 min, $MH^+$=354.

Example 52

N-[6-(1H-Indol-6-yl)-1H-indazol-4-yl]-2-pyridinecarboxamide

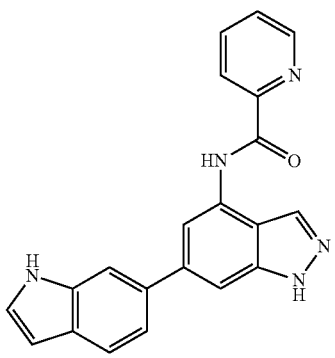 [SMILES: O=C(Nc1cc(-c2ccc3cc[nH]c3c2)cc2[nH]ncc12)c1ccccn1]

A mixture of N-(6-bromo-1H-indazol-4-yl)-2-pyridinecarboxamide (70 mg, 0.22 mmol), 1H-indol-6-ylboronic acid (42 mg, 0.26 mmol), Pd(dppf)Cl$_2$ (10 mol %, 22 mg, 0.027 mmol), aqueous sodium carbonate solution (2M, 0.328 ml, 0.656 mmol) in dioxane/water 1:1 (3 ml) was heated at 150° C. for 15 mins under microwave irradiation. The reaction mixture was filtered through a silica cartridge eluting with MeOH. The solvent was removed in vacuo. The crude compound obtained was purified by mass directed preparative HPLC (Method B) to afford the title compound (9 mg).

LCMS (Method A) R$_t$=3.35 min, MH$^+$=354.

Example 53

N-[6-(1-Methyl-1H-indol-5-yl)-1H-indazol-4-yl]-2-pyridinecarboxamide

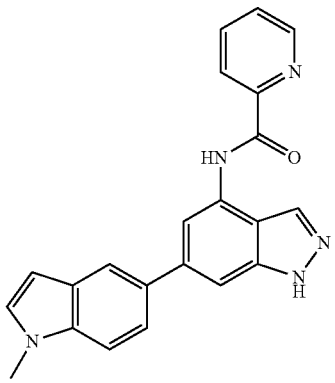 [SMILES: Cn1ccc2cc(-c3cc(NC(=O)c4ccccn4)c4cn[nH]c4c3)ccc21]

A mixture of N-(6-bromo-1H-indazol-4-yl)-2-pyridinecarboxamide (100 mg, 0.31 mmol), (1-methyl-1H-indol-5-yl)boronic acid (65 mg, 0.37 mmol, available from Apollo), Pd(dppf)Cl$_2$ (10 mol %, 31 mg, 0.038 mmol), aqueous sodium carbonate solution (2M, 0.468 ml, 0.94 mmol) in dioxane/water 1:1 (3 ml) was heated at 150° C. for 30 mins under microwave irradiation. The reaction mixture was filtered through a silica cartridge eluting with MeOH. The solvent was removed in vacuo. The crude compound obtained was purified by HPLC using the following conditions to provide the title compound (15 mg).

Column: C18 HPLC Supelcosil ABZ PLUS column 10 cm×21.2 mm, 5 micron
Solvent A: H$_2$O+0.1% TFA
Solvent B: MeCN+0.1% TFA
Gradient: 30-80% of B over 10 min
LCMS (Method A) R$_t$=3.45 min, MH$^+$=368.

Example 54

N-[6-(1H-Indol-4-yl)-1H-indazol-4-yl]-2-(methyloxy)-3-pyridinecarboxamide

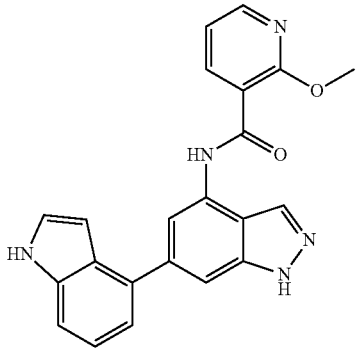 [SMILES: COc1ncccc1C(=O)Nc1cc(-c2cccc3[nH]ccc23)cc2[nH]ncc12]

2-(Methyloxy)-3-pyridinecarboxylic acid (33 mg, 0.22 mmol) was treated with HATU (84 mg, 0.22 mmol) in DMF (0.25 ml) and DIPEA (0.069 ml, 0.40 mmol). The reaction mixture was shaken for 5 mins prior to treatment with 6-(1H-indol-4-yl)-1H-indazol-4-amine (25 mg, 0.1 mmol) in DMF (0.25 ml) and then left to stand at room temperature for 18 h. Solvent was removed in vacuo and the product re-dissolved in chloroform (0.3 ml) prior to application on to a pre-conditioned (methanol then chloroform) aminopropyl SPE cartridge (0.5 g). Product was eluted after 2 h with ethyl acetate/methanol (1:1, 3 ml), and concentrated under a stream of nitrogen using blow down apparatus. Purification by MDAP (Method D) afforded the title compound (2 mg).

LCMS (Method B) R$_t$=1.06 min; MH$^+$=384.

Similarly prepared was:

| Example Number | Structure | Name | Precursor acid | LCMS Rt (min) | MH+ |
|---|---|---|---|---|---|
| 55 | 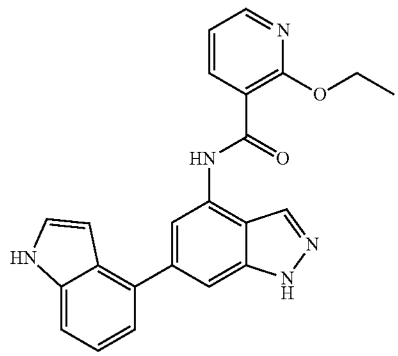 [SMILES: CCOc1ncccc1C(=O)Nc1cc(-c2cccc3[nH]ccc23)cc2[nH]ncc12] | 2-(ethyloxy)-N-[6-(1H-indol-4-yl)-1H-indazol-4-yl]-3-pyridinecarboxamide | 2-(ethyloxy)-3-pyridinecarboxylic acid | 1.12 | 398 |

Example 56

5-Bromo-N-[6-(1H-indol-4-yl)-1H-indazol-4-yl]-2-pyridinecarboxamide

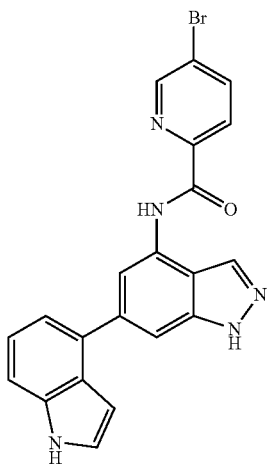 [SMILES: O=C(Nc1cc(-c2cccc3[nH]ccc23)cc2[nH]ncc12)c1ccc(Br)cn1]

To a solution of 5-bromo-2-pyridinecarboxylic acid (980 mg, 4.83 mmol, available from Alfa Aesar) in DMF (15 ml) was added HATU (1840 mg, 4.83 mmol) and DIPEA (2.53 ml, 14.50 mmol). The mixture was stirred at room temperature for 30 mins then 6-(1H-indol-4-yl)-1H-indazol-4-amine (600 mg, 2.41 mmol) was added and the mixture stirred at room temperature overnight. The reaction mixture was concentrated in vacuo to approx. 5 ml volume and was applied to 2×50 g aminopropyl cartridges that had been pre-conditioned with MeOH. The reaction mixture remained on the cartridges for 2 h before being eluted with MeOH. The eluent was concentrated in vacuo and a precipitate formed, which was collected by filtration to give the title compound (430 mg) as a yellow solid.

LCMS (Method B) $R_t$=1.12 mins, MH+=433.

Example 57

N-[6-(1H-Indol-4-yl)-1H-indazol-4-yl]-2-(1-pyrrolidinyl)-4-pyridinecarboxamide

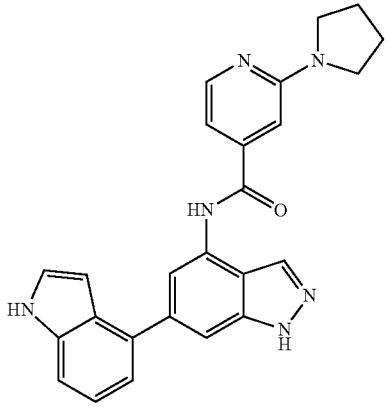 [SMILES: O=C(Nc1cc(-c2cccc3[nH]ccc23)cc2[nH]ncc12)c1ccnc(N2CCCC2)c1]

A solution of 2-(1-pyrrolidinyl)-4-pyridinecarboxylic acid hydrochloride (38 mg, 0.16 mmol, available from Maybridge) in anhydrous THF (2 ml), was treated with 1-chloro-N,N,2-trimethyl-1-propen-1-amine (0.026 ml, 0.2 mmol, available from Acros) and stirred at room temperature under nitrogen for 2 h. The mixture was then treated with anhydrous DIPEA (0.131 ml, 0.75 mmol) followed by a solution of 6-(1H-indol-4-yl)-2-(tetrahydro-2H-pyran-2-yl)-2H-indazol-4-amine (50 mg, 0.15 mmol) in THF (2 ml). The mixture was stirred under nitrogen for a further 6 h. Solvents were removed by blow down under a stream of nitrogen and the residue was then dissolved in methanol (3 ml) and evaporated further in a vacuum centrifuge. The residue was then dissolved in methanol (5 ml) then treated with macroporous tosic acid (102 mg, 0.452 mmol) and stirred for 17 h at room temperature. Addition of 0.88 ammonia solution (0.5 ml) was followed by stirring at room temperature for a further 30 mins and then the mixture was separated using a hydrophobic frit. The organic layer was concentrated in vacuo and the residue purified by HPLC (Method E) to afford the title compound (8 mg).

LCMS (Method B) $R_t$=0.86 min, MH+=423.

Similarly prepared were:

| Example Number | Structure | Name | Precursor acid | LCMS Rt (min) | MH+ |
|---|---|---|---|---|---|
| 58 | 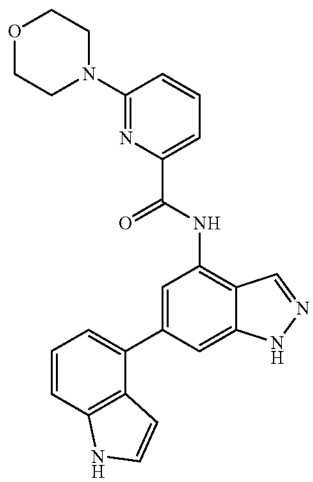 [SMILES: O=C(Nc1cc(-c2cccc3[nH]ccc23)cc2[nH]ncc12)c1cccc(N2CCOCC2)n1] | N-[6-(1H-indol-4-yl)-1H-indazol-4-yl]-6-(4-morpholinyl)-2-pyridinecarboxamide | 6-(4-morpholinyl)-2-pyridinecarboxylic acid (Maybridge) | 1.07 | 439 |
| 59 | 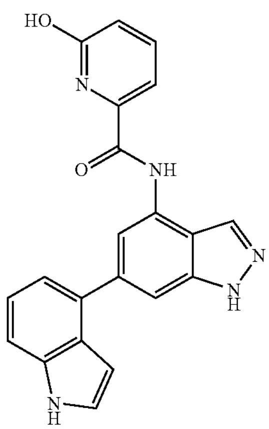 [SMILES: O=C(Nc1cc(-c2cccc3[nH]ccc23)cc2[nH]ncc12)c1cccc(O)n1] | N-[6-(1H-indol-4-yl)-1H-indazol-4-yl]-6-oxo-1,6-dihydro-2-pyridinecarboxamide | 6-oxo-1,6-dihydro-2-pyridinecarboxylic acid | 0.80 | 370 |
| 60 | 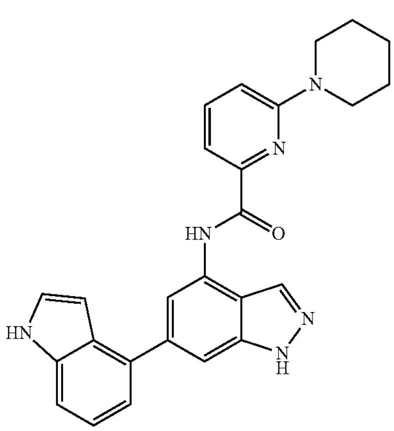 [SMILES: O=C(Nc1cc(-c2cccc3[nH]ccc23)cc2[nH]ncc12)c1cccc(N2CCCCC2)n1] | N-[6-(1H-indol-4-yl)-1H-indazol-4-yl]-2-(1-pyrrolidinyl)-4-pyridinecarboxamide | 6-(1-piperidinyl)-2-pyridinecarboxylic acid (Maybridge) | 1.28 | 437 |

Example 61

N-[6-(1H-Indol-4-yl)-1-methyl-1H-indazol-4-yl]-6-methyl-2-pyridinecarboxamide

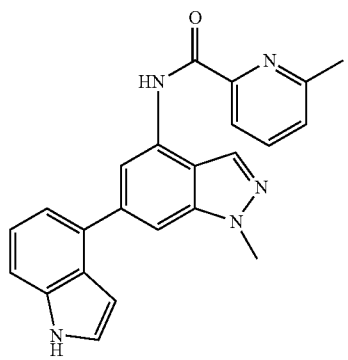 [SMILES: Cc1cccc(C(=O)Nc2cc(-c3cccc4[nH]ccc34)cc3c2cnn3C)n1]

A mixture of N-(6-bromo-1-methyl-1H-indazol-4-yl)-6-methyl-2-pyridinecarboxamide (50 mg, 0.14 mmol), indole-4-boranepinacoloate ester (40 mg, 0.18 mmol, commercially available), Pd(dppf)Cl$_2$ (22 mg, 0.03 mmol) and sodium carbonate (2M aqueous, 0.26 ml) in 1,4-dioxane (2 ml) was heated to 150° C. under microwave conditions for 10 minutes. The mixture was extracted with dichloromethane (2×15 ml) and concentrated in vacuo and the residue was purified by HPLC (Method B) to afford the title compound (23 mg).

LCMS (Method B) R$_t$=1.19 min, MH$^+$=382.

Example 62

N-[6-(1H-Indol-4-yl)-1H-indazol-4-yl]-3-(1-methylethenyl)-2-pyridinecarboxamide

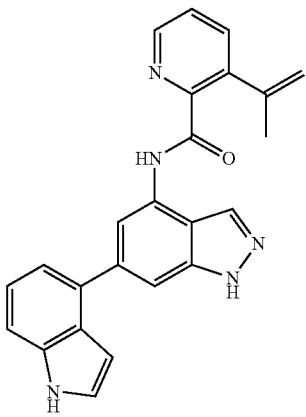 [SMILES: C=C(C)c1cccnc1C(=O)Nc1cc(-c2cccc3[nH]ccc23)cc2[nH]ncc12]

3-Bromo-N-[6-(1H-indol-4-yl)-1H-indazol-4-yl]-2-pyridinecarboxamide (0.25 g, 0.58 mmol) and isopropenylboronic acid pincaol ester (available from Aldrich, 0.12 ml, 0.64 mmol) were placed in a microwave vial and dissolved in 1,4-dioxane (4 ml). Pd(PPh$_3$)$_4$ (66 mg, 0.06 mmol) and Na$_2$CO$_3$ (0.58 ml, 1.16 mmol, 2 M aqueous solution) were added and the mixture was heated at 150° C. for 10 mins under microwave irradiation. The reaction mixture was filtered through Celite, washing with ethyl acetate. The organic mixture was washed with water (10 ml) and brine (10 ml), dried over MgSO$_4$, filtered and the solvent was removed in vacuo. The resulting orange solid was purified by mass-directed automated preparative HPLC (Method B) to give the title compound as a white solid.

LC/MS (Method B) R$_t$ 1.04 mins, m/z 394 [M+H]$^+$.

Example 63

N-[6-(1H-Indol-4-yl)-1H-indazol-4-yl]-3-(1-methylethyl)-2-pyridinecarboxamide

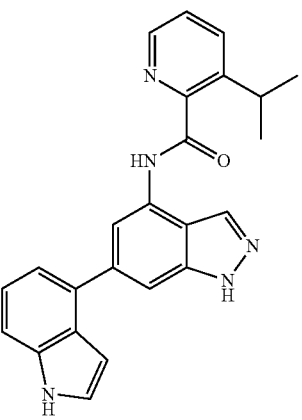 [SMILES: CC(C)c1cccnc1C(=O)Nc1cc(-c2cccc3[nH]ccc23)cc2[nH]ncc12]

N-[6-(1H-Indol-4-yl)-1H-indazol-4-yl]-3-(1-methylethenyl)-2-pyridinecarboxamide (166 mg, 0.42 mmol, prepared as described in Example 62) was dissolved in ethanol and hydrogenated at 25° C. on the H-cube using a 5% palladium on carbon catalyst. The mixture was passed through the flow reactor twice then the catalyst was replaced before the mixture was passed through another two times. The solvent was removed in a stream of nitrogen to give a pale yellow oil. This was purified by mass-directed automated preparative HPLC (Method B) to give the title compound (17 mg) as a white solid.

LC/MS (Method B) R$_t$ 1.11 mins, m/z 396 [M+H]$^+$.

Example 64

N-[6-(1H-Indol-4-yl)-1H-indazol-4-yl]-6-(tetrahydro-2H-pyran-4-yloxy)-2-pyridinecarboxamide

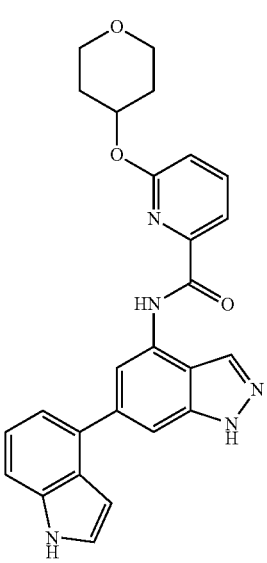 [SMILES: O=C(Nc1cc(-c2cccc3[nH]ccc23)cc2[nH]ncc12)c1cccc(OC2CCOCC2)n1]

Under an atmosphere of nitrogen, sodium hydride (5 mg, 0.14 mmol, 60% suspension in mineral oil) was added to a solution of tetrahydro-2H-pyran-4-ol (13 mg, 0.14 mmol) in THF (2 ml). After hydrogen evolution was complete, 6-Fluoro-N-[6-(1H-indol-4-yl)-1H-indazol-4-yl]-2-pyridinecarboxamide (50 mg, 0.14 mmol) was added and the mixture was heated to reflux for 1 h. Another portion of tetrahydro-2H-pyran-4-ol (13 mg, 0.14 mmol) and sodium hydride (5 mg, 0.14 mmol) was added and the mixture was heated to reflux overnight. The mixture was cooled to room temperature, water was added and the mixture was extracted with DCM. The organic extracts were combined, dried over MgSO$_4$, filtered and the solvent was removed in vacuo to give an orange oil. This was purified by mass-directed automated preparative HPLC (Method B) to give the title compound (7 mg) as a white solid.

LC/MS (Method B) R$_t$ 1.08 mins, m/z 454 [M+H]$^+$.

Example 65

N-[6-(1H-Indol-4-yl)-1H-indazol-4-yl]-6-[(4-methyl-1-piperazinyl)methyl]-2-pyridinecarboxamide

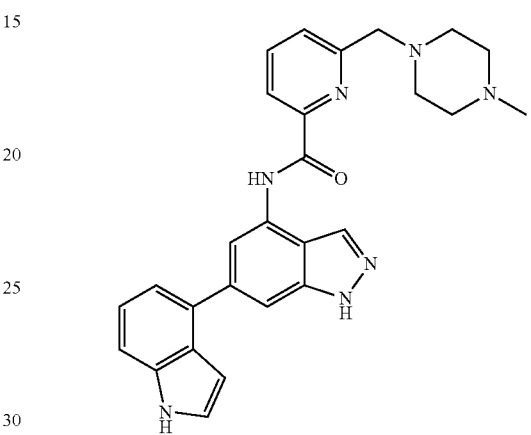

A solution of 6-[(4-methyl-1-piperazinyl)methyl]-2-pyridinecarboxylic acid (35 mg, 0.15 mmol) in DMF (0.8 ml) was treated with HATU (72 mg, 0.19 mmol) and DIPEA (0.052 ml, 0.30 mmol). After 5 minutes the resulting solution was added to 6-(1H-indol-4-yl)-2-(tetrahydro-2H-pyran-2-yl)-2H-indazol-4-amine (33 mg, 0.10 mmol) and the resulting mixture was stirred at room temperature for 17 h. The mixture was washed with saturated sodium bicarbonate (10 ml) and extracted with dichloromethane (3×10 ml). Organic fractions were dried by passage through a hydrophobic frit and combined. The solvent was evaporated under a nitrogen stream. The crude material was dissolved in methanol (2 ml) and hydrochloric acid (0.080 ml, 0.16 mmol) was added. The solution was evaporated under a nitrogen stream. The crude product was purified by Mass Directed AutoPrep method B. Solvents of the different fractions were evaporated under a stream of nitrogen. Further purification of the crude sample by Mass Directed AutoPrep method B was performed. All fractions still contained an impurity. Solvent was blown down under a nitrogen stream and fractions were combined again and purified by Mass Directed Auto Prep using the following conditions:

5 um Supelco ABZ+plus 100×21.2 mm ID column eluting with a gradient of solvents A/B (A: 0.05% v/v solution of trifluoroacetic acid in water, B: 0.05% v/v trifluoroacetic acid in acetonitrile).

The appropriate fractions were combined to give the title compound as a gum.

LCMS (Method B) m/z 466 [MH$^+$], R$_t$=0.83 mins.

Example 66

N-[3-Fluoro-6-(1H-indol-4-yl)-1H-indazol-4-yl]-3-methyl-2-pyridinecarboxamide

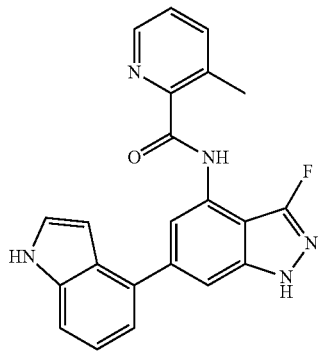 [SMILES: Cc1cccnc1C(=O)Nc1cc(-c2cccc3[nH]ccc23)cc2[nH]nc(F)c12]

To 3-Methyl-2-pyridinecarboxylic acid (0.032 g, 0.234 mmol) in DMF (0.5 ml) was added HATU (0.089 g, 0.234 mmol) and the solution stirred for 10 min at 20° C. To this was then added a solution of 3-fluoro-6-(1H-indol-4-yl)-1H-indazol-4-amine (0.052 g, 0.195 mmol) in DMF (0.5 ml), followed by DIPEA (0.068 ml, 0.391 mmol) and the top was placed on the vial which had been pierced with a needle. The mixture was stirred at 20° C. for 66 hours then loaded directly onto a dry 1 g NH2 cartridge, left for 2 hours then eluted with methanol (2.5 column vols). Upon standing for 20 hours at 20° C., a solid precipitated from the orange solution which was filtered off and dried. The solid was triturated with methanol (2×2 ml) then blown to dryness and loaded onto a 500 mg SCX pre-rinsed with methanol. Elution with methanol (3 column vols) then 2M NH3/MeOH (3 column vols) and concentration of the basic fractions by blow down afforded the title compound (6 mg).

LC/MS $R_t$ 3.08 min m/z 386 [MH$^+$]. Method A

Example 67

6-[(4,4-Dimethyl-1-piperidinyl)methyl]-N-[6-(1H-indol-4-yl)-1H-indazol-4-yl]-2-pyridinecarboxamide trifluoroacetate

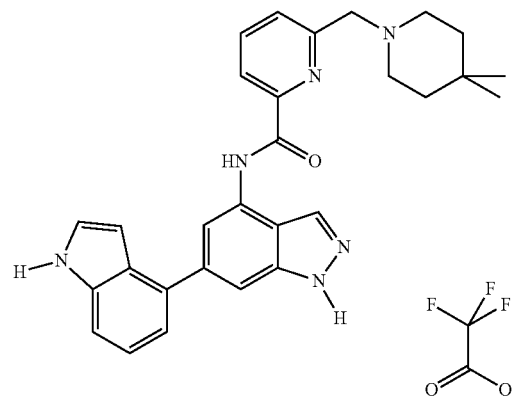 [SMILES: CC1(C)CCN(Cc2cccc(C(=O)Nc3cc(-c4cccc5[nH]ccc45)cc4[nH]ncc34)n2)CC1 ; O=C(O)C(F)(F)F]

A solution of 6-(chloromethyl)-N-[6-(1H-indol-4-yl)-1-(phenylsulfonyl)-1H-indazol-4-yl]-2-pyridinecarboxamide (50 mg, 0.092 mmol) in acetonitrile (0.5 ml) was added to 4,4-dimethylpiperidine hydrochloride (0.11 mmol, available from Microchemistry Ltd). DIPEA was then added (0.026 ml, 0.15 mmol), followed by sodium iodide (13 mg). The vial was capped and the stirred solution heated to 70° C. for 18 h. After this time, acetonitrile was removed by blow down. Isopropanol (0.5 ml) was then added, followed by sodium hydroxide solution (0.5 ml (2M, aqueous)) and the mixture was stirred for 18 h at room temperature. The solution was then neutralised using standard methods and the solvents were removed by blowdown. The residue was dissolved in DMF/Acetone/Water (0.2 ml:0.2 ml:20 µl) and purified by Mass Directed AutoPrep HPLC (Method F). The solvent was removed in vacuo by vacuum centrifugation to give the title compound (24 mg).

LCMS (Method B) $R_t$=0.77 min, MH$^+$=479.

Similarly prepared were:

| Example Number | Structure | Name | Precursor amine | LCMS Rt (min) | MH+ |
|---|---|---|---|---|---|
| 68 | (structure shown) | 6-[(3,3-dimethyl-1-piperidinyl)methyl]-N-[6-(1H-indol-4-yl)-1H-indazol-4-yl]-2-pyridinecarboxamide trifluoroacetate | 3,3-dimethyl-piperidine hydrochloride (available from Manchester Organics) | 0.75 | 479 |

-continued

| Example Number | Structure | Name | Precursor amine | LCMS Rt (min) | MH+ |
|---|---|---|---|---|---|
| 69 | 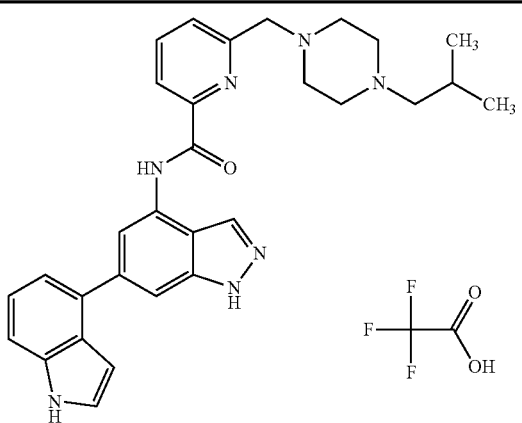 | N-[6-(1H-indol-4-yl)-1H-indazol-4-yl]-6-{[4-(2-methylpropyl)-1-piperazinyl]methyl}-2-pyridinecarboxamide trifluoroacetate | 1-(2-methylpropyl) piperazine (available from Fluorochem) | 0.74 | 508 |
| 70 | 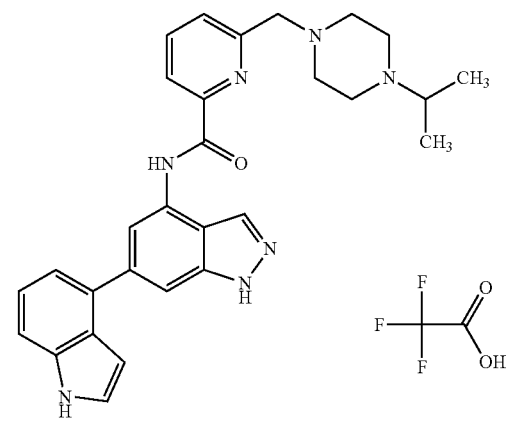 [SMILES: CC(C)N1CCN(Cc2cccc(C(=O)Nc3cc(-c4cccc5[nH]ccc45)cc4[nH]ncc34)n2)CC1 ; O=C(O)C(F)(F)F] | N-[6-(1H-indol-4-yl)-1H-indazol-4-yl]-6-{[4-(1-methylethyl)-1-piperazinyl]methyl}-2-pyridinecarboxamide trifluoroacetate | 1-(1-methylethyl) piperazine (available from ABCR) | 0.7 | 494 |
| 71 | 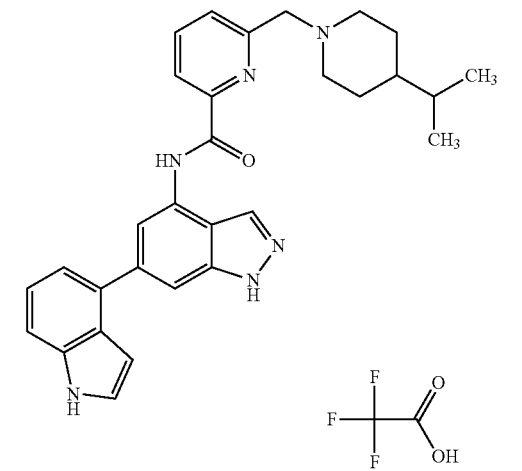 [SMILES: CC(C)C1CCN(Cc2cccc(C(=O)Nc3cc(-c4cccc5[nH]ccc45)cc4[nH]ncc34)n2)CC1 ; O=C(O)C(F)(F)F] | N-[6-(1H-indol-4-yl)-1H-indazol-4-yl]-6-{[4-(1-methylethyl)-1-piperidinyl]methyl}-2-pyridinecarboxamide trifluoroacetate | 4-(1-methylethyl) piperidine (available from Chembridge Building Blocks) | 0.81 | 493 |

-continued

| Example Number | Structure | Name | Precursor amine | LCMS Rt (min) | MH+ |
|---|---|---|---|---|---|
| 72 | 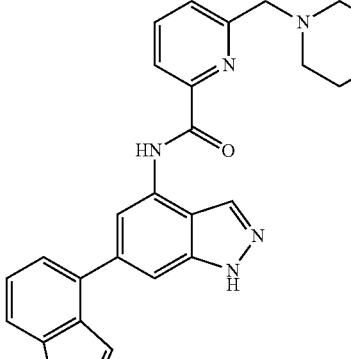 | N-[6-(1H-indol-4-yl)-1H-indazol-4-yl]-6-({4-[2-(4-morpholinyl)ethyl]-1-piperazinyl}methyl)-2-pyridinecarboxamide trifluoroacetate | 4-[2-(1-piperazinyl)ethyl] morpholine (available from ABCR) | 0.56 | 565 |
| 73 | 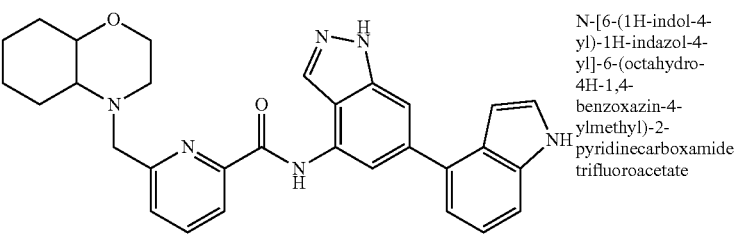 | N-[6-(1H-indol-4-yl)-1H-indazol-4-yl]-6-(octahydro-4H-1,4-benzoxazin-4-ylmethyl)-2-pyridinecarboxamide trifluoroacetate | octahydro-2H-1,4-benzoxazine (available from Chemical Block Ltd) | 0.74 | 507 |
| 74 | 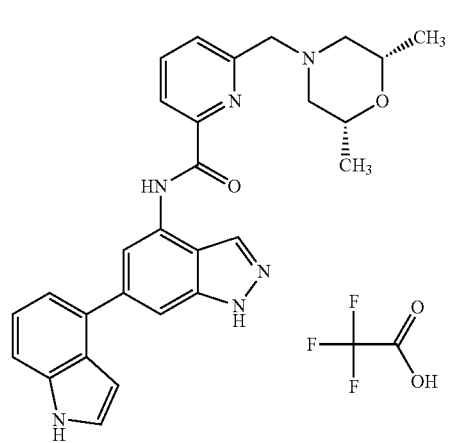 [SMILES: C[C@@H]1CN(Cc2cccc(C(=O)Nc3cc(-c4cccc5[nH]ccc45)cc4[nH]ncc34)n2)C[C@H](C)O1 ; O=C(O)C(F)(F)F] | 6-{[(2R,6S)-2,6-dimethyl-4-morpholinyl]methyl}-N-[6-(1H-indol-4-yl)-1H-indazol-4-yl]-2-pyridinecarboxamide trifluoroacetate | (2R,6S)-2,6-dimethyl-morpholine (available from ABCR) | 0.71 | 481 |

-continued

| Example Number | Structure | Name | Precursor amine | LCMS Rt (min) | MH+ |
|---|---|---|---|---|---|
| 75 | 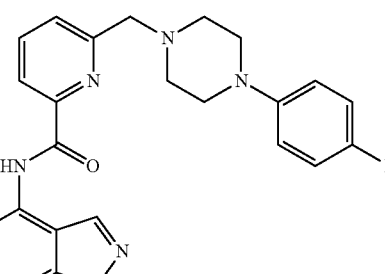 | 6-{[4-(4-fluorophenyl)-1-piperazinyl]methyl}-N-[6-(1H-indol-4-yl)-1H-indazol-4-yl]-2-pyridinecarboxamide trifluoroacetate | 1-(4-fluorophenyl) piperazine dihydrochloride (available from ABCR) | 0.81 | 546 |
| 76 | 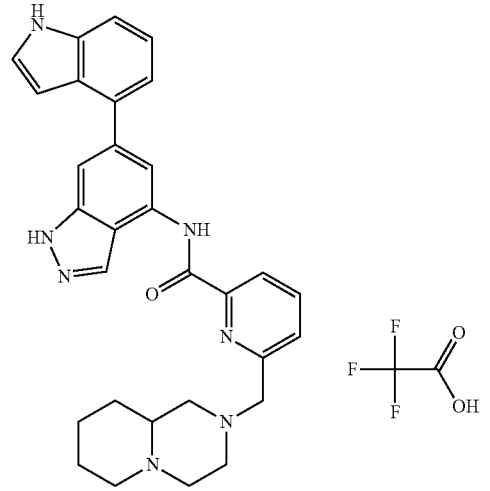 [SMILES: O=C(Nc1cc(-c2cccc3[nH]ccc23)cc2[nH]ncc12)c1cccc(CN2CCN3CCCCC3C2)n1 ; O=C(O)C(F)(F)F] | N-[6-(1H-indol-4-yl)-1H-indazol-4-yl]-6-(octahydro-2H-pyrido[1,2-a]pyrazin-2-ylmethyl)-2-pyridinecarboxamide trifluoroacetate | octahydro-2H-pyrido[1,2-a] pyrazine (available from ABCR) | 0.71 | 506 |
| 77 | 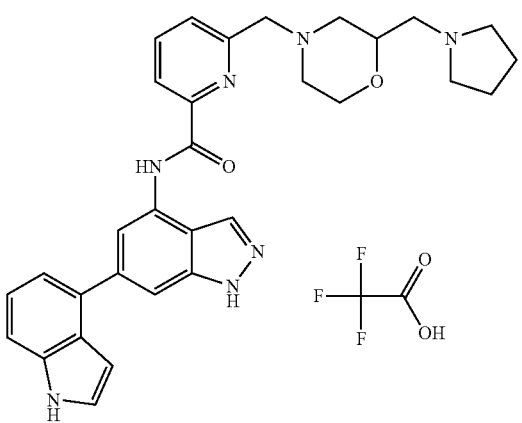 [SMILES: O=C(Nc1cc(-c2cccc3[nH]ccc23)cc2[nH]ncc12)c1cccc(CN2CCOC(CN3CCCC3)C2)n1 ; O=C(O)C(F)(F)F] | N-[6-(1H-indol-4-yl)-1H-indazol-4-yl]-6-{[2-(1-pyrrolidinylmethyl)-4-morpholinyl]methyl}-2-pyridinecarboxamide trifluoroacetate | 2-(1-pyrrolidinyl-methyl) morpholine (available from J&W PharmLab) | 0.59 | 536 |

-continued

| Example Number | Structure | Name | Precursor amine | LCMS Rt (min) | MH+ |
|---|---|---|---|---|---|
| 78 | 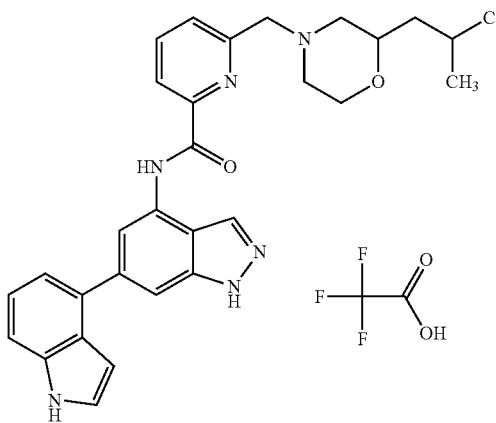 | N-[6-(1H-indol-4-yl)-1H-indazol-4-yl]-6-{[2-(2-methylpropyl)-4-morpholinyl]methyl}-2-pyridinecarboxamide trifluoroacetate | 2-(2-methylpropyl) morpholine (available from Chembridge Building Blocks) | 0.8 | 509 |
| 79 | 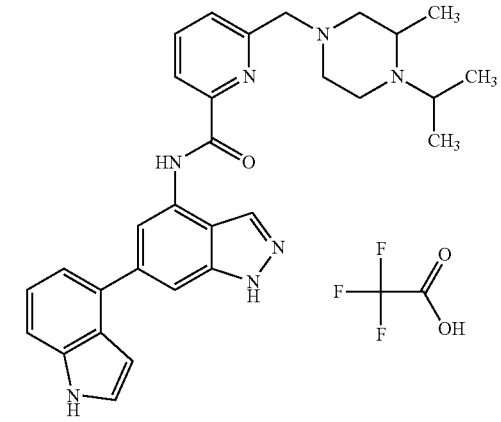 [SMILES: CC(C)N1CCN(Cc2cccc(C(=O)Nc3cc(-c4cccc5[nH]ccc45)cc4[nH]ncc34)n2)CC1C ; O=C(O)C(F)(F)F] | N-[6-(1H-indol-4-yl)-1H-indazol-4-yl]-6-{[3-methyl-4-(1-methylethyl)-1-piperazinyl]methyl}-2-pyridinecarboxamide trifluoroacetate | 2-methyl-1-(1-methylethyl) piperazine (available from Fluorochem) | 0.72 | 508 |
| 80 | 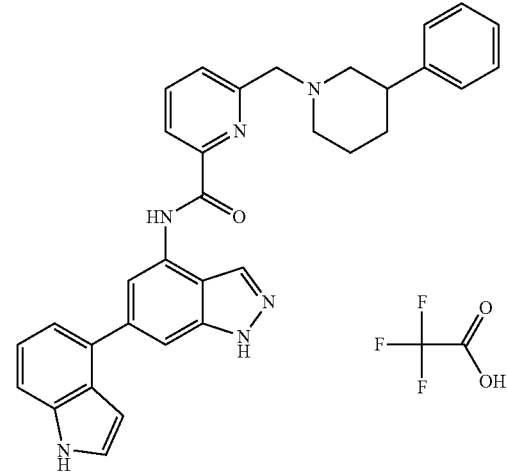 [SMILES: O=C(Nc1cc(-c2cccc3[nH]ccc23)cc2[nH]ncc12)c1cccc(CN2CCCC(c3ccccc3)C2)n1 ; O=C(O)C(F)(F)F] | N-[6-(1H-indol-4-yl)-1H-indazol-4-yl]-6-[(3-phenyl-1-piperidinyl)methyl]-2-pyridinecarboxamide trifluoroacetate | 3-phenylpiperidine (available from ABCR) | 0.81 | 527 |

-continued

| Example Number | Structure | Name | Precursor amine | LCMS Rt (min) | MH+ |
|---|---|---|---|---|---|
| 81 | 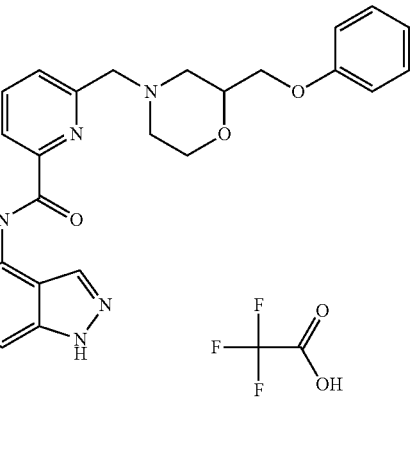 | N-[6-(1H-indol-4-yl)-1H-indazol-4-yl]-6-({2-[(phenyloxy)methyl]-4-morpholinyl}methyl)-2-pyridinecarboxamide trifluoroacetate | 2-[(phenyloxy)methyl]morpholine (available from J&W PharmLab) | 0.82 | 559 |
| 82 | 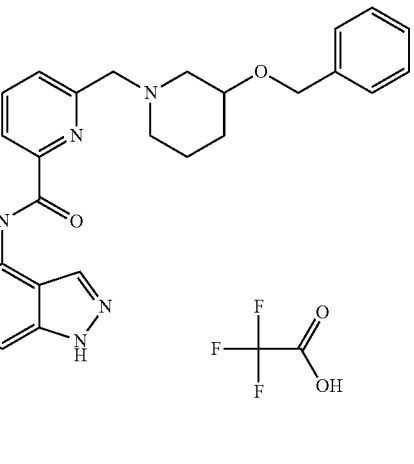 | N-[6-(1H-indol-4-yl)-1H-indazol-4-yl]-6-({3-[(phenylmethyl)oxy]-1-piperidinyl}methyl)-2-pyridinecarboxamide trifluoroacetate | 3-[(phenylmethyl)oxy]piperidine (available from ASDI International) | 0.8 | 557 |
| 83 | 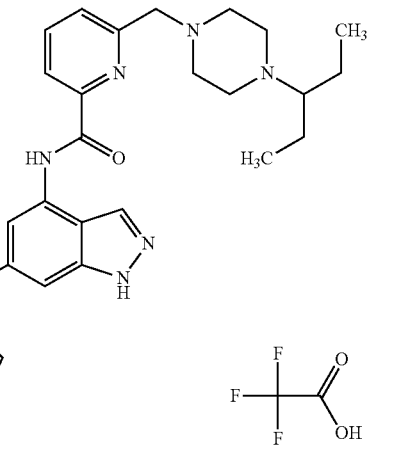 | 6-{[4-(1-ethylpropyl)-1-piperazinyl]methyl}-N-[6-(1H-indol-4-yl)-1H-indazol-4-yl]-2-pyridinecarboxamide trifluoroacetate | 1-(1-ethylpropyl)piperazine (available from Fluorochem) | 0.75 | 522 |

| Example Number | Structure | Name | Precursor amine | LCMS Rt (min) | MH+ |
|---|---|---|---|---|---|
| 84 | 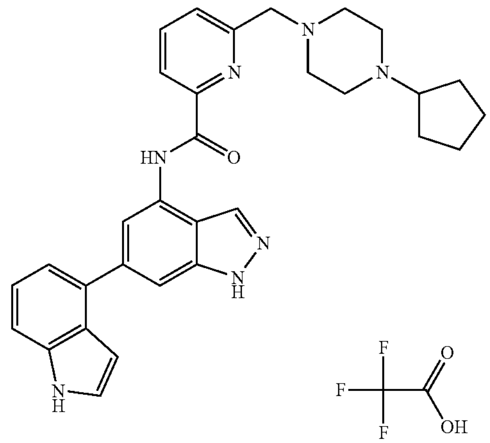 [SMILES: O=C(Nc1cc(-c2cccc3[nH]ccc23)cc2[nH]ncc12)c1cccc(CN2CCN(C3CCCC3)CC2)n1 ; O=C(O)C(F)(F)F] | 6-[(4-cyclopentyl-1-piperazinyl)methyl]-N-[6-(1H-indol-4-yl)-1H-indazol-4-yl]-2-pyridinecarboxamide trifluoroacetate | 1-cyclopentyl-piperazine (available from ABCR) | 0.73 | 520 |

Example 85

6-Methyl-N-[1-methyl-6-(1H-pyrrolo[2,3-b]pyridin-4-yl)-1H-indazol-4-yl]-2-pyridinecarboxamide

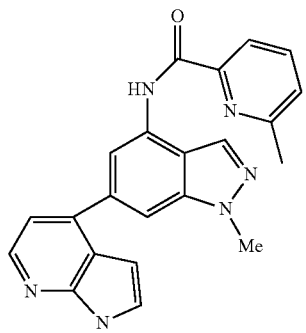 [SMILES: Cc1cccc(C(=O)Nc2cc(-c3ccnc4[nH]ccc34)cc3c2cnn3C)n1]

6-Methyl-2-pyridinecarboxylic acid (32 mg, 0.234 mmol) and (1-chloro-2-methyl-1-propen-1-yl)dimethylamine (0.031 mL, 0.234 mmol) were added to dichloromethane (5 mL) and stirred for 10 minutes. This mixture was added to a stirred solution of 1-methyl-6-{1-[(4-methylphenyl)sulfonyl]-1H-pyrrolo[2,3-b]pyridin-4-yl}-1H-indazol-4-amine (75 mg, 0.180 mmol) and pyridine (0.029 mL, 0.359 mmol) in dichloromethane (5 mL) under nitrogen and stirred for 7 days. Only starting material remained so using a new bottle, (1-chloro-2-methyl-1-propen-1-yl)dimethylamine (0.031 mL, 0.234 mmol) and 6-methyl-2-pyridinecarboxylic acid (32 mg, 0.234 mmol) were added to dichloromethane (5 mL) under nitrogen and stirred for 10 min. The resultant mixture was added to the reaction mixture, and stirring continued for 30 min. A further portion each of (1-chloro-2-methyl-1-propen-1-yl)dimethylamine (0.031 mL, 0.234 mmol) and 6-methyl-2-pyridinecarboxylic acid (32.0 mg, 0.234 mmol) were then added to dichloromethane (5 mL) under nitrogen and stirred for 10 min. The resultant mixture was added to the reaction mixture, and stirring continued for 30 min, then solvents were removed in vacuo. The crude product (349 mg) was presumed to be 6-methyl-N-(1-methyl-6-{1-[(4-methylphenyl)sulfonyl]-1H-pyrrolo[2,3-b]pyridin-4-yl}-1H-indazol-4-yl)-2-pyridinecarboxamide and this was used directly without further purification. To 6-methyl-N-(1-methyl-6-{1-[(4-methylphenyl)sulfonyl]-1H-pyrrolo[2,3-b]pyridin-4-yl}-1H-indazol-4-yl)-2-pyridinecarboxamide (349 mg, crude) was added potassium trimethyl silanolate (115 mg, 0.650 mmol) and THF (6 mL) under nitrogen and the mixture was heated at 50° C. overnight. A further portion of potassium trimethyl silanolate (230 mg, 1.3 mmol) was then added and heating and stirring continued. The conversion was monitored by LCMS and when the reaction was deemed complete, the reaction mixture was cooled to room temperature and partitioned between water (30 mL) and DCM (30 mL). The organics were concentrated in vacuo and the residue was purified by column chromatography on silica using Flashmaster II technology (100 g Si cartridge, 40 minute gradient of cyclohexane/ethylacetate 0-100%, 0-20% MeOH) to afford the title compound (37 mg).

LCMS (Method B) $R_t$=0.92 min, MH$^+$=383.

Example 86

Formic acid-6-(4-morpholinylmethyl)-N-[6-(1H-pyrrolo[2,3-b]pyridin-4-yl)-1H-indazol-4-yl]-2-pyridinecarboxamide (1:1)

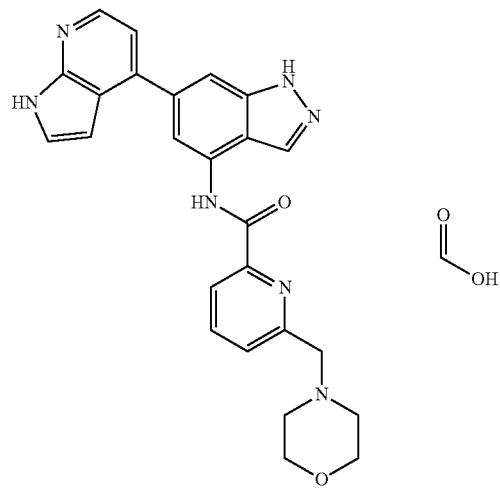 [SMILES: O=C(Nc1cc(-c2ccnc3[nH]ccc23)cc2[nH]ncc12)c1cccc(CN2CCOCC2)n1 ; O=CO]

6-(Chloromethyl)-N-[1-(phenylsulfonyl)-6-(1H-pyrrolo[2,3-b]pyridin-4-yl)-1H-indazol-4-yl]-2-pyridinecarboxamide (0.05 g, 0.09 mmol) was dissolved in MeCN (0.5 ml) and added to a vessel containing morpholine (0.1 mmol). DIPEA (0.026 ml, 0.15 mmol) and sodium iodide (0.015 g, 0.1 mmol) were then added and the mixture was heated to 70° C. for 18 hr. Potassium trimethylsilanolate (0.5 mmol, 0.063 g), dissolved in THF (0.25 ml) was then added and the mixture was heated at 50° C. for 24 hrs. After cooling the solution was quenched with aqueous MeCN (50:50, 1 ml) and neutralised. Solvent was removed in a blowdown unit. The sample was then dissolved in DMF (200 µl), Acetone (200 µl) and water (20 µl) and purified by Mass Directed AutoPrep HPLC (Method F). The solvent was removed in vacuo using the Genevac to give the title compound (14 mg).

LCMS (Method B) $R_t$=0.48 min, MH$^+$=454.

Similarly prepared were:

| Example number | Structure | Name | Precursor amine | LCMS Rt (min) | MH+ |
|---|---|---|---|---|---|
| 87 | 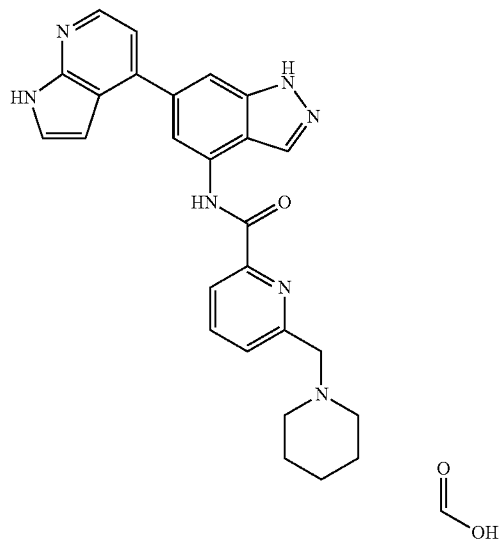 [SMILES: O=C(Nc1cc(-c2ccnc3[nH]ccc23)cc2[nH]ncc12)c1cccc(CN2CCCCC2)n1 ; O=CO] | formic acid - 6-(1-piperidinylmethyl)-N-[6-(1H-pyrrolo[2,3-b]pyridin-4-yl)-1H-indazol-4-yl]-2-pyridinecarboxamide (1:1) | Piperidine | 0.52 | 452 |
| 88 | 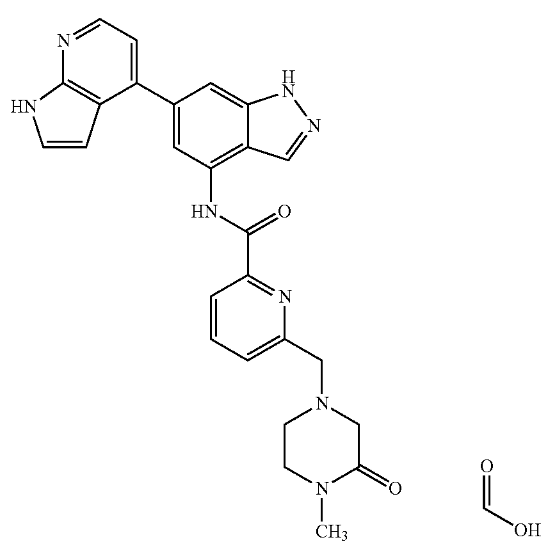 [SMILES: CN1CCN(Cc2cccc(C(=O)Nc3cc(-c4ccnc5[nH]ccc45)cc4[nH]ncc34)n2)CC1=O ; O=CO] | formic acid - 6-[(4-methyl-3-oxo-1-piperazinyl)methyl]-N-[6-(1H-pyrrolo[2,3-b]pyridin-4-yl)-1H-indazol-4-yl]-2-pyridinecarboxamide (1:1) | 1-methyl-2-piperazinone (available from Zerenex Molecular Ltd) | 0.55 | 481 |

| Example number | Structure | Name | Precursor amine | LCMS Rt (min) | MH+ |
|---|---|---|---|---|---|
| 89 | 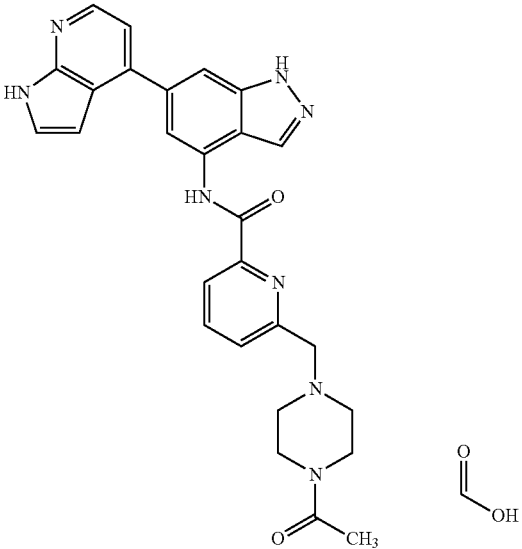 [SMILES: CC(=O)N1CCN(Cc2cccc(C(=O)Nc3cc(-c4ccnc5[nH]ccc45)cc4[nH]ncc34)n2)CC1 ; O=CO] | formic acid - 6-[(4-acetyl-1-piperazinyl)methyl]-N-[6-(1H-pyrrolo[2,3-b]pyridin-4-yl)-1H-indazol-4-yl]-2-pyridinecarboxamide (1:1) | 1-acetyl-piperazine (available from ABCR) | 0.48 | 495 |
| 90 | 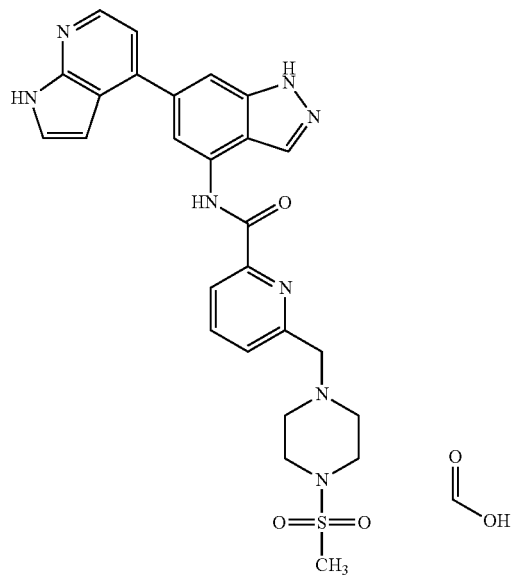 [SMILES: CS(=O)(=O)N1CCN(Cc2cccc(C(=O)Nc3cc(-c4ccnc5[nH]ccc45)cc4[nH]ncc34)n2)CC1 ; O=CO] | formic acid - 6-{[4-(methylsulfonyl)-1-piperazinyl]methyl}-N-[6-(1H-pyrrolo[2,3-b]pyridin-4-yl)-1H-indazol-4-yl]-2-pyridinecarboxamide (1:1) | 1-methylsulfonyl)piperazine (available from TCI-Europe) | 0.54 | 531 |

-continued

| Example number | Structure | Name | Precursor amine | LCMS Rt (min) | MH+ |
| --- | --- | --- | --- | --- | --- |
| 91 | 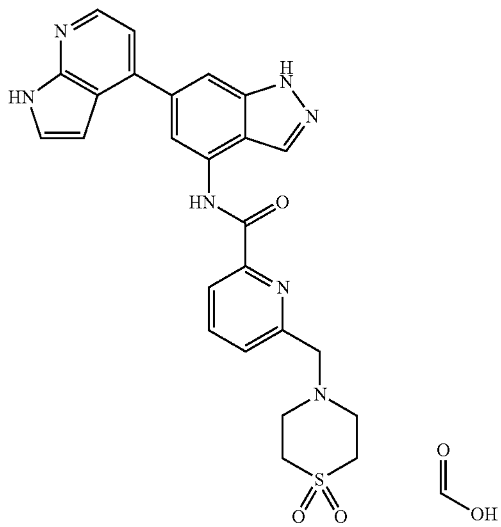 [SMILES: O=C(Nc1cc(-c2ccnc3[nH]ccc23)cc2[nH]ncc12)c1cccc(CN2CCS(=O)(=O)CC2)n1 ; O=CO] | formic acid - 6-[(1,1-dioxido-4-thiomorpholinyl)methyl]-N-[6-(1H-pyrrolo[2,3-b]pyridin-4-yl)-1H-indazol-4-yl]-2-pyridinecarboxamide (1:1) | thiomorpholine 1,1-dioxide (available from TCI-Europe) | 0.65 | 502 |
| 92 | 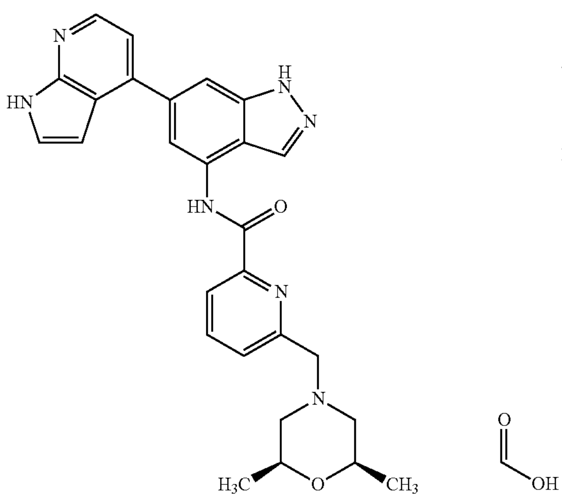 [SMILES: C[C@@H]1CN(Cc2cccc(C(=O)Nc3cc(-c4ccnc5[nH]ccc45)cc4[nH]ncc34)n2)C[C@H](C)O1 ; O=CO] | formic acid - 6-{[(2R,6S)-2,6-dimethyl-4-morpholinyl]methyl}-N-[6-(1H-pyrrolo[2,3-b]pyridin-4-yl)-1H-indazol-4-yl]-2-pyridinecarboxamide (1:1) | (2R,6S)-2,6-dimethyl-morpholine (available from ABCR) | 0.54 | 482 |
| 93 | 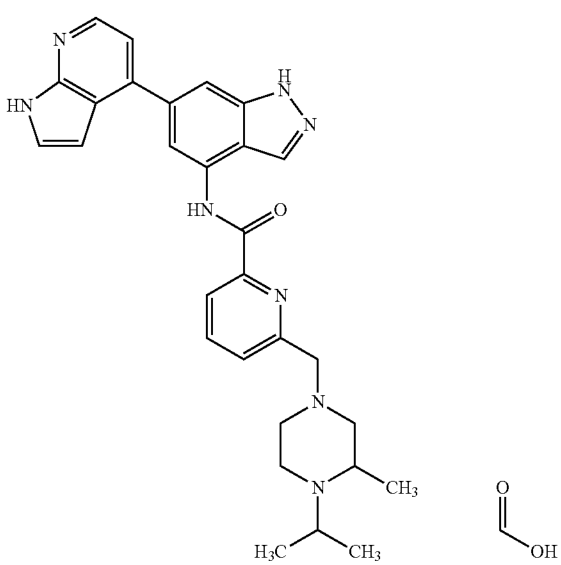 [SMILES: CC(C)N1CCN(Cc2cccc(C(=O)Nc3cc(-c4ccnc5[nH]ccc45)cc4[nH]ncc34)n2)CC1C ; O=CO] | formic acid - 6-{[3-methyl-4-(1-methylethyl)-1-piperazinyl]methyl}-N-[6-(1H-pyrrolo[2,3-b]pyridin-4-yl)-1H-indazol-4-yl]-2-pyridinecarboxamide (1:1) | 2-methyl-1-(1-methylethyl) piperazine (available from Fluorochem) | 0.56 | 509 |

| Example number | Structure | Name | Precursor amine | LCMS Rt (min) | MH+ |
|---|---|---|---|---|---|
| 94 | 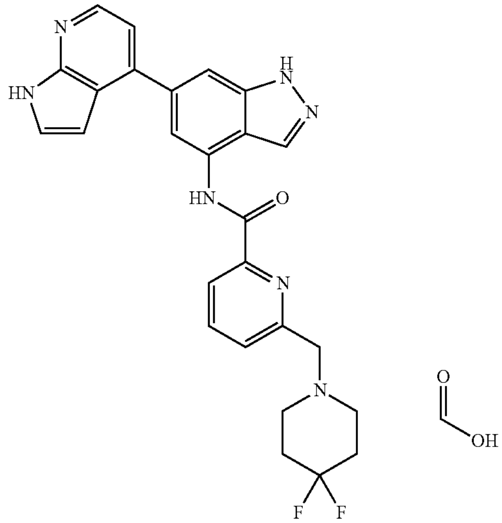 [SMILES: O=C(Nc1cc(-c2ccnc3[nH]ccc23)cc2[nH]ncc12)c1cccc(CN2CCC(F)(F)CC2)n1 ; O=CO] | formic acid - 6-[(4,4-difluoro-1-piperidinyl)methyl-N-[6-(1H-pyrrolo[2,3-b]pyridin-4-yl)-1H-indazol-4-yl]-2-pyridinecarboxamide (1:1) | 4,4-difluoro-piperidine (available from Chem Collect Ltd) | 0.56 | 488 |

Example 95

Formic acid-6-(4-morpholinylmethyl)-N-[6-(1H-pyrazolo[3,4-b]pyridin-5-yl)-1H-indazol-4-yl]-2-pyridinecarboxamide (1:1)

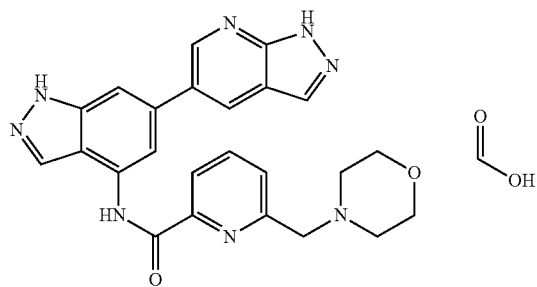 [SMILES: O=C(Nc1cc(-c2cnc3[nH]ncc3c2)cc2[nH]ncc12)c1cccc(CN2CCOCC2)n1 ; O=CO]

6-(Chloromethyl)-N-{1-(phenylsulfonyl)-6-[1-(phenylsulfonyl)-1H-pyrazolo[3,4-b]pyridin-5-yl]-1H-indazol-4-yl}-2-pyridinecarboxamide (0.05 g, 0.09 mmol) was dissolved in MeCN (0.5 ml) and added to a vessel containing morpholine (0.1 mmol). DIPEA (0.026 ml, 0.15 mmol) and sodium iodide (0.015 g, 0.1 mmol) were then added and the mixture was heated to 70° C. for 18 hr. Potassium trimethylsilanolate (0.5 mmol, 0.063 g), dissolved in THF (0.25 ml) was then added and the mixture was heated at 50° C. for 24 hrs. After cooling the solution was quenched with aqueous MeCN (50:50, 1 ml) and neutralised. Solvent was removed in a blowdown unit. The sample was then dissolved in DMF (200 µl), Acetone (200 µl) and water (20 µl) and purified by Mass Directed AutoPrep HPLC (Method F). The solvent was removed in vacuo using the Genevac to give the title compound (5 mg).

LCMS (Method B) $R_t$=0.52 min, MH+=455.

Similarly prepared were:

| Example number | Structure | Name | Precursor amine | LCMS Rt (min) | MH+ |
|---|---|---|---|---|---|
| 96 | 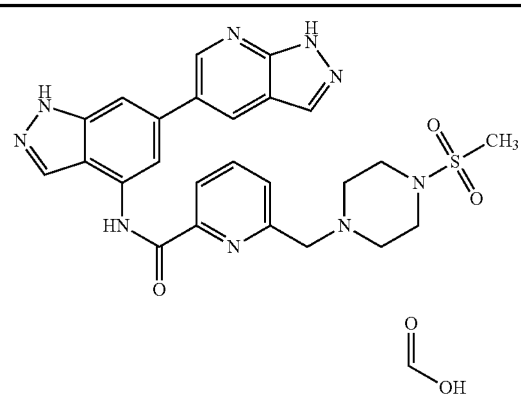 | formic acid - 6-{[4-(methylsulfonyl)-1-piperazinyl]methyl}-N-[6-(1H-pyrazolo[3,4-b]pyridin-5-yl)-1H-indazol-4-yl]-2-pyridinecarboxamide (1:1) | 1-(methylsulfonyl) piperazine (available from TCI-Europe) | 0.56 | 532 |

-continued

| Example number | Structure | Name | Precursor amine | LCMS Rt (min) | MH+ |
|---|---|---|---|---|---|
| 97 | 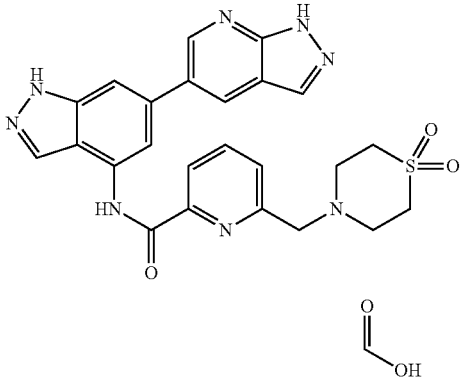 | formic acid - 6-[(1,1-dioxido-4-thiomorpholinyl)methyl]-N-[6-(1H-pyrazolo[3,4-b]pyridin-5-yl)-1H-indazol-4-yl]-2-pyridinecarboxamide (1:1) | thiomorpholine 1,1-dioxide (available from TCI-Europe) | 0.70 | 503 |
| 98 | 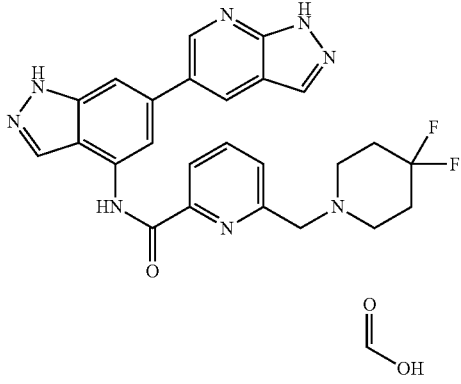 [SMILES: O=C(Nc1cc(-c2cnc3[nH]ncc3c2)cc2[nH]ncc12)c1cccc(CN2CCC(F)(F)CC2)n1 ; O=CO] | formic acid - 6-[(4,4-difluoro-1-piperidinyl)methyl]-N-[6-(1H-pyrazolo[3,4-b]pyridin-5-yl)-1H-indazol-4-yl]-2-pyridinecarboxamide (1:1) | 4,4-difluoro-piperidine (available from Chem Collect Ltd) | 0.59 | 489 |
| 99 | 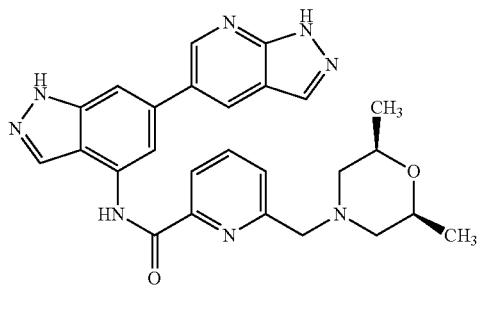 | formic acid - 6-{[(2R,6S)-2,6-dimethyl-4-morpholinyl]methyl}-N-[6-(1H-pyrazolo[3,4-b]pyridin-5-yl)-1H-indazol-4-yl]-2-pyridinecarboxamide (1:1) | (2R,6S)-2,6-dimethylmorpholine (available from ABCR) | 0.58 | 483 |
| 100 | 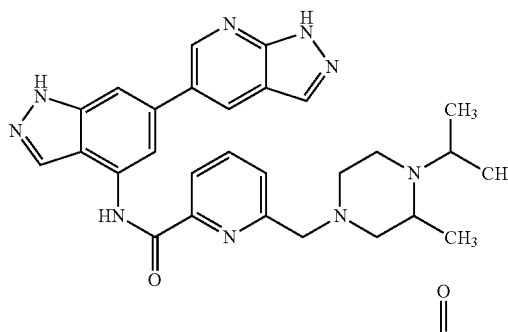 | formic acid - 6-{[3-methyl-4-(1-methylethyl)-1-piperazinyl]methyl}-N-[6-(1H-pyrazolo[3,4-b]pyridin-5-yl)-1H-indazol-4-yl]-2-pyridinecarboxamide (1:1) | 2-methyl-1-(1-methylethyl)piperazine (available from Fluorochem) | 0.60 | 510 |

Biological Data
Determination of AKT Phosphorylation in Expanded T Cells Using Flow Cytometry
Assay Principle The assay measures the single cell phosphorylation of AKT in response to co stimulation of CD3/CD28 on expanded T cells with anti CD3 and anti CD28. Intracellular protein phosphorylation is analysed using a Beckman Coulter FC500 microplate loading (MPL) flow cytometer, after labelling with fluorochrome conjugated phospho protein specific antibodies. In this case intracellular phosphorylated AKT was labelled with monoclonal antibodies to phospho-AKT S473 directly conjugated to Alexa 488. Light scatter versus fluorescence scatter plots are made and AKT phosphorylation is detected as an increase in % of activated (pAKT) cells.

Assay Protocol
Cell Plating

Remove expanded T cells from flasks (See appendix below). Centrifuge and remove supernatant. Re-suspend pellet in warm (37C) stimulation buffer (RPMI containing pen/strep/glutamine and 5% FCS) and centrifuge again. Re-suspend pellet in 10-20 mls of warm stimulation buffer and count. Adjust cell concentration to $1 \times 10^6$ cells/ml. Add 45 ul of cell suspension to wells of v bottomed polystyrene plates and incubate at 37C for 90 minutes.

Prepare stimulant plate containing anti CD3 (BDBiosciences #555329) and anti CD28 (BD Biosiences # 555725). Require 1-0.7 ug of each antibody per well. Stock antibody solutions are at 1000 ug/ml. Add an appropriate volume of diluted antibody solution to each well. Addition of 5 ul of this stock solution to cells results in a final concentration of 1-0.7 ug of each antibody per well.

Compound Plate Preparation and Stimulant Addition

Add serial (1/3) diluted compounds in wells A1-H10 (columns 11 and 12 contained stimulated and un-stimulated cells respectively). Top concentration is 10 uM and resulting final DMSO concentration is 0.15% DMSO. These steps are usually automated using a Beckman Coulter Biomek FX. Positive control is also included in plate sets (as a bundle). Positive control used in this assay is GW450853X (LY294002). Make up stock solutions of compounds at 6.66M and serially dilute it by 1 in 3 with 100% DMSO (8-span Biomek FX). Make plate replicates (stamp out) required number of plates. Each well contains 0.75 ul of compound at 6.666M in 100% DMSO (Use Biomek automation protocol). Dilute serially diluted stock compounds to 100 uM by adding 49.25 ul of stimulation buffer.

A further 1/10 dilution will result in a top concentration of 10 uM containing 0.15% DMSO. In this case 5 ul of each diluted compound is added to plates containing 50 ul of rested cell suspension. Columns 11 and 12 contain stimulation buffer and DMSO only.

Cell Treatments

Set up Biomek deck with compound plates and tip boxes as required. Place cell plates in appropriate deck locations on the Biomek FX. Start Biomek Program transfer 5 ul of each compound to cell plates. Following addition of compounds each plate is shaken gently (600 rpm) for 5 seconds. Once finished, place lids on plates and transfer them to a carbon dioxide incubator. Incubate in the presence of compound for 30 mins.

Cell Stimulation

Set up Biomek FX as per automation protocol. Place stimulation plate on deck. Place cell plates in position and add stimulant. Remove plates and place back in incubator for 19.25 minutes (total stimulation time is 20 mins)

Cell Fixation

Set up Biomek deck as per Cell fixation protocol. Pour pre warmed fixative (4% buffered paraformaldehyde solution or BD Cytofix reagent) into reservoir and place on heated deck (temperature maintained at 37 deg C.). Centrifuge plates for 5 mins at 1000 g. Remove fixative supernatant by pipetteing using Biomek FX. Break up pellets by vortexing wells. This is performed by simply sweeping the bottom on the plates over a whirlymixer.

Arrange a large tray of ice (capable of holding several pates). Arrange plates on the ice and add 200 ul of ice-cold 90% methanol to each well. Cover and leave on ice for 30 minutes. Centrifuge plates at 1000 g for 5 minutes and remove methanol solution. Vortex plates and wash with 100 ul of PBS. Centrifuge again for 5 mins at 1000 g. Remove supernatant and vortex pellet Add 50 ul of Alexa fluor 488 Phospho-Akt (Ser 473) phospho specific rabbit monoclonal antibody (CST #2336) solution (1/100 dilution of stock anti body in stain solution). Cover plates and incubate in the dark for 60 minutes. Centrifuge plates (1000 g for 5 mins), remove supernatant and wash once using stain buffer. Re-suspend pellet in 180 ul of stain buffer (PBS, 2.5% FCS, 0.02% NaN3) Analyze plates using the FC500 MPL flow cytometer.

Appendix:
T Cell Expansion
Coating of Tissue Culture Plates for Stimulation

Add 1.5 ml of PBS containing 1 mM MgCl2, 1 mM CaCl2, anti CD3 5 ug/ml and anti CD28 5 ug/ml to each well of 6 well Costar Tissue culture plate and incubate overnight at 37 deg C. in a CO2 incubator. This will coat the plate with the mAb's.

Wash the wells of the Costar plates once with 3 ml/well of PBS.

Re-suspend the PBMCs at $2 \times 10^6$ cells/ml in the growth media with IL-2 (10 ng/ml, R&D Systems # 202-IL) and PHA (2 ug/ml, Sigma # L2769). Add 3 mls of the cell suspension to each well of a six well culture dish (Costar). Incubate the plate at 37 deg C. in a CO2 incubator until they are confluent i.e. the medium turns yellow.

After four days, wash the stimulated lymphocytes from culture wells using growth media. Culture lymphocytes in growth media (RPMI GIBCO CT 5615 10% Heat inactivated FCS, Hyclone, 2 mM Glutamine GIBCO, 1% Pen/Strep GIBCO, 1% Non essential amino acids, GIBCO, 1% Sodium Pyruvate, GIBCO, 20 uM Hepes GIBCO, 1.75 ul/500 mls 2-mercaptoethanol, Sigma] in a medium size flask (T75) at a concentration of $\sim 10^6$/ml with IL-2 (10 ng/ml) and IL-7 (1 ng/ml, R&D Systems # 207-IL). Allow the cells to expand in resting phase at 37° C. in a CO2 incubator for 4-7 days. During this period of expansion, check cell growth every day and top up with 10 to 15 ml of resting media with IL-2 (10 ng/ml) and IL-7 (1 ng/ml) depending on how confluent the growth is. If required transfer cells to larger flask (T175). $1 \times 10^6$/ml cells are stained with Propidium Iodide and analysed by flow cytometry. Apoptotic cells are excluded from viable cell counts for subsequent experiments. Cells should be >80% viable for use.

PI3K Alpha, Beta, Delta and Gamma Assays
Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3kinase activity competes for the binding site on the PH domain, resulting in a loss of energy transfer and a decrease in signal.

Assay Protocol

Solid compounds are typically plated with 0.1 µl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat# 33-001)

The assay kit consist of the following:
4×PI3K reaction buffer (Contains 200 mM Hepes pH 7, 600 mM NaCl, 40 mM Mgcl$_2$, <1% Cholate (w/v), <1% Chaps (w/v), 0.05% Sodium Azide (w/v))
PIP2 (1 mM)
3× Biotin PIP3 (50 µM)
Detection Mix C (Contains 267 mM KF)
Detection Mix A (Contains 60 µg/ml streptavadin-APC)
Detection Mix B (Contains 36 µg/ml Europium-anti-GST (Anti-GST-K) and 90 µg/ml GST-GRP1-PH-Domain and 1 mM DTT)
Stop Solution (Contains 150 mM EDTA)
Manually add 3 µl of Reaction buffer (contains 1 mM DTT) to column 18 only for 100% inhibition control (no activity)

Manually add 3 µl of 2× Enzyme solution to all wells except column 18. Preincubate with compound for 15 minutes.

Manually add 3 µl of 2× Substrate solution to all wells (column 6 represents 0% inhibition control)

Leave plate for 1 hr (cover from light) (In the case of Gamma only a 50 min incubation is required)

Manually add 3 µl Stop/Detection solution to all wells
Leave plate for 1 hour (cover from light)

The assay is read upon the BMG Rubystar and the ratio data is utilised to calculate 11 point curves.

NB The substrate solution (concentrations) differ with each isoform (see below)

Alpha
2× substrate solution containing 500 µM ATP, 16 µM PIP2 and 0.030 µM 3× biotin-PIP3.

Beta
2× substrate solution containing 800 µM ATP, 16 µM PIP2 and 0.030 µM 3× biotin-PIP3.

Delta
2× substrate solution containing 160 µM ATP, 10 µM PIP2 and 0.030 µM 3× biotin-PIP3.

Gamma
2× substrate solution containing 30 µM ATP, 16 µM PIP2 and 0.030 µM 3× biotin-PIP3.

Analysis Method

Data processed through the XC50 4-parameter logistic curve fit algorithm in Activity Base.

Normalise to % inhibition between the high and low controls (0% and 100% inhibition respectively)

Primary Module fit: Slope, Min and Max asymptotes varies
Secondary Module fits: (1) Fix Min asymptote, (2) Fix Max asymptote, (3) Fix Min and Max asymptotes
Curve Fit QC:pXC50 95% CL ratio>10
−20<Min asymptote<20
80<Max asymptote<120

The compounds of Examples 1 to 100 were tested in one or more of the PI3K Alpha, Beta, Delta and/or Gamma assays above or similar assays and were found to have a mean pIC$_{50}$ of 5 or greater. Certain compounds were also tested in the T cell assay above or a similar assay and were found to have a mean pIC$_{50}$ of 5 or greater.

What is claimed is:

1. A compound of formula (I):

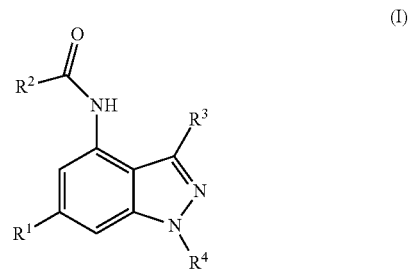

wherein
R$^1$ is 9- or 10-membered bicyclic heteroaryl wherein the 9- or 10-membered bicyclic heteroaryl contains from one to three heteroatoms independently selected from oxygen and nitrogen and is optionally substituted by C$_{1-6}$alkyl, C$_{3-6}$cycloalkyl, halo or —CN;
R$^2$ is pyridinyl optionally substituted by one or two substituents independently selected from C$_{1-6}$alkyl, C$_{2-6}$alkenyl, —OR$^5$, halo, —(CH$_2$)$_m$NR$^6$R$^7$, —SO$_2$R$^8$ and phenyl wherein the phenyl is optionally substituted by one or two substituents independently selected from C$_{1-6}$alkyl and —OR$^9$;
R$^3$ is hydrogen or fluoro;
R$^4$ is hydrogen, methyl or ethyl;
R$^5$ is hydrogen, C$_{1-6}$alkyl or 6-membered heterocyclyl wherein the 6-membered heterocyclyl contains one heteroatom selected from oxygen and nitrogen and is optionally substituted by C$_{1-6}$alkyl;
R$^6$ and R$^7$ are each independently hydrogen, C$_{1-6}$alkyl, C$_{3-6}$cycloalkyl or 6-membered heterocyclyl wherein the 6-membered heterocyclyl contains one heteroatom selected from oxygen and nitrogen and is optionally substituted by C$_{1-6}$alkyl, or R$^6$ and R$^7$, together with the nitrogen atom to which they are attached, are linked to form a 5- or 6-membered heterocyclyl or a 10-membered bicyclic heterocyclyl wherein the 5- or 6-membered heterocyclyl or the 10-membered bicyclic heterocyclyl optionally contains an oxygen atom, a sulphur atom or a further nitrogen atom and is optionally substituted by one or two substituents independently selected from C$_{1-6}$alkyl; C$_{3-6}$cycloalkyl; halo; oxo; phenyl optionally substituted by halo; pyridinyl; —(CH$_2$)$_n$OR$^{10}$; —(CH$_2$)$_p$NR$^{11}$R$^{12}$; —COR$^{13}$; and —SO$_2$R$^{14}$;
R$^8$, R$^{13}$ and R$^{14}$ are each independently C$_{1-6}$alkyl;
R$^9$ is hydrogen or C$_{1-6}$alkyl;
R$^{10}$ is hydrogen, C$_{1-6}$alkyl or —(CH$_2$)$_q$phenyl;
R$^{11}$ and R$^{12}$, together with the nitrogen atom to which they are attached, are linked to form a 5- or 6-membered heterocyclyl optionally containing an oxygen atom; and
m, n, p and q are each independently 0, 1 or 2;
or a salt thereof.

2. A compound according to claim 1 wherein R$^1$ is 9- or 10-membered bicyclic heteroaryl wherein the 9- or 10-membered bicyclic heteroaryl contains from one to three heteroatoms independently selected from oxygen and nitrogen and is optionally substituted by C$_{1-6}$alkyl.

3. A compound according to claim 1 wherein R$^1$ is indolyl optionally substituted by C$_{1-6}$alkyl.

4. A compound according to claim 1 wherein $R^2$ is pyridinyl optionally substituted by one or two substituents independently selected from $C_{1-6}$alkyl and —$(CH_2)_n NR^6 R^7$.

5. A compound according to claim 4 wherein $R^2$ is pyridinyl optionally substituted by $C_{1-6}$alkyl.

6. A compound according to claim 1 wherein $R^3$ is hydrogen.

7. A compound according to claim 1 wherein $R^4$ is hydrogen.

8. A compound which is:

N-[6-(1H-indol-4-yl)-1H-indazol-4-yl]-3-methyl-2-pyridinecarboxamide;
3-bromo-N-[6-(1H-indol-4-yl)-1H-indazol-4-yl]-2-pyridinecarboxamide;
5-fluoro-N-[6-(1H-indol-4-yl)-1H-indazol-4-yl]-2-pyridinecarboxamide;
N-[6-(1H-indol-4-yl)-1H-indazol-4-yl]-6[5-methyl-2-(methyloxy)phenyl]-2-pyridinecarboxamide;
N-[6-(1H-indol-4-yl)-1H-indazol-4-yl]-6-(methyloxy)-2-pyridinecarboxamide;
N-[6-(1H-indol-4-yl)-1H-indazol-4-yl]-6-methyl-2-pyridinecarboxamide;
3,5-difluoro-N-[6-(1H-indol-4-yl)-1H-indazol-4-yl]-2-pyridinecarboxamide;
N-[1-ethyl-6-(1H-indol-4-yl)-1H-indazol-4-yl]-6-methyl-2-pyridinecarboxamide;
N-[6-(1H-indol-4-yl)-1-methyl-1H-indazol-4-yl]-2-pyridinecarboxamide;
N-[6-(1H-indol-4-yl)-1H-indazol-4-yl]-3-(methyloxy)-2-pyridinecarboxamide;
6-[(dimethylamino)methyl]-N-[6-(1H-indol-4-0-1H-indazol-4-yl]-2-pyridinecarboxamide;
N-[6-(1H-indol-4-yl)-1H-indazol-4-yl]-6-(4-morpholinylmethyl)-2-pyridinecarboxamide;
N-[6-(1H-indol-4-yl)-1H-indazol-4-yl]-6-(1-piperidinylmethyl)-2-pyridinecarboxamide;
3-fluoro-N-[6-(1H-indol-4-0-1H-indazol-4-yl]-2-pyridinecarboxamide;
N-[6-(1H-indol-4-yl)-1H-indazol-4-yl]-3-pyridinecarboxamide;
N-[6-(1H-indol-4-yl)-1H-indazol-4-yl]-3-(methylsulfonyl)-2-pyridinecarboxamide;
6-chloro-3-fluoro-N-[6-(1H-indol-4-0-1H-indazol-4-yl]-2-pyridinecarboxamide;
6-chloro-N-[6-(1H-indol-4-0-1H-indazol-4-yl]-2-pyridinecarboxamide;
N-[6-(1H-indol-4-yl)-1H-indazol-4-yl]-6-(methylamino)-2-pyridinecarboxamide;
N-[6-(1H-indol-4-yl)-1H-indazol-4-yl]-6-[(1-methylethyl)amino]-2-pyridinecarboxamide;
6-(ethylamino)-N-[6-(1H-indol-4-0-1H-indazol-4-yl]-2-pyridinecarboxamide;
6-(diethylamino)-N-[6-(1H-indol-4-yl)-1H-indazol-4-yl]-2-pyridinecarboxamide;
6-(cyclopropylamino)-N-[6-(1H-indol-4-yl)-1H-indazol-4-yl]-2-pyridinecarboxamide;
N-[6-(1H-indol-4-yl)-1H-indazol-4-yl]-6-(4-methyl-1-piperazinyl)-2-pyridinecarboxamide;
N-[6-(1H-indol-4-yl)-1H-indazol-4-yl]-6-(1-pyrrolidinyl)-2-pyridinecarboxamide;
6-(dimethylamino)-N-[6-(1H-indol-4-0-1H-indazol-4-yl]-2-pyridinecarboxamide;
3,6-dichloro-N-[6-(1H-indo1-4-0-1H-indazol-4-yl]-2-pyridinecarboxamide;
3-chloro-N-[6-(1H-indol-4-0-1H-indazol-4-yl]-6-(4-morpholinyl)-2-pyridinecarboxamide;
3-chloro-N-[6-(1H-indol-4-0-1H-indazol-4-yl]-6-(1-piperidinyl)-2-pyridinecarboxamide;
3-chloro-6-(dimethylamino)-N-[6-(1H-indol-4-0-1H-indazol-4-yl]-2-pyridinecarboxamide;
6-fluoro-N-[6-(1H-indol-4-0-1H-indazol-4-yl]-2-pyridinecarboxamide;
N-[6-(1H-indol-4-yl)-1H-indazol-4-yl]-6-[methyl(tetrahydro-2H-pyran-4-yl)amino]-2-pyridinecarboxamide;
N-[6-(1H-indol-4-yl)-1H-indazol-4-yl]-6-[(1-methyl-4-piperidinyl)amino]-2-pyridinecarboxamide;
N-[6-(1H-indol-4-yl)-1H-indazol-4-yl]-6-(tetrahydro-2H-pyran-4-ylamino)-2-pyridinecarboxamide;
6-chloro-3-(dimethylamino)-N-[6-(1H-indol-4-0-1H-indazol-4-yl]-2-pyridinecarboxamide;
3-(dimethylamino)-N-[6-(1H-indol-4-0-1H-indazol-4-yl]-6-(4-morpholinyl)-2-pyridinecarboxamide;
3-(dimethylamino)-N-[6-(1H-indol-4-0-1H-indazol-4-yl]-6-(1-piperidinyl)-2-pyridinecarboxamide;
3-(dimethylamino)-N-[6-(1H-indol-4-0-1H-indazol-4-yl]-6-(methylamino)-2-pyridinecarboxamide;
3-(dimethylamino)-6-(ethylamino)-N-[6-(1H-indol-4-yl)-1H-indazol-4-yl]-2-pyridinecarboxamide;
6-chloro-N-[6-(1H-indol-4-0-1H-indazol-4-yl]-3-(4-morpholinyl)-2-pyridinecarboxamide;
6-chloro-N-[6-(1H-indol-4-0-1H-indazol-4-yl]-3-(1-piperidinyl)-2-pyridinecarboxamide;
N-[6-(1H-indol-4-yl)-1H-indazol-4-yl]-5-(4-morpholinyl)-2-pyridinecarboxamide;
N-[6-(1H-indol-4-yl)-1H-indazol-4-yl]-5-(1-piperidinyl)-2-pyridinecarboxamide;
3-chloro-N-[6-(1H-indol-4-yl)-1H-indazol-4-yl]-2-pyridinecarboxamide;
6-amino-N-[6-(1H-indol-4-yl)-1H-indazol-4-yl]-2-pyridinecarboxamide;
5-amino-N-[6-(1H-indol-4-yl)-1H-indazol-4-yl]-2-pyridinecarboxamide;
N-[6-(1H-indol-4-yl)-1H-indazol-4-yl]-5-methyl-2-pyridinecarboxamide;
N-[6-(1H-indol-4-yl)-1H-indazol-4-yl]-2-methyl-3-pyridinecarboxamide;
3-amino-N-[6-(1H-indol-4-yl)-1H-indazol-4-yl]-2-pyridinecarboxamide;
N-[6-(1H-indol-4-yl)-1H-indazol-4-yl]-4-(methylamino)-2-pyridinecarboxamide;
N-[6-(1H-indol-4-yl)-1H-indazol-4-yl]-2-pyridinecarboxamide;
N-[6-(1H-indol-6-yl)-1H-indazol-4-yl]-2-pyridinecarboxamide;
N-[6-(1-methyl-1H-indol-5-yl)-1H-indazol-4-yl]-2-pyridinecarboxamide;
N-[6-(1H-indol-4-yl)-1H-indazol-4-yl]-2-(methyloxy)-3-pyridinecarboxamide;
2-(ethyloxy)-N-[6-(1H-indol-4-yl)-1H-indazol-4-yl]-3-pyridinecarboxamide;
5-bromo-N-[6-(1H-indol-4-yl)-1H-indazol-4-yl]-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1H-indazol-4-yl]-6-(4-morpholinyl)-2-pyridinecarboxamide;
N-[6-(1H-indol-4-yl)-1H-indazol-4-yl]-6-oxo-1,6-dihydro-2-pyridinecarboxamide;
N-[6-(1H-indol-4-yl)-1H-indazol-4-yl]-2-(1-pyrrolidinyl)-4-pyridinecarboxamide;
N-[6-(1H-indol-4-yl)-1-methyl-1H-indazol-4-yl]-6-methyl-2-pyridinecarboxamide;

N-[6-(1H-indol-4-yl)-1H-indazol-4-yl]-3-(1-methylethenyl)-2-pyridinecarboxamide;

N-[6-(1H-indol-4-yl)-1H-indazol-4-yl]-3-(1-methylethyl)-2-pyridinecarboxamide;

N-[6-(1H-indol-4-yl)-1H-indazol-4-yl]-6-(tetrahydro-2H-pyran-4-yloxy)-2-pyridinecarboxamide;

N-[6-(1H-indol-4-yl)-1H-indazol-4-yl]-6-[(4-methyl-1-piperazinyl)methyl]-2-pyridinecarboxamide;

N-[3-fluoro-6-(1H-indol-4-yl)-1H-indazol-4-yl]-3-methyl-2-pyridinecarboxamide;

6-[(4,4-dimethyl-1-piperidinyl)methyl]-N-[6-(1H-indol-4-yl)-1H-indazol-4-yl]-2-pyridinecarboxamide;

6-[(3,3-dimethyl-1-piperidinyl)methyl]-N-[6-(1H-indol-4-yl)-1H-indazol-4-yl]-2-pyridinecarboxamide;

N-[6-(1H-indol-4-yl)-1H-indazol-4-yl]-6-{[4-(2-methylpropyl)-1-piperazinyl]methyl}-2-pyridinecarboxamide;

N-[6-(1H-indol-4-yl)-1H-indazol-4-yl]-6-{[4-(1-methylethyl)-1-piperazinyl]methyl}-2-pyridinecarboxamide;

N-[6-(1H-indol-4-yl)-1H-indazol-4-yl]-6-{[4-(1-methylethyl)-1-piperazinyl]methyl}-2-pyridinecarboxamide;

N-[6-(1H-indol-4-yl)-1H-indazol-4-yl]-6-({4[2-(4-morpholinyl)ethyl]-1-piperazinyl}methyl)-2-pyridinecarboxamide;

N-[6-(1H-indol-4-yl)-1H-indazol-4-yl]-6-(octahydro-4H-1,4-benzoxazin-4-ylmethyl)-2-pyridinecarboxamide;

6-{[(2R,6S)-2,6-dimethyl-4-morpholinyl]methyl}-N-[6-(1H-indol-4-yl)-1H-indazol-4-yl]-2-pyridinecarboxamide;

6-{[4-(4-fluorophenyl)-1-piperazinyl]methyl}-N-[6-(1H-indol-4-yl)-1H-indazol-4-yl]-2-pyridinecarboxamide;

N-[6-(1H-indol-4-yl)-1H-indazol-4-yl]-6-(octahydro-2H-pyrido[1,2-a]pyrazin-2-ylmethyl)-2-pyridinecarboxamide;

N-[6-(1H-indol-4-yl)-1H-indazol-4-yl]-6-{[2-(1-pyrrolidinylmethyl)-4-morpholinyl]methyl}-2-pyridinecarboxamide;

N-[6-(1H-indol-4-yl)-1H-indazol-4-yl]-6-{[2-(2-methylpropyl)-4-morpholinyl]methyl}-2-pyridinecarboxamide;

N-[6-(1H-indol-4-yl)-1H-indazol-4-yl]-6-{[3-methyl-4-(1-methylethyl)-1-piperazinyl]methyl}-2-pyridinecarboxamide;

N-[6-(1H-indol-4-yl)-1H-indazol-4-yl]-6-[(3-phenyl-1-piperidinyl)methyl]-2-pyridinecarboxamide;

N-[6-(1H-indol-4-yl)-1H-indazol-4-yl]-6-({2-[(phenyloxy)methyl]-4-morpholinyl}methyl)-2-pyridinecarboxamide;

N-[6-(1H-indol-4-yl)-1H-indazol-4-yl]-6-({3-[(phenylmethyl)oxy]-1-piperidinyl}methyl)-2-pyridinecarboxamide;

6-{[4-(1-ethylpropyl)-1-piperazinyl]methyl}-N-[6-(1H-indol-4-yl)-1H-indazol-4-yl]-2-pyridinecarboxamide;

6-[(4-cyclopentyl-1-piperazinyl)methyl]-N-[6-(1H-indol-4-yl)-1H-indazol-4-yl]-2-pyridinecarboxamide;

6-methyl-N-[1-methyl-6-(1H-pyrrolo[2,3-b]pyridin-4-yl)-1H-indazol-4-yl]-2-pyridinecarboxamide;

6-(4-morpholinylmethyl)-N-[6-(1H-pyrrolo[2,3-b]pyridin-4-yl)-1H-indazol-4-yl]-2-pyridinecarboxamide;

6-(1-piperidinylmethyl)-N-[6-(1H-pyrrolo[2,3-b]pyridin-4-yl)-1H-indazol-4-yl]-2-pyridinecarboxamide;

6-[(4-methyl-3-oxo-1-piperazinyl)methyl]-N-[6-(1H-pyrrolo[2,3-b]pyridin-4-yl)-1H-indazol-4-yl]-2-pyridinecarboxamide;

6-[(4-acetyl-1-piperazinyl)methyl]-N-[6-(1H-pyrrolo[2,3-b]pyridin-4-yl)-1H-indazol-4-yl]-2-pyridinecarboxamide;

6-{[4-(methylsulfonyl)-1-piperazinyl]methyl}-N-[6-(1H-pyrrolo[2,3-b]pyridin-4-yl)-1H-indazol-4-yl]-2-pyridinecarboxamide;

6-[(1,1-dioxido-4-thiomorpholinyl)methyl]-N-[6-(1H-pyrrolo[2,3-b]pyridin-4-yl)-1H-indazol-4-yl]-2-pyridinecarboxamide;

6-{[(2R,6S)-2,6-dimethyl-4-morpholinyl]methyl}-N-[6-(1H-pyrrolo[2,3-b]pyridin-4-yl)-1H-indazol-4-yl]-2-pyridinecarboxamide;

6-{[3-methyl-4-(1-methylethyl)-1-piperazinyl]methyl}-N-[6-(1H-pyrrolo[2,3-b]pyridin-4-yl)-1H-indazol-4-yl]-2-pyridinecarboxamide;

6-[(4,4-difluoro-1-piperidinyl)methyl]-N-[6-(1H-pyrrolo[2,3-b]pyridin-4-yl)-1H-indazol-4-yl]-2-pyridinecarboxamide;

6-(4-morpholinylmethyl)-N-[6-(1H-pyrazolo[3,4-b]pyridin-5-yl)-1H-indazol-4-yl]-2-pyridinecarboxamide;

6-{[4-(methylsulfonyl)-1-piperazinyl]methyl}-N-[6-(1H-pyrazolo[3,4-b]pyridin-5-yl)-1H-indazol-4-yl]-2-pyridinecarboxamide;

6-[(1,1-dioxido-4-thiomorpholinyl)methyl]-N-[6-(1H-pyrazolo[3,4-b]pyridin-5-yl)-1H-indazol-4-yl]-2-pyridinecarboxamide;

6-[(4,4-difluoro-1-piperidinyl)methyl]-N-[6-(1H-pyrazolo[3,4-b]pyridin-5-yl)-1H-indazol-4-yl]-2-pyridinecarboxamide;

6-{[(2R,6S)-2,6-dimethyl-4-morpholinyl]methyl}-N-[6-(1H-pyrazolo[3,4-b]pyridin-5-yl)-1H-indazol-4-yl]-2-pyridinecarboxamide;

6-{[3-methyl-4-(1-methylethyl)-1-piperazinyl]methyl}-N-[6-(1H-pyrazolo[3,4-b]pyridin-5-yl)-1H-indazol-4-yl]-2-pyridinecarboxamide; or a salt thereof

9. A compound according to claim 1 in the form of a pharmaceutically acceptable salt thereof.

10. A pharmaceutical composition comprising a compound as defined in claim 1, or a pharmaceutically acceptable salt thereof, and one or more pharmaceutically acceptable excipients.

\* \* \* \* \*